US012788889B2

(12) United States Patent
Dasbach et al.

(10) Patent No.: US 12,788,889 B2
(45) Date of Patent: Nov. 10, 2026

(54) ARRANGEMENT FOR A DRUG DELIVERY DEVICE AND DRUG DELIVERY DEVICE

(71) Applicant: Sanofi, Paris (FR)

(72) Inventors: Uwe Dasbach, Frankfurt am Main (DE); Thomas Mark Kemp, Melbourn (GB); Timothy Denyer, Melbourn (GB); Robbie Wilson, Melbourn (GB); Chris Rosier, Melbourn (GB)

(73) Assignee: Sanofi, Paris (FR)

( * ) Notice: Subject to any disclaimer, the term of this patent is extended or adjusted under 35 U.S.C. 154(b) by 677 days.

(21) Appl. No.: 18/039,110

(22) PCT Filed: Dec. 1, 2021

(86) PCT No.: PCT/EP2021/083818
§ 371 (c)(1),
(2) Date: May 26, 2023

(87) PCT Pub. No.: WO2022/117671
PCT Pub. Date: Jun. 9, 2022

(65) Prior Publication Data

US 2024/0207519 A1 Jun. 27, 2024

(30) Foreign Application Priority Data

Dec. 2, 2020 (EP) .................................... 20315471

(51) Int. Cl.
*A61M 5/31* (2006.01)
*A61M 5/20* (2006.01)
(Continued)

(52) U.S. Cl.
CPC ...... *A61M 5/2033* (2013.01); *A61M 5/31585* (2013.01); *A61M 2005/2073* (2013.01); *A61M 2005/3267* (2013.01)

(58) Field of Classification Search
CPC ....... F04C 2270/0421; A61M 5/31583; A61M 5/31585; A61M 5/31578; A61M 5/31551
See application file for complete search history.

(56) References Cited

U.S. PATENT DOCUMENTS 5,322,511 A 6/1994 Armbruster et al.
2005/0261634 A1 11/2005 Karlsson
(Continued)

FOREIGN PATENT DOCUMENTS

CN 1141597 A 1/1997
CN 102448525 A 5/2012
(Continued)

OTHER PUBLICATIONS

International Preliminary Report on Patentability in International Appln. No. PCT/EP2021/083818, mailed on Jun. 15, 2023, 8 pages.
(Continued)

*Primary Examiner* — Deanna K Hall
(74) *Attorney, Agent, or Firm* — Fish & Richardson P.C.

(57) ABSTRACT

An arrangement for a drug delivery device includes a housing element, a plunger rod being arranged axially movable with respect to the housing element, a transfer member being arranged rotatably with respect to the housing element, an energy member configured to provide energy to induce a torque onto the transfer member, wherein the transfer member and the plunger rod are operatively coupled such that a rotation of the transfer member is converted into an axial movement of the plunger rod. The arrangement comprises a released state in which (i) the energy member induces a torque onto the transfer member, and (ii) the transfer member rotates in a first rotational direction due to the induced torque and thereby forces the plunger rod to move axially in a distal direction. The plunger rod being rotationally fixed with respect to the housing element.

18 Claims, 38 Drawing Sheets

(51) Int. Cl.
*A61M 5/315* (2006.01)
*A61M 5/32* (2006.01)

(56) References Cited

U.S. PATENT DOCUMENTS

| | | | | |
|---|---|---|---|---|
| 2005/0273079 | A1 | 12/2005 | Hohlfelder et al. | |
| 2011/0251553 | A1 | 10/2011 | Ratjen et al. | |
| 2012/0029443 | A1 | 2/2012 | Holmqvist | |
| 2013/0041327 | A1 | 2/2013 | Daniel | |
| 2013/0131602 | A1* | 5/2013 | Kemp | A61M 5/3202 604/197 |
| 2013/0138049 | A1 | 5/2013 | Kemp et al. | |
| 2013/0204196 | A1 | 8/2013 | Roberts et al. | |
| 2013/0289492 | A1 | 10/2013 | Brereton et al. | |
| 2015/0374927 | A1 | 12/2015 | Dasbach | |
| 2016/0106923 | A1 | 4/2016 | Brereton et al. | |
| 2016/0151585 | A1 | 6/2016 | Kemp | |
| 2016/0193413 | A1 | 7/2016 | Gabrielsson | |
| 2016/0287812 | A1 | 10/2016 | Nielsen et al. | |
| 2016/0361503 | A1 | 12/2016 | Bendek et al. | |
| 2017/0056600 | A1 | 3/2017 | Schoonmaker | |
| 2017/0136192 | A1 | 5/2017 | Stefansen et al. | |
| 2017/0173264 | A1 | 6/2017 | Bendek et al. | |
| 2018/0126088 | A1 | 5/2018 | Radmer et al. | |
| 2018/0169346 | A1 | 6/2018 | Hostettler et al. | |
| 2018/0169349 | A1 | 6/2018 | Mosebach et al. | |
| 2018/0333537 | A1 | 11/2018 | Wendland et al. | |
| 2018/0344943 | A1 | 12/2018 | Halm | |
| 2019/0217017 | A1 | 7/2019 | Schabbach et al. | |
| 2019/0328968 | A1 | 10/2019 | Giambattista | |
| 2020/0155767 | A1 | 5/2020 | Bough et al. | |
| 2020/0384208 | A1 | 12/2020 | Greven | |
| 2021/0154414 | A1 | 5/2021 | Jones et al. | |
| 2021/0170108 | A1 | 6/2021 | Säll et al. | |
| 2023/0414879 | A1 | 12/2023 | Dasbach et al. | |
| 2024/0001041 | A1 | 1/2024 | Dasbach et al. | |
| 2024/0017018 | A1 | 1/2024 | Dasbach et al. | |
| 2024/0033441 | A1 | 2/2024 | Dasbach et al. | |
| 2024/0033443 | A1 | 2/2024 | Dasbach et al. | |
| 2024/0207530 | A1 | 6/2024 | Dasbach et al. | |

FOREIGN PATENT DOCUMENTS

| | | | |
|---|---|---|---|
| CN | 102917738 | A | 2/2013 |
| CN | 103025371 | A | 4/2013 |
| CN | 103492000 | A | 1/2014 |
| CN | 104703645 | A | 6/2015 |
| CN | 104968385 | A | 10/2015 |
| CN | 105517600 | A | 4/2016 |
| CN | 105705183 | A | 6/2016 |
| CN | 106068135 | A | 11/2016 |
| CN | 106456889 | A | 2/2017 |
| CN | 107666924 | A | 2/2018 |
| CN | 107708775 | A | 2/2018 |
| CN | 107995872 | A | 5/2018 |
| CN | 108495667 | A | 9/2018 |
| CN | 108601902 | A | 9/2018 |
| CN | 108697851 | A | 10/2018 |
| CN | 110248686 | A | 9/2019 |
| CN | 110520175 | A | 11/2019 |
| CN | 110681004 | A | 1/2020 |
| CN | 111093737 | A | 5/2020 |
| CN | 111526904 | A | 8/2020 |
| CN | 111282094 | B | 11/2020 |
| CN | 111936183 | A | 11/2020 |
| JP | H09-507400 | A | 7/1997 |
| JP | 2004-510552 | A | 4/2004 |
| JP | 2006-500150 | A | 1/2006 |
| JP | 2014-502882 | A | 2/2014 |
| JP | 2015-523900 | A | 8/2015 |
| JP | 2016-535656 | A | 11/2016 |
| JP | 2017-519580 | A | 7/2017 |
| JP | 2018-515232 | A | 6/2018 |
| JP | 2018-516691 | A | 6/2018 |
| JP | 2019-503207 | A | 2/2019 |
| JP | 2020-510490 | A | 4/2020 |
| WO | WO 1995/013841 | A1 | 5/1995 |
| WO | WO 2002/030490 | A2 | 4/2002 |
| WO | WO 2004/028598 | A1 | 4/2004 |
| WO | WO 2011/039236 | A1 | 4/2011 |
| WO | WO 2012/085025 | A1 | 6/2012 |
| WO | WO 2013/192328 | A1 | 12/2013 |
| WO | WO 2015/071289 | A1 | 5/2015 |
| WO | WO 2015/090320 | | 6/2015 |
| WO | WO 2015/197867 | A1 | 12/2015 |
| WO | WO 2016/180873 | A1 | 11/2016 |
| WO | WO 2016/193349 | A1 | 12/2016 |
| WO | WO 2016/193350 | A1 | 12/2016 |
| WO | WO 2016/193374 | A1 | 12/2016 |
| WO | WO 2018/037034 | A1 | 3/2018 |
| WO | WO 2018/166985 | A1 | 9/2018 |
| WO | WO 2019/086564 | A1 | 5/2019 |
| WO | WO 2019/191104 | A1 | 10/2019 |
| WO | WO 2019/234134 | | 12/2019 |
| WO | WO 2020/152192 | | 7/2020 |
| WO | WO 2022/117671 | | 6/2022 |
| WO | WO 2022/117673 | | 6/2022 |
| WO | WO 2022/117676 | | 6/2022 |
| WO | WO 2022/117682 | | 6/2022 |
| WO | WO 2022/117683 | | 6/2022 |
| WO | WO 2022/117684 | | 6/2022 |
| WO | WO 2022/117685 | | 6/2022 |

OTHER PUBLICATIONS

International Preliminary Report on Patentability in International Appln. No. PCT/EP2021/083821, mailed on Jun. 15, 2023, 8 pages.
International Preliminary Report on Patentability in International Appln. No. PCT/EP2021/083826, mailed on Jun. 15, 2023, 9 pages.
International Preliminary Report on Patentability in International Appln. No. PCT/EP2021/083839, mailed on Jun. 15, 2023, 9 pages.
International Preliminary Report on Patentability in International Appln. No. PCT/EP2021/083840, mailed on Jun. 15, 2023, 10 pages.
International Preliminary Report on Patentability in International Appln. No. PCT/EP2021/083842, mailed on Jun. 15, 2023, 12 pages.
International Preliminary Report on Patentability in International Appln. No. PCT/EP2021/083843, mailed on Jun. 15, 2023, 9 pages.
Third Party Observations in European Appln. No. 21819137.7, dated Feb. 7, 2024, 6 pages.
International Search Report and Written Opinion in International Appln. No. PCT/EP2021/083818, mailed on Feb. 22, 2022, 9 pages.
International Search Report and Written Opinion in International Appln. No. PCT/EP2021/083821, mailed on Feb. 22, 2022, 9 pages.
International Search Report and Written Opinion in International Appln. No. PCT/EP2021/083826, mailed on Feb. 24, 2022, 11 pages.
International Search Report and Written Opinion in International Appln. No. PCT/EP2021/083839, mailed on Feb. 23, 2022, 10 pages.
International Search Report and Written Opinion in International Appln. No. PCT/EP2021/083840, mailed on Feb. 23, 2022, 11 pages.
International Search Report and Written Opinion in International Appln. No. PCT/EP2021/083842, mailed on May 18, 2022, 15 pages.
International Search Report and Written Opinion in International Appln. No. PCT/EP2021/083843, mailed on Feb. 23, 2022, 11 pages.
U.S. Appl. No. 18/038,745, filed May 25, 2023, Uwe Dasbach.
U.S. Appl. No. 18/038,859, filed May 25, 2023, Uwe Dasbach.
U.S. Appl. No. 18/038,748, filed May 25, 2023, Uwe Dasbach.
U.S. Appl. No. 18/039,019, filed May 26, 2023, Uwe Dasbach.
U.S. Appl. No. 18/038,368, filed May 23, 2023, Uwe Dasbach.
U.S. Appl. No. 18/039,045, filed May 26, 2023, Uwe Dasbach.

* cited by examiner

ARRANGEMENT FOR A DRUG DELIVERY DEVICE AND DRUG DELIVERY DEVICE

CROSS REFERENCE TO RELATED APPLICATIONS

The present application is the national stage entry of International Patent Application No. PCT/EP2021/083818, filed on Dec. 1, 2021, and claims priority to Application No. EP 20315471.1, filed on Dec. 2, 2020, the disclosures of which are incorporated herein by reference.

TECHNICAL FIELD

An arrangement for a drug delivery device is provided. Furthermore, a drug delivery device is provided.

BACKGROUND

Administering an injection is a process which presents a number of risks and challenges for users and healthcare professionals, both mental and physical. A drug delivery device may aim to make self-injection easier for patients. A conventional drug delivery device may provide the force for administering the injection by a spring, and trigger button or another mechanism may be used to activate the injection. Drug delivery devices may be single-use or reusable devices.

SUMMARY

An improved arrangement for a drug delivery device and an improved drug delivery device are disclosed.

Firstly, the arrangement for the drug delivery device is specified. The arrangement may be a unit of the drug delivery device, e.g. a subassembly of the drug delivery device.

According to at least one embodiment, the arrangement comprises a housing element. The housing element may be hollow and/or elongated. The housing element may be a sleeve, e.g. a cylindrically-shaped sleeve. Particularly, the housing element may be a holder for an energy member such as a drive spring, i.e. an element in which an energy member can be stored. The energy member may be secured to the housing element, e.g. by fixing one end of the drive spring to the housing element.

According to at least one embodiment, the arrangement comprises a plunger rod, being arranged axially, i.e. in only one or two opposite axial directions, movable with respect to the housing element. The plunger rod may be hollow or solid. The plunger rod may be cylindrically-shaped, e.g. hollow-cylindrically-shaped. In case that the plunger rod is hollow, further elements or members, e.g. other than an energy member for driving the plunger rod, may be received in the plunger rod.

According to at least one embodiment, the arrangement comprises a transfer member. The transfer member may be arranged rotatably with respect to the housing element. The transfer member may be hollow and/or elongated. The transfer member may be a sleeve. For example, the transfer member is a rotating collar. The transfer member may be configured to be rotated in one or two opposite rotational directions. The rotational axis of the transfer member may define or coincide with a longitudinal axis of the arrangement or the drug delivery device.

The housing element and/or the plunger rod and/or the transfer member may comprise or consist of a plastic. Each of them may be formed in one piece, i.e. be of a unitary construction or integrally formed. Each of them may have a main extension direction parallel the longitudinal axis. The longitudinal axis may run through one or more or every of the mentioned elements/members, e.g. through the center thereof.

According to at least one embodiment, the arrangement comprises an energy member configured to provide energy in order to induce a torque onto the transfer member, preferably to drive the transfer member. In other words, the energy member may be configured to provide energy to rotate the transfer member relative to the housing element. The energy member may be a drive spring, e.g. a torsion drive spring, particularly a spiral torsion spring or clock spring or power spring, or another component configured to induce a torque, e.g. a gas cartridge or an electric motor. The drive spring may be formed of metal, e.g. steel. The longitudinal axis may run through the center of the drive spring.

The plunger rod may be received in the transfer member so that the transfer member circumferentially surrounds, e.g. completely circumferentially surrounds, at least a portion of the plunger rod. The transfer member may be received in the housing element and/or the energy member so that at least a portion of the transfer member is circumferentially surrounded, e.g. completely circumferentially surrounded, by the housing element and/or the energy member. The energy member may be received in the housing element so that at least a portion of the energy member is circumferentially surrounded, e.g. completely circumferentially surrounded, by the housing element.

According to at least one embodiment, the transfer member and the plunger rod are operatively coupled such that a rotation of the transfer member is converted or convertible into an axial movement of the plunger rod. The plunger rod and the transfer member may be coupled by a gear, e.g. a threaded interface, transforming a rotational movement of the transfer member into an axial movement of the plunger rod.

Here and in the following, if not stated otherwise, a movement of a member or element or feature is to be understood as a movement with respect to the housing element.

According to at least one embodiment, the arrangement comprises a released state in which the energy member induces a torque onto the transfer member.

According to at least one embodiment, in the released state, the transfer member rotates in a first rotational direction due to the induced torque and thereby forces the plunger rod to move axially in the distal direction. The first rotational direction may be clockwise or counterclockwise when viewed in plan view onto the distal end of the arrangement. In the released state, the transfer member may rotate by an angle greater than or equal to any one of the following values: 60°, 80°, 120°, 180°, 270°, 360°. Preferably, in the released state, the transfer member rotates at least by 360° or by more than 360°. For example, the transfer member may rotate several times around its rotational axis. The plunger rod may, in the released state, move by at least 1 cm in the distal direction driven by the transfer member.

According to at least one embodiment, the plunger rod is rotationally fixed with respect to the housing element. This means that the plunger rod does not rotate or is prevented from rotating during movement in an axial direction, for example in the distal direction.

In at least one embodiment, the arrangement for a drug delivery device comprises a housing element, a plunger rod being arranged axially movable with respect to the housing element, a transfer member being arranged rotatably with respect to the housing element and an energy member configured to provide energy in order to induce a torque onto the transfer member. The transfer member and the plunger rod are operatively coupled such that a rotation of the transfer member is converted into an axial movement of the plunger rod. The arrangement comprises a released state in which the energy member induces a torque onto the transfer member and the transfer member rotates in a first rotational direction due to the induced torque and thereby forces the plunger rod to move axially in a distal direction. The plunger rod is rotationally fixed with respect to the housing element.

With the plunger rod being rotationally fixed to the housing element, i.e. not rotating during movement in distal direction, friction induced by the plunger rod when hitting a stopper of a medicament container/syringe is reduced. Consequently, less heat is produced. A separate bearing element at the distal end of the plunger rod can be avoided in this way.

The drug delivery device and/or the arrangement for the drug delivery device specified herein may be elongated and/or may comprise a longitudinal axis, i.e. a main extension axis. A direction parallel to the longitudinal axis is herein called an axial direction. By way of example, the drug delivery device and/or the arrangement may be cylindrically-shaped.

Furthermore, the drug delivery device and/or the arrangement may comprise a longitudinal end, which may be provided to face or to be pressed against a skin region of a human body. This end is herein called the distal end. A drug or medicament may be supplied via the distal end. The opposing longitudinal end is herein called the proximal end. The proximal end is, during usage, remote from the skin region. The axial direction pointing from the proximal end to the distal end is herein called distal direction. The axial direction pointing from the distal end to the proximal end is herein called proximal direction. A distal end of a member or element of the drug delivery device and/or of the arrangement is herein understood to be the end of the member/element located most distally. Accordingly, the proximal end of a member or element is herein understood to be the end of the element/member located most proximally.

In other words, "distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is herein used to specify directions, ends or surfaces which are arranged or are to be arranged to face away from or point away from the dispensing end and/or from the distal end of the drug delivery device or components thereof. The distal end may be the end closest to the dispensing end and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be a needle end where a needle unit is or is to be mounted to the device, for example.

A direction perpendicular to the longitudinal axis and/or intersecting with the longitudinal axis is herein called radial direction. An inward radial direction is a radial direction pointing towards the longitudinal axis. An outward radial direction is a radial direction pointing away from the longitudinal axis.

The terms "angular direction", "azimuthal direction" or "rotational direction" are herein used as synonyms. Such a direction is a direction perpendicular to the longitudinal axis and perpendicular to the radial direction.

An element or member or feature being rotationally, axially or radially fixed with respect to another element or member or feature means that a relative movement in rotational direction or axial direction or radial direction between the two elements/members/features is not possible or prevented.

The terms "protrusion" and "boss" are used as synonyms herein. The term "recess" may particularly stand for an indentation or a cut-out or opening or hole.

According to at least one embodiment, the arrangement comprises at least one locked state, e.g. a first and a second locked state. A locked state may be a state of the arrangement prior to the released state. In the locked state(s), the energy member may already induce a torque onto the transfer member. For example, the drive spring is already biased. However, in the locked state(s), rotation of the transfer member is prevented, e.g. by means of a locking mechanism.

According to at least one embodiment, the plunger rod is rotationally fixed to the housing element via a splined interface. The splined interface may be formed directly between the plunger rod and the housing element. For example, the plunger rod has a splining element and the housing element has a splining element, e.g. complementary to and/or mating with the splining element of the plunger rod. The splining elements of the plunger rod and the housing element may engage with each other, e.g. formlockingly, thereby preventing the rotation of the plunger rod with respect to the housing element.

One of the splining elements of the housing element and of the plunger rod may be a groove and the other one of the splining elements of the housing element and the plunger rod may be a protrusion. The protrusion may then engage or project into the groove thereby preventing rotation of the plunger rod. The groove may extend parallel to the longitudinal axis. For example, the groove is formed in the plunger rod and the protrusion is part of the housing element, e.g. integrally formed with the housing element.

The housing element may comprise several splining elements, each of them engaging with an assigned splining element of the plunger rod. For example, the plunger rod comprises several grooves, e.g. at least two grooves, arranged rotational symmetrically with respect to the longitudinal axis. Accordingly, the housing element may comprise several protrusions, arranged rotational symmetrically with respect to the longitudinal axis.

According to at least one embodiment, in the released state, the transfer member rotates by at least n-times 360°, wherein n is an integer greater or equal 1. For example, n is one of: 1, 2, 3, 4, 5, 6, 7, 8, 9, 10.

According to at least one embodiment, the plunger rod and the transfer member are operatively coupled via a threaded interface. The threaded interface may be formed directly between the plunger rod and the transfer member. The threaded interface may transform the rotational movement of the transfer member into an axial movement of the plunger rod. The plunger rod may comprise a thread engaged with a thread of the transfer member. The thread of the plunger rod may be an external thread, the thread of the transfer member may be an internal thread, or vice versa. The transfer member may be axially secured to the housing element, e.g. via the energy member. For example, one end of the drive spring not fixed to the housing element is fixed to the transfer member. For example, the transfer member is secured to the housing such that a force necessary for moving the transfer member in one or both axial directions, particularly in the proximal direction, is greater than a force necessary to axially move the plunger rod.

Preferably, the splined interface is in close proximity to the threaded interface, e.g. with a distance of at most 1 cm or at most 0.5 cm or at most 0.2 cm. This is beneficial since the torque on the plunger rod is resolved over a short distance reducing the stresses within the plunger rod.

According to at least one embodiment, the arrangement has a first locked state, in which a releasable first locking mechanism, also referred to as first rotation-locking mechanism, prevents or blocks a rotational movement of the transfer member. In the first locked state, the first locking mechanism may establish a rotation-lock interface via which the transfer member and the housing element are coupled thereby preventing the rotational movement of the transfer member.

During the intended usage, the first locked state may be a state prior to the released state. The arrangement may be switched from the first locked stated into the released state by releasing the first locking mechanism. This may be done by the user, e.g. a patient which uses the arrangement for self-administration of a drug. The energy member may already induce a force/torque onto the transfer member in the first locked state. For example, the drive spring is already biased in the first locked state.

According to at least one embodiment, the first locking mechanism comprises a first rotation-lock element rotationally and/or axially fixed with respect to the transfer member and a second rotation-lock element rotationally and/or axially fixed with respect to the housing element. The two rotation-lock elements of the first locking mechanism may be configured to engage with each other. For example, in the first locked state, the two rotation-lock elements of the first locking mechanism are engaged with each other. The first rotation-lock element may be a part of the transfer member. The second rotation-lock element may be a part of the housing element.

According to at least one embodiment, the engagement of the rotation-lock elements of the first locking mechanism prevents a rotational movement of the transfer member. Particularly, a rotational movement in the first rotational direction or in both rotational directions is prevented in this way.

According to at least one embodiment, at least one of the rotation-lock elements of the first locking mechanism, e.g. the second rotation-lock element, is a displaceable element. For example, the displaceable rotation-lock element is displaceable in a second direction other than the first rotational direction. The second direction may be a direction perpendicular to the first rotational direction, e.g. a radial direction, particularly the outward radial direction. The other rotation-lock element of the first locking mechanism may be radially fixed. In a first position of the displaceable rotation-lock element, the rotation-lock elements of the first locking mechanism are engaged. In a second position of the displaceable rotation-lock element, the two rotation-lock elements of the first locking mechanism may be disengaged, e.g. to release the first locking mechanism and to enable rotation of the transfer member. The second position may be a position downstream along the second direction with respect to the first position.

According to at least one embodiment, the first locking mechanism is configured such that, when the displaceable rotation-lock element is in the first position, a torque or energy induced by the energy member biases the displaceable rotation-lock element in the second direction. Particularly, if the displaceable rotation-lock element is not held in the first position, i.e. in the engagement with the other rotation-lock element of the first locking mechanism, the torque or energy transferred from the energy member may result in an automatic disengagement of the two rotation-lock elements of the first locking mechanism. In other words, the rotation-lock elements of the first locking mechanism may be configured such that the torque or energy induced by the energy member onto the transfer member is at least partially converted into a force which biases the displaceable rotation-lock element in the second direction.

The first position may be the relaxed state of the displaceable rotation-lock element, i.e. the position the displaceable rotation-lock element would occupy if no external forces would act on it. Alternatively, in the second position, the displaceable rotation-lock element may be in its relaxed state and the first position may be a position in which the displaceable rotation-lock element is biased towards the second position. It is also possible that in a third position of the displaceable rotation-lock element, the third position being arranged between the first and the second position along the second direction, the displaceable rotation-lock element is in its relaxed state. In this case, in the first and second positions, the displaceable rotation-lock element may be biased in or against the second direction.

According to at least one embodiment, at least one of the rotation-lock elements of the first locking mechanism comprises a slide feature, which may abut against the other rotation-lock element and/or along which the other rotation-lock element of the first locking mechanism can slide. When the two rotation-lock elements of the first locking mechanism are engaged, the torque induced onto the transfer member by the energy member may have as a consequence that the first rotation-lock element induces a torque or force onto the second rotation-lock element. Preferably, the slide feature is configured such that this torque or force is at least partially converted into a force acting on the displaceable rotation-lock element and pointing in the second direction.

The slide feature may be a beveled surface which is tilted with respect to the second direction and with respect to the first rotational direction. For example, the angle between the beveled surface and the first rotational direction and/or the second direction is at least 10° and at most 80°. The beveled surface may be a surface at which the first and the second rotation-lock elements of the first locking mechanism abut against each other and at which the first rotation-lock element is pressed against the second rotation lock-element due to the torque.

According to at least one embodiment, the displaceable rotation-lock element of the first locking mechanism is orientated circumferentially. This means, a main extension direction of the displaceable rotation-lock element is along an angular direction. The displaceable rotation-lock element may be elongated. For example, the displaceable element may be a flexible, particularly a resilient arm. One end of the displaceable rotation-lock element may be radially, preferably also rotationally and/or axially, fixed with respect to the housing element and the end of the displaceable rotation-lock element remote from the one end, e.g. as seen along the extension of the displaceable element and/or in the angular direction, may not be radially fixed with respect to the housing element, i.e. it may be a free end, and is therefore displaceable in radial direction. The free end may face in the angular direction. In other words, the displaceable element may be pivotally connected to or integrated into the housing element, e.g. a main body thereof. The slide feature may be arranged closer to the free end than to the end fixed with respect to the housing element.

One of the first and second rotation-lock elements of the first locking mechanism may comprise a protrusion, the other one may comprise a recess. The protrusion and the recess may also be referred to as locking features. The protrusion may be configured to engage or project into the recess. The slide feature or the beveled surface may be part of the protrusion and/or the recess. The protrusion and/or the recess may be arranged closer to the free end than to the end fixed with respect to the housing element. The protrusion may be radially, e.g. radially inwardly, oriented.

According to at least one embodiment, the first and second rotation-lock elements of the first locking mechanism are configured to form an axial-lock interface when engaged with each other. The axial lock-interface prevents an axial movement, e.g. a proximal movement, of the transfer member. The axial-lock interface may act only unidirectionally or bidirectionally.

For example, the protrusion of one of the rotation-lock elements of the first locking mechanism comprises a surface running obliquely or perpendicularly to the longitudinal axis. The recess of the other one of the rotation lock elements of the first locking mechanism may likewise comprise or be delimited by a surface running obliquely or perpendicularly to the longitudinal axis. When engaged, the two surfaces abut against each other when trying to move the transfer member in an axial direction, e.g. the proximal direction.

The protrusion and/or the recess may comprise two sections, between which the surface running obliquely or perpendicularly to the longitudinal axis is formed. Thus, the protrusion may be a stepped protrusion and/or the recess may be a stepped recess.

According to at least one embodiment, the arrangement has a second locked state, in which a releasable second locking mechanism prevents an axial movement of the transfer member.

This part of the second locking mechanism preventing the axial movement is also referred to as axial-locking mechanism. Preferably, the second locking mechanism also prevents a rotational movement of the transfer member. This part of the second locking mechanism preventing the rotational movement is also referred to as second rotation-locking mechanism.

The second locked state may be a state of the arrangement during assembly of the drug delivery device and prior to the first locked state. The second locked state may be a state in which the arrangement is transported. For preparing a drug delivery process, the arrangement may be switched form the second locked state into the first locked state.

In the second locked state, the axial-locking mechanism may establish an axial-lock interface via which the transfer member and the housing element are coupled thereby preventing the axial movement of the transfer member and the second rotation-locking mechanism may establish a rotation-lock interface via which the transfer member and the housing element are coupled thereby preventing a rotational movement of the transfer member.

According to at least one embodiment, the second locking mechanism or the axial-locking mechanism thereof, respectively, comprises a first axial-lock element rotationally and axially fixed with respect to the transfer member and a second axial-lock element rotationally and axially fixed with respect to the housing element. The two axial-lock elements of the second locking mechanism may be configured to engage with each other.

According to at least one embodiment, the engagement of the axial-lock elements of the second locking mechanism prevents an axial movement, preferably also a rotational movement, of the transfer member.

The first axial-lock element of the second locking mechanism may be a part of the transfer member. The second axial-lock element of the second locking mechanism may be a part of the housing element. One of the axial-lock elements, e.g. the first axial-lock element, may be a displaceable element, e.g. displaceable in radial direction, the other axial-lock element may be radially fixed. The displaceable element may be oriented in the axial direction. The displaceable element may be a pivotable or flexible or resilient arm. The other axial-lock element, e.g. the second axial-lock element, may comprise a recess. In the second locked state, the displaceable element may project into the recess and this prevents an axial movement of the transfer member, e.g. into a position in which the first locking mechanism were established.

According to at least one embodiment, the second locking mechanism or the second rotation-locking mechanism thereof, respectively, comprises a first rotation-lock element rotationally and axially, preferably also radially, fixed with respect the transfer member and a second rotation-lock element rotationally and axially, preferably also radially, fixed with respect to the housing element. The two rotation-lock elements of the second locking mechanism may be configured to engage with each other.

According to at least one embodiment, the engagement of the two rotation-lock elements of the second locking mechanism prevents a rotational movement of the transfer member.

The first rotation-lock element of the second locking mechanism may be part of the transfer member. The first rotation-lock element of the second locking mechanism may also be the first rotation-lock element of the first locking mechanism. The second rotation-lock element of the second locking mechanism may be part of the housing element. One of the rotation-lock elements of the second locking mechanism, e.g. the second rotation-lock element, may comprise a locking feature in the form of a protrusion. The other rotation-lock element of the second locking mechanism, e.g. the first rotation-lock element, may comprise a locking feature in the form of a recess. In the second locked state, the protrusion may engage or project into the recess. The rotation-lock elements of the second locking mechanism may be configured such that, when engaged, they do not block an axial movement of the transfer member. An axial movement of the transfer member may result in a disengagement of the two rotation-lock elements of the second locking mechanism. Axial movement may be prevented by the axial-lock interface.

According to at least one embodiment, the second rotation-locking mechanism can be released by an axial movement, particularly a purely axial movement, of the transfer member. The axial movement for releasing the second rotation-locking mechanism may be a movement in proximal direction. The arrangement may be configured such that, for releasing the second rotation-locking mechanism, the displaceable axial-lock element has to be displaced such that the engagement with the other axial-lock element is released. This allows an axial movement of the transfer member and the axial movement results in a disengagement of the two rotation-lock elements of the second locking mechanism.

Preferably, the axial movement of the transfer member results in a transfer of the arrangement from the second locked state into the first locked state. The two locking mechanisms may be configured such that during the transfer from the second locked state into the first locked state, a rotational movement of the transfer member is always prevented. For example, during the axial movement, the engagement of the rotation-lock elements of the first locking mechanism is established before the rotation-lock elements of the second locking mechanism are completely disengaged.

By way of example, the locking feature of the second rotation-lock element of the first locking mechanism is arranged directly behind the locking feature of the second rotation-lock element of the second locking mechanism along an axial direction and overlapping in angular direction. In other words, the second rotation-lock elements (or the locking features thereof, respectively) of the two locking mechanisms may be angularly and/or radially aligned and axially offset from one another. At least a section of the locking feature of the second rotation-lock element of the first locking mechanism may have the same radial extension as and/or the same extension in angular direction as and/or may even be formed identically with the locking feature of the second rotation-lock element of the second rotation-locking mechanism. Said locking features may also have free ends which are radially aligned. This facilitates an engagement of the same first rotation-lock element with the two different second rotation-lock elements of both locking mechanisms.

According to at least one embodiment, in the second locked state, the transfer member is axially offset with respect to the first locked state. For example, in the second locked state, the transfer member is located downstream along the distal direction with respect to the first locked state.

According to at least one embodiment, the transfer member comprises a first portion, also called axial-lock portion, and a second portion, also called rotation-lock portion, which are axially offset. The diameter in the first portion may be greater than in the second portion. The first portion may be arranged proximally with respect to the second portion. The first rotation-lock elements of the first and second locking mechanism may be part of or may be formed by the second portion. The first axial-lock element of the second locking mechanism may be part of or may be formed by the first portion. The first and/or the second portion may be disc-shaped.

According to at least one embodiment, a third portion, also called connection portion, of the transfer member is arranged between the first portion and the second portion. The third portion may have a smaller diameter than each of the first portion and the second portion. For example, the third portion may be a shaft, e.g. with cylindrical shape. The first and/or the second and/or the third portion may, at least in the first locked state, be arranged inside the housing element, i.e. be circumferentially surrounded by the housing element. Moreover, at least in the first locked state, the plunger rod may overlap with one, some or all of the first, second and third portion of the transfer member in axial direction.

According to at least one embodiment, the arrangement is configured such that, in the released state, the transfer member moves axially with respect to the housing element until it hits an end-stop of the arrangement, e.g. a proximal end-stop. The end-stop may be formed by the housing element or by another element or member axially fixed with respect to the housing element. For example, the transfer member moves by at least 1 mm or at least 5 mm in axial direction, e.g. proximally and/or away from the second rotation-lock element of the first and/or second locking mechanism. Preferably, the transfer member moves axially and/or rotationally during the axial movement of the plunger rod.

According to at least one embodiment, in the released state and after hitting the end-stop, the transfer member continues to rotate. A further axial movement may be prevented by the end-stop. For example, after hitting the end-stop, the transfer member continues to rotate by at least 360°.

According to at least one embodiment, in the released state, the transfer member moves in proximal direction. In this case, the end-stop may be provided in the region of the proximal end of the arrangement.

According to at least one embodiment, the end-stop comprises a friction reduction element. Additionally or alternatively, the proximal end of the transfer member may comprise a friction reduction element.

According to at least one embodiment, a low friction interface is formed between the friction reduction elements of the transfer member and of the end-stop.

According to at least one embodiment, at least one of the friction reduction elements is a tapering protrusion. Particularly, the protrusion tapers in direction of the respective other friction reduction element. The protrusion may have the shape of a cone. For example, the friction reduction element of the end-stop is a tapering protrusion.

According to at least one embodiment, the other one of the friction reduction elements is an indentation. The friction reduction element being the protrusion may protrude into the indentation when the transfer member hits the end-stop. The indentation may be formed by a concave surface at the proximal end of the transfer member.

According to at least one embodiment, the indentation and/or the protrusion are rotationally symmetric, preferably circular symmetric, with respect to the rotational axis of the transfer member and/or the longitudinal axis.

According to at least one embodiment, the energy member is a drive spring, particularly a torsion drive spring, connected to the transfer member at a first connection point and connected to the housing element at a second connection point. The connection of the drive spring to the transfer member and/or the housing element is preferably irreleasable or permanent. That is to say, the connection cannot be released without destroying the connection or the connection is present in every state of the arrangement.

According to at least one embodiment, during axial movement of the transfer member, the first connection point and the second connection point are axially moved with respect to each other.

Particularly, the first connection point is moved with respect to the second connection point in proximal direction, when the transfer member moves proximally, e.g. in the released state.

Next, the drug delivery device is specified. Particularly, the drug delivery device comprises the arrangement according to any one of the described embodiments. Thus, all features described in connection with the arrangement are also disclosed for the drug delivery device and vice versa. The drug delivery device may be an auto-injector.

According to at least one embodiment, the drug delivery device comprises the arrangement according to any one of the above-described embodiments.

According to at least one embodiment, the drug delivery device comprises a housing. The housing element may be fixed to the housing or integrated in the housing. The housing is preferably axially and rotationally, preferably also radially, fixed with respect to the housing element. The housing element may be part of the housing, e.g. integrally formed with the housing, or may be a separate element. The housing may comprise or consist of plastic and/or may be formed in one piece. The housing may be hollow and/or elongated and/or hollow cylindrically-shaped. The housing may be a sleeve. The housing may be configured to hold or receive a medicament container, e.g. a syringe. The housing may be configured to hold the medicament container such that it is axially and/or rotationally and/or radially fixed with respect to the housing. The housing element and/or the energy member and/or the plunger rod and/or the transfer member may be received in the housing, i.e. circumferentially surrounded by the housing.

According to at least one embodiment, the drug delivery device comprises the medicament container. The medicament container may comprise a needle. The arrangement and the medicament container may be received in the housing, i.e. circumferentially surrounded by the housing. The needle may form the distal end of the medicament container, the medicament container may be located distally with respect to the transfer member and/or the plunger rod and/or the energy member, especially in the first locked state. The medicament container may be arranged axially and/or rotationally and/or radially fixed with respect to the housing, i.e. it is not moved with respect to the housing during the intended usage of the drug delivery device. The medicament container may be a syringe, e.g. a pre-filled syringe. An end of the container opposite the needle may be sealingly closed by a movable member, e.g. a stopper or piston. The medicament container may comprise a drug or medicament, e.g. a liquid drug or medicament. The drug delivery device may be configured to empty the medicament container when released. In other words, the medicament container may comprise medicament in an amount sufficient for just one drug delivery operation. The drug delivery operation may be performed when the drug delivery device or the arrangement, respectively, has been switched into the released state. The drug delivery device may be a single use device and/or a disposable device.

According to at least one embodiment, the drug delivery device comprises a needle shroud telescopically coupled to the housing and axially movable with respect to the housing between an extended position, e.g. a position in which the needle is covered by the needle shroud, and a retracted position, e.g. a position in which the needle is exposed. In the retracted position, the needle can be pierced into tissue of a body. The needle shroud may be rotationally fixed to the housing.

For example, in the first locked state, the needle shroud is in its extended position. An element or region of the needle shroud, e.g. a side wall of needle shroud, may hold the displaceable rotation-lock element of the first locking mechanism in its first position and may prevent the displaceable rotation-lock element from moving from the first position along the second direction. In this way, the first locking mechanism is maintained established by the needle shroud.

For example, when moving the needle shroud from its extended position to the retracted position, the needle shroud is moved in the proximal direction. The movement into the retracted position may release the first locking mechanism. By way of example, in the retracted position, the needle shroud does not longer prevent the displaceable rotation-lock element of the first locking mechanism from leaving its first position and moving in the second direction.

According to at least one embodiment, the drug delivery device comprises a shroud spring. The shroud spring may be coupled to the needle shroud and the housing and/or housing element. The shroud spring may be configured such that it induces a restoring force acting in distal direction on the needle shroud when the needle shroud is moved from the extended position towards the retracted position.

According to at least one embodiment, the medicament container comprises a stopper. The stopper may seal the medicament container in proximal direction. In the released state of the drug delivery device, a distal end of the plunger rod may abut against the stopper and may, driven by the energy member, push the stopper in distal direction. The movement of the stopper in distal direction may result in the drug in the medicament container to be pressed through the needle out of the drug delivery device.

According to at least one embodiment, in the first locked state, the plunger rod is axially spaced from the stopper. Thus, in the released state, the plunger rod first moves in distal direction before it hits the stopper and then it pushes the stopper in distal direction. The axial movement of the transfer member preferably starts simultaneously with the axial movement of the plunger rod. Alternatively, the axial movement of the transfer member may only start with or after the plunger rod hits the stopper.

According to at least one embodiment, the movement of the stopper may start with a delay compared to the start of the movement of the transfer member and/or the plunger rod. For example, the transfer member first moves in the first rotational direction and/or axially for a certain distance before the stopper starts to move.

The drug delivery device may be used as follows: First, the drug delivery device or the arrangement thereof, respectively, is in its first locked state. Then, the distal end of the drug delivery device is pressed against a skin region of a body, e.g. a human body. At this state, the distal end of the drug delivery device may be formed by a distal end of the needle shroud. This forces the needle shroud to move from the extended position into the retracted position. This movement biases the shroud spring and the biased shroud spring biases the needle shroud in distal direction with respect to the housing. In the retracted position, the first locking mechanism is released and the drug delivery device switches from the first locked state into the released state. In the released state, the drug is delivered, for example injected into the tissue of the body. Afterwards, the distal end of the drug delivery device may be removed from the skin. The shroud spring forces the needle shroud to move in distal direction, e.g. back into the extended position.

Hereinafter, the arrangement for a drug delivery device and the drug delivery device described herein will be explained in more detail with reference to drawings on the basis of exemplary embodiments. Same reference signs indicate same elements in the individual figures. However, the size ratios involved are not necessarily to scale, individual elements may rather be illustrated with an exaggerated size for a better understanding.

DETAILED DESCRIPTION

1. First Exemplary Embodiment of a Drug Delivery Device

Figure 1:
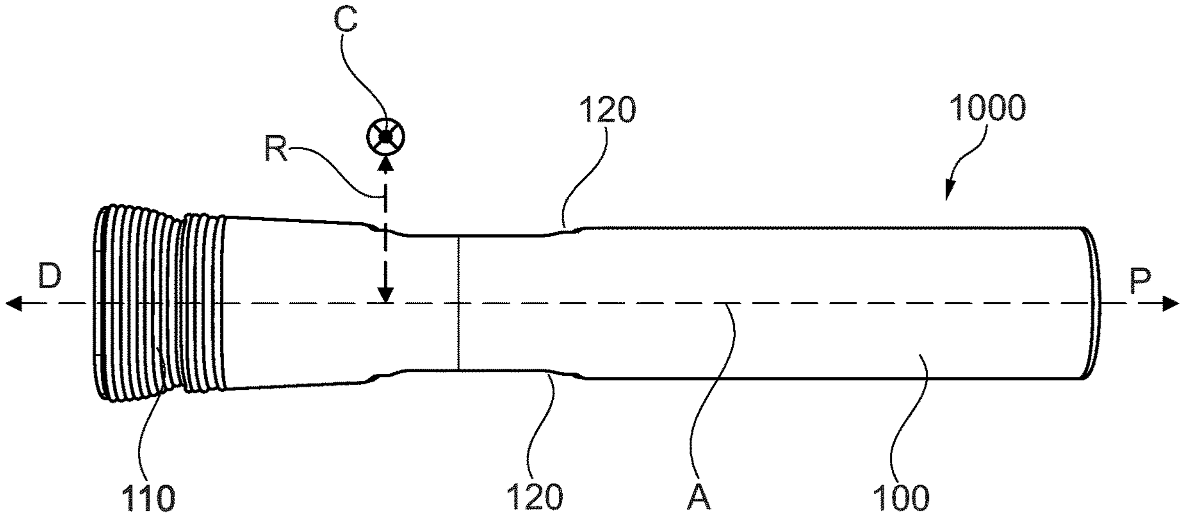
FIGS. 1 to 6 show a first exemplary embodiment of the drug delivery device in different views.
Figure 2:
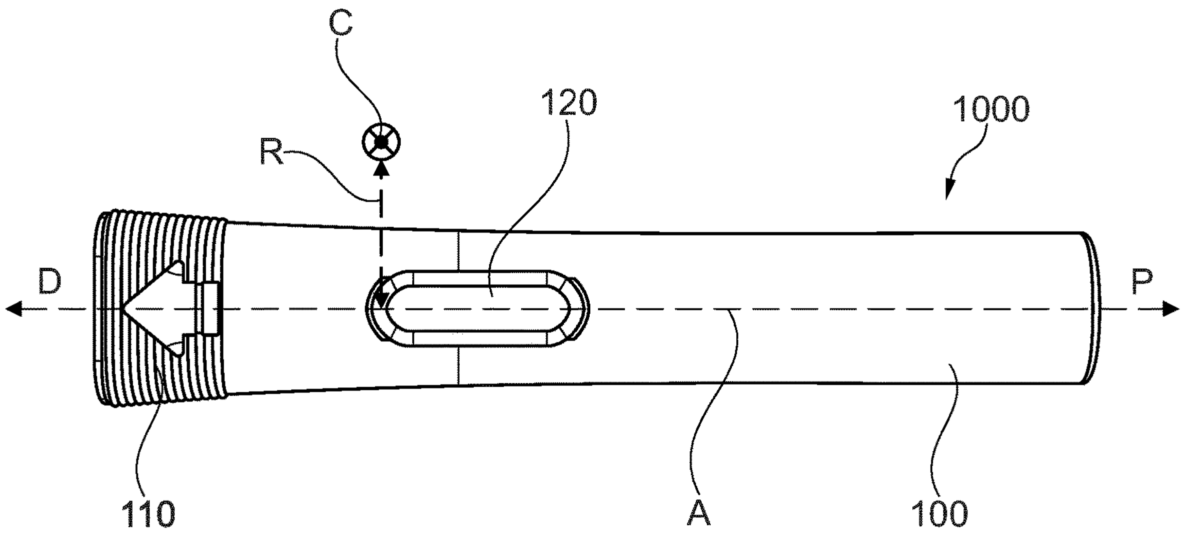

FIGS. 1 and 2 show side views of a first exemplary embodiment of the drug delivery device 1000. FIG. 1 shows a first view of the drug delivery device 1000 and FIG. 2 shows a second view in which the device 1000 is rotated by 90° around a longitudinal axis A compared to the first view.

FIGS. 1 and 2 also indicate the coordinate system used herein for specifying positions of members or elements or features. The distal direction D and proximal direction P run parallel to the longitudinal axis A. The longitudinal axis A is a main extension axis of the device 1000. The radial direction R is a direction perpendicular to the longitudinal axis A and intersecting with the longitudinal axis A. The azimuthal direction C, also referred to as angular direction or rotational direction, is a direction perpendicular to the radial direction R and to the longitudinal axis A. The different directions and axes will not be indicated in every of the following figures in order to increase the clarity of the figures.

The drug delivery device 1000 according to the first exemplary embodiment is an auto-injector. The auto-injector 1000 comprises a housing 100. A cap 110 is removably attached or coupled to the housing 100 at a distal end of the housing 100. The housing 100 may be formed in one piece and may extend from the cap 110 to the proximal end of the auto-injector 1000. The housing 100 is a cylindrically-shaped sleeve.

As can be further seen in FIGS. 1 and 2, the housing 100 comprises windows 120 through which a medicament container inside the housing 100 can be investigated. For example, the fill level of the drug inside the medicament container or the advancement of a stopper in the medicament container or the drug clarity or the degradation of the drug can be observed through the windows 120.

Figure 3:
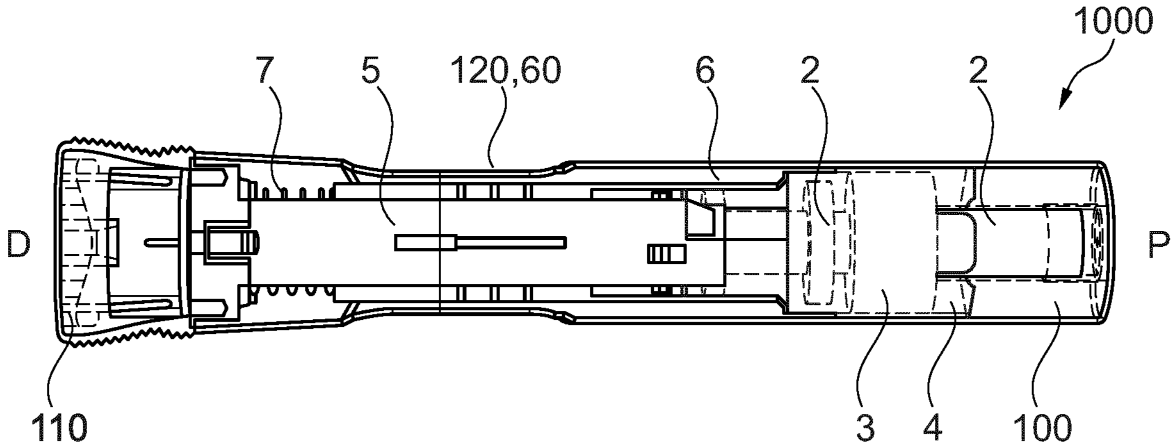
Figure 4:
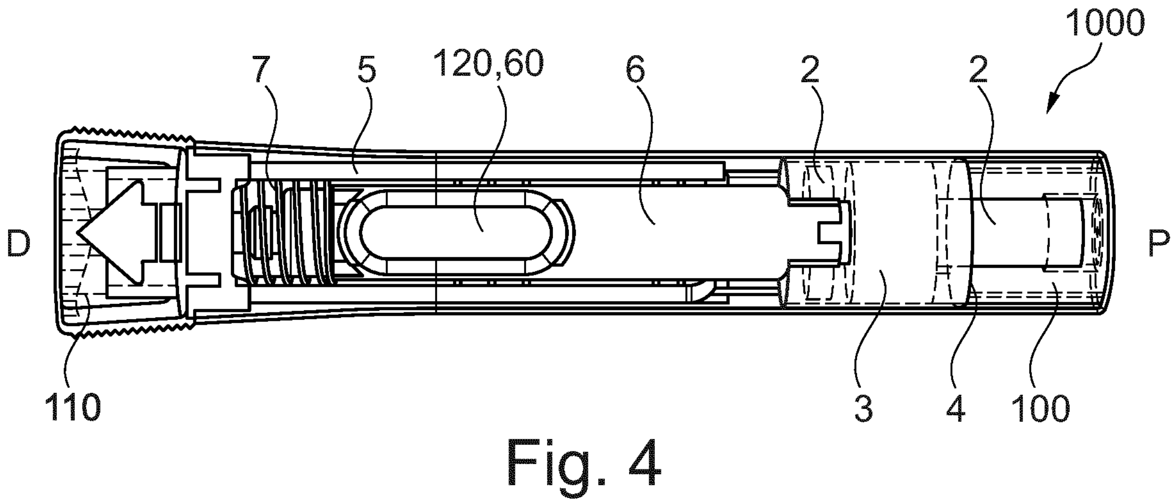

FIGS. 3 and 4 show the auto-injector 1000 in the same views as in FIGS. 1 and 2, but now the cap 110 and the housing 100 are indicated semi-transparent so that further details of the auto-injector 1000, which are normally completely surrounded and hidden by the housing 100 and the cap 110, are visible. It can be seen that the auto-injector 1000 further comprises a transfer member 2, also referred to as moveable member 2 or drive member 2, respectively, in the form of a rotating collar 2, an energy member 3 in the form of a torsion drive spring 3, particularly a spiral torsion drive spring (also commonly referred to as clock spring or power spring), and a housing element 4 in the form of a drive spring holder 4.

The drive spring holder 4 is fixed to the housing 100 so that the drive spring holder 4 can neither be rotated nor axially nor radially moved with respect to the housing 100. For example, the drive spring holder 4 is fixed with help of clips (not shown) to the housing 100. Alternatively, the drive spring holder 4 may be part of the housing 100, e.g. integrally formed with the housing 100. The drive spring holder 4 is received in the housing 100. The housing 100 circumferentially completely surrounds the drive spring holder 4.

The torsion drive spring 3 is connected to the drive spring holder 4 at a connection point. At a further connection point, the torsion drive spring 3 is connected to the rotating collar 2. The rotating collar 2 is arranged axially and rotationally movable with respect to the drive spring holder 4. The torsion drive spring 3 circumferentially surrounds a portion of the rotating collar 2. When the torsion drive spring 3 is biased, it induces a torque onto the rotating collar 2. This torque results in a rotation of the rotating collar 2 with respect to the drive spring holder 4, if the rotating collar 2 is not prevented from rotating by a locking mechanism (see explanations further down below). The rotational axis of the rotating collar 2 may define or coincide with the longitudinal axis A.

The auto-injector 1000 further comprises a release member 5 or protection member 5, respectively, in the form of a needle shroud 5 and a medicament container holder 6 in the form of a syringe holder 6. The syringe holder 6 may be axially and preferably also rotationally fixed with respect to the housing 100. The syringe holder 6 is configured to hold a syringe. The syringe holder 6 comprises windows 60 which overlap/are aligned with the windows 120 in the housing 100. In this way, the syringe or medicament container can be observed through the windows 60, 120.

The needle shroud 5 is arranged axially movable with respect to and telescopically coupled to the housing 100 or the drive spring holder 4, respectively. Particularly, the needle shroud 5 can be moved from an extended position, which is the position shown in FIGS. 3 and 4, in the proximal direction P, into a retracted position (see FIGS. 7 and 8). This will be explained in more detail further below.

The needle shroud 5 and the syringe holder 6 are moveably coupled to each other via a shroud spring 7. One end of the shroud spring 7 is connected to the syringe holder 6 and the other end of the shroud spring 7 is connected to the needle shroud 5. The coupling is such that a movement of the needle shroud 5 in the proximal direction P with respect to the syringe holder 6 results in a compression of the shroud spring 7 inducing a force onto the needle shroud 5 pointing in distal direction D.

Figure 5:
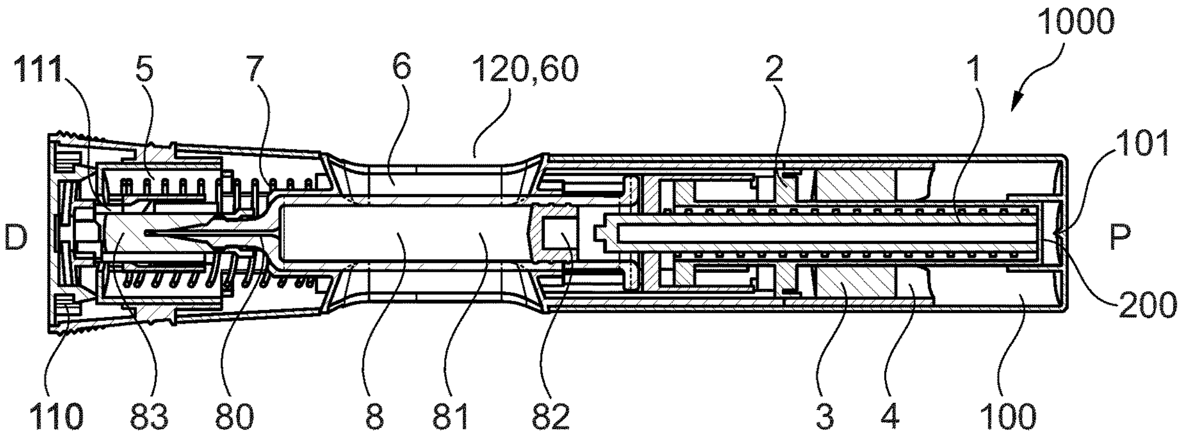
Figure 6:
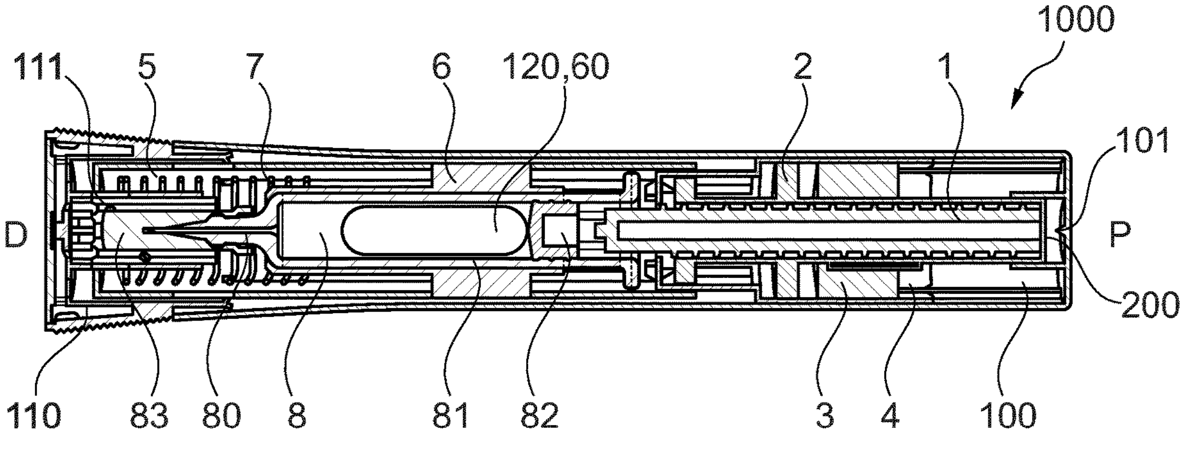

FIGS. 5 and 6 show the auto-injector 1000 in two cross-sectional views, the views again being rotated by 90° with respect to each other around the longitudinal axis. The cutting plane comprises the longitudinal axis A. In this view, it can be seen that the auto-injector 1000 further comprises a plunger rod 1. The plunger rod 1 is arranged inside the rotating collar 2 and is circumferentially surrounded by the rotating collar 2. Only a small portion of the plunger rod 1 (less than 50% of its length) projects out of the rotating collar 2 in distal direction D. In proximal direction P, the rotating collar 2 is closed and the plunger rod 1 does not project beyond the proximal end of the rotating collar 2. The plunger rod 1 is longer, measured along the longitudinal axis A, than the rotating collar 2.

The housing 100, the housing element 4, the plunger rod 1, the rotating collar 2, the needle shroud 5, the syringe holder 6 and the cap 110 may all comprise or consist of plastic. All these members may each be formed in one piece. The drive spring 3 and the shroud spring 7 may comprise or consist of a metal, e.g. steel.

It can be seen in FIGS. 5 and 6 that a medicament container 8, in the present case a syringe 8, is arranged in the syringe holder 6. This syringe 8 may be arranged axially and/or rotationally and/or radially fixed with respect to the syringe holder 6 and/or with respect to the housing 100. The syringe 8 comprises a cartridge 81 filled with a drug, a needle 80 and a stopper 82. The needle 80 is arranged at a distal end of the syringe 8. The stopper 82 seals the cartridge 81 in proximal direction P. When moving the stopper 82 in the distal direction D, the drug stored in the cartridge 81 is pressed out of the syringe 8 through the needle 80.

In FIGS. 5 and 6 it can be further seen that the needle 80 is covered by a needle shield 83 which encapsulates the needle 80 and projects beyond the needle 80 in distal direction D. The needle shield 83 may be formed of a rubber material. The cap 110 is connected to a grabber 111. The grabber 111 is retained within the cap 110 with a one or more bosses. The grabber 111 is coupled with the needle shield 83. The grabber 111 may be formed of a metal and may comprise barbs, which engage into the material of the needle shield 83.

When the cap 110 is removed from the housing 100, the grabber 111 pulls of the needle shield 83 from the needle 80. Afterwards, the needle 80 is circumferentially only surrounded by the retractable needle shroud 5.

Figure 7:
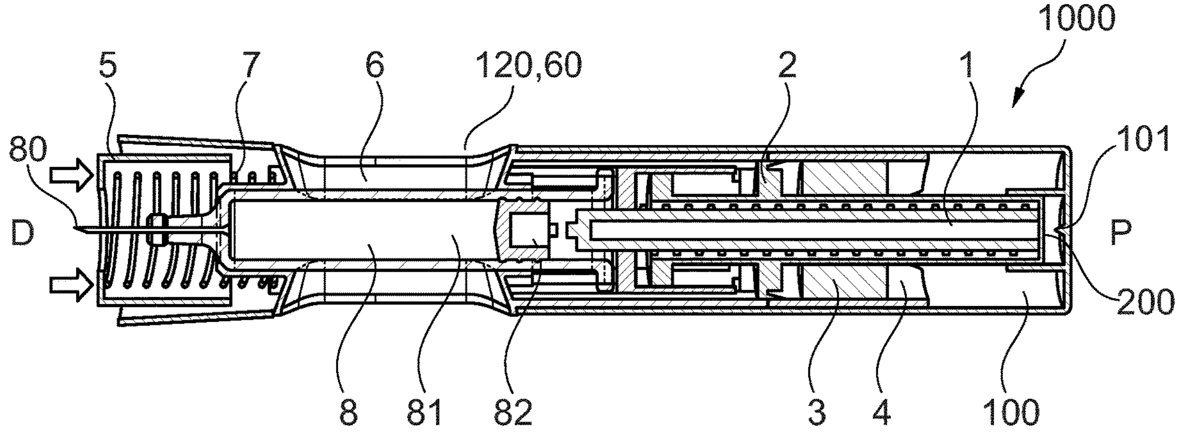
FIGS. 7 to 12 show different positions during usage of the drug delivery device according to the first exemplary embodiment.
Figure 8:
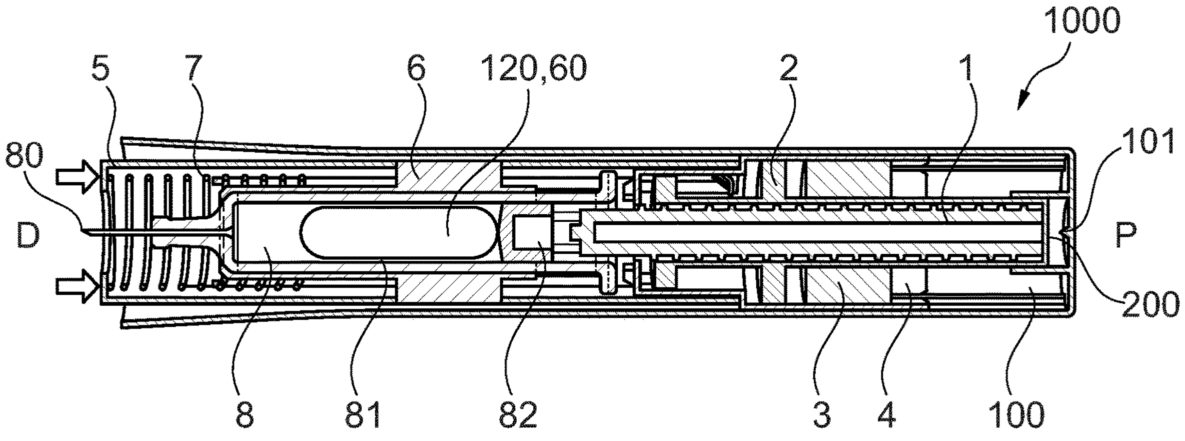

FIGS. 7 and 8 show the auto-injector 1000 in the two cross-sectional views during usage. A first position during usage is shown in which the cap 110, the grabber 111 and the needle shield 83 have been removed from the housing 100. The needle shroud 5 projects from the housing 100 in distal direction D.

In the position of FIGS. 7 and 8, the distal end of the auto-injector 1000 formed by the needle shroud 5 may be pressed against a body, e.g. a human body. As a consequence of that, the needle shroud 5 moves from its extended position in the proximal direction P with respect to the housing 100. This results in the needle 80 being exposed and projecting in distal direction D beyond the needle shroud 5 so that it can now pierce or is already pierced into the tissue of the body.

In the position of FIGS. 7 and 8, the auto-injector 1000 is still in a first locked state, also referred to as pre-released state or initial state, (like in the previous figures), in which the torsion drive spring 3 is biased and induces a torque onto the rotating collar 2. A first locking mechanism (also referred to as first rotation-locking mechanism), however, prevents the rotating collar 2 from a rotational movement. The first locking mechanism will be explained in more detail further below.

In the first locked state, a proximal end of the rotating collar 2 is axially spaced from a proximal end-stop of the housing 100. This allows an axial movement of the rotating collar 2 in proximal direction P. Moreover, in the first locked state, a distal end of the plunger rod 1 is axially spaced from the stopper 82 of the syringe 8. Thus, the plunger rod 1 can axially move in the distal direction D for a predetermined distance before hitting the stopper 82.

Figure 9:
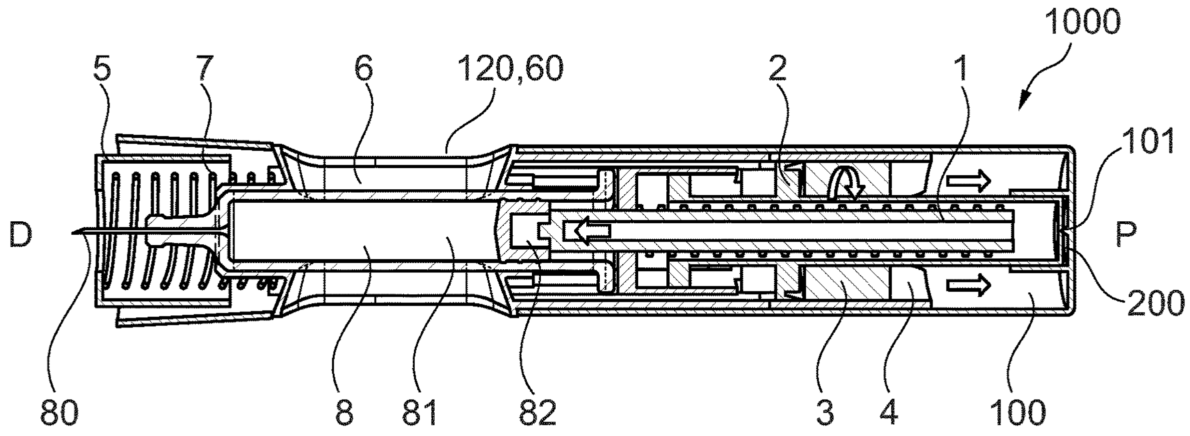
Figure 10:
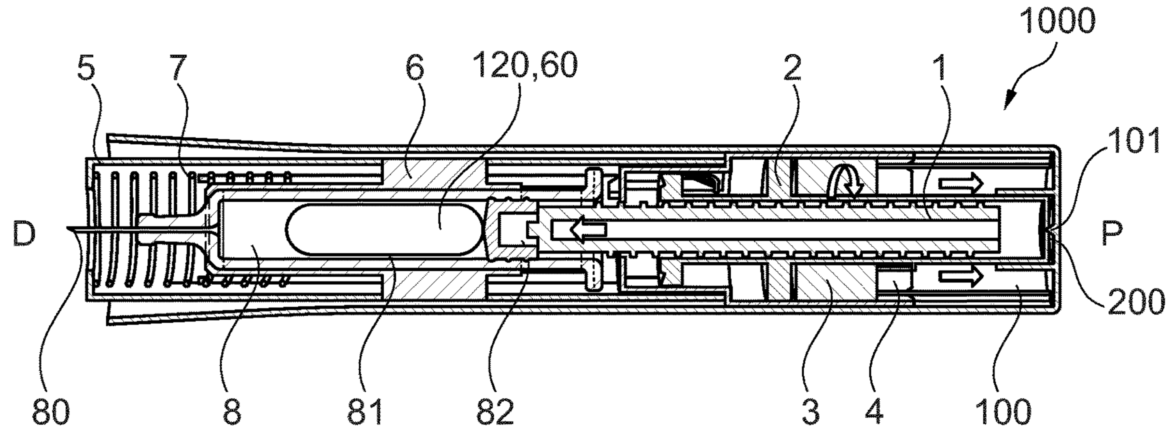

FIGS. 9 and 10 show the two cross-sectional views of the auto-injector 1000 in a second position during usage. The auto-injector 1000 is now in a released state. The needle shroud 5 has been further moved in the proximal direction P into a retracted position. This has released the first locking mechanism so that the rotating collar 2 was no longer prevented from rotating. The torque induced by the torsion drive spring 3 onto the rotating collar 2 forces the rotating collar 2 to rotate in a first rotational direction (clockwise or counterclockwise). A drive mechanism, which will be explained in more detail further below, has converted the rotation of the rotating collar 2 into an axial movement of the plunger rod 1 in the distal direction D. After having moved the predetermined distance in the distal direction D, the plunger rod 1 has hit the stopper 82 of the syringe 8 and can now push the stopper 82 in distal direction D which results in the drug in the cartridge 81 being pressed out through the needle 80 into the tissue.

As indicated in FIGS. 9 and 10, the rotating collar 2 does not only rotate but also moves in proximal direction P until the proximal end of the rotating collar 2 hits the proximal end-stop of the housing 100. The end-stop comprises is a protrusion 101 which tapers in distal direction D. The protrusion 101 may be a cone. The proximal end of the rotating collar 2 comprises an indentation 200. For example, the surface of the proximal end of the rotating collar 2 is concavely shaped. The protrusion 101 can penetrate into the indentation 200 when the proximal end of the rotating collar 2 hits the end-stop of the housing 100. The protrusion 101 and the indentation 200 may each be designed rotationally symmetric or circular symmetric with respect to the rotational axis of the rotating collar 2. In this way, a low friction interface is formed between the housing 100 and the rotating collar 2 so that a low friction rotation of the rotating collar 2 is enabled also when the proximal end of the rotating collar 2 abuts against the housing 100. Particularly, the radius at which the friction between the rotating collar 2 and the end-stop acts is approaching zero or is zero, therefore the resulting torque from the friction also tends to zero significantly reducing losses allowing a reduced spring force and/or enhance injection performance.

Figure 11:
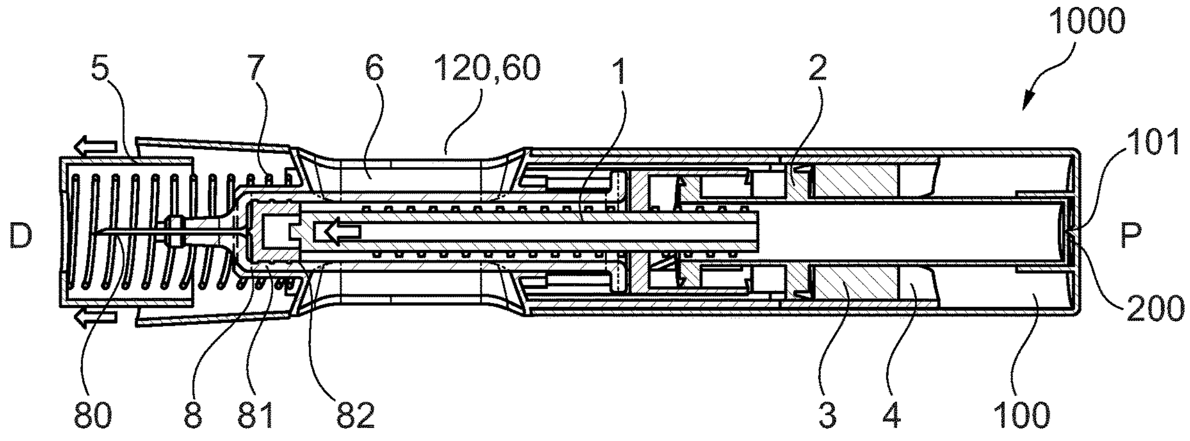
Figure 12:
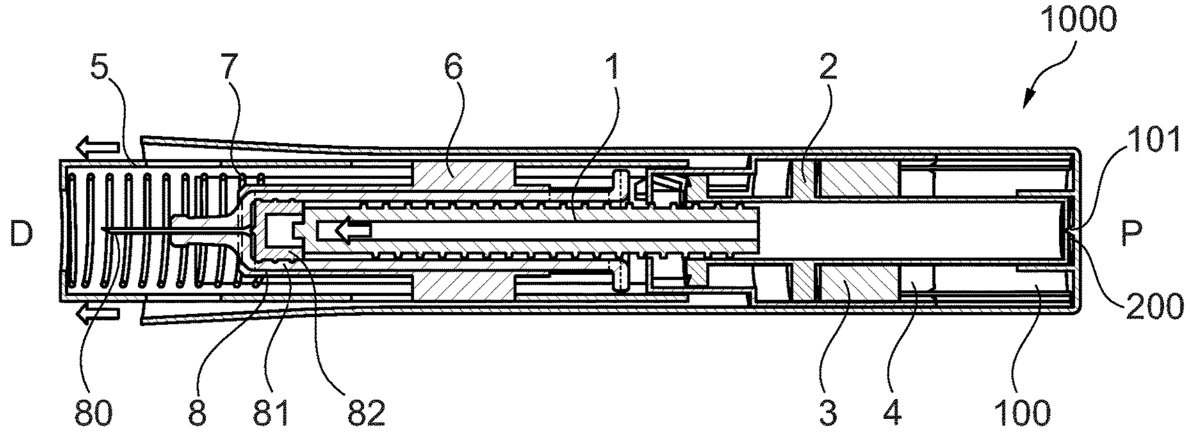

FIGS. 11 and 12 show two cross-sectional views of the auto-injector 1000 in a third position during usage. The torsion drive spring 3 has further induced torque onto the rotating collar 2, which, although abutting against the end-stop of the housing 100, has further rotated and has thereby forced the plunger rod 1 to move further in distal direction D. The plunger rod 1 has pushed the stopper 82 further in distal direction D so that a predetermined dose of the drug was supplied through the needle 80, e.g. into the tissue. Between the described first and third position, the rotating collar 2 has, e.g., rotated several times around its rotational axis.

In FIGS. 11 and 12, the auto-injector 1000 is in a third locked state or post-released state, in which the needle shroud 5 is again in its extended position so that it circumferentially surrounds the needle 80 and so that the needle 80 does no longer distally project beyond the needle shroud 5. The movement of the needle shroud 5 in the extended position happens automatically due to the force induced by the shroud spring 7 which has been compressed when moving the needle shroud 5 out of the extended position towards the retracted position.

In the third locked state of the auto-injector 1000 shown in FIGS. 11 and 12, the needle shroud cannot be moved back into the retracted position due to a third locking mechanism which will be explained in more detail further below.

Figure 13:
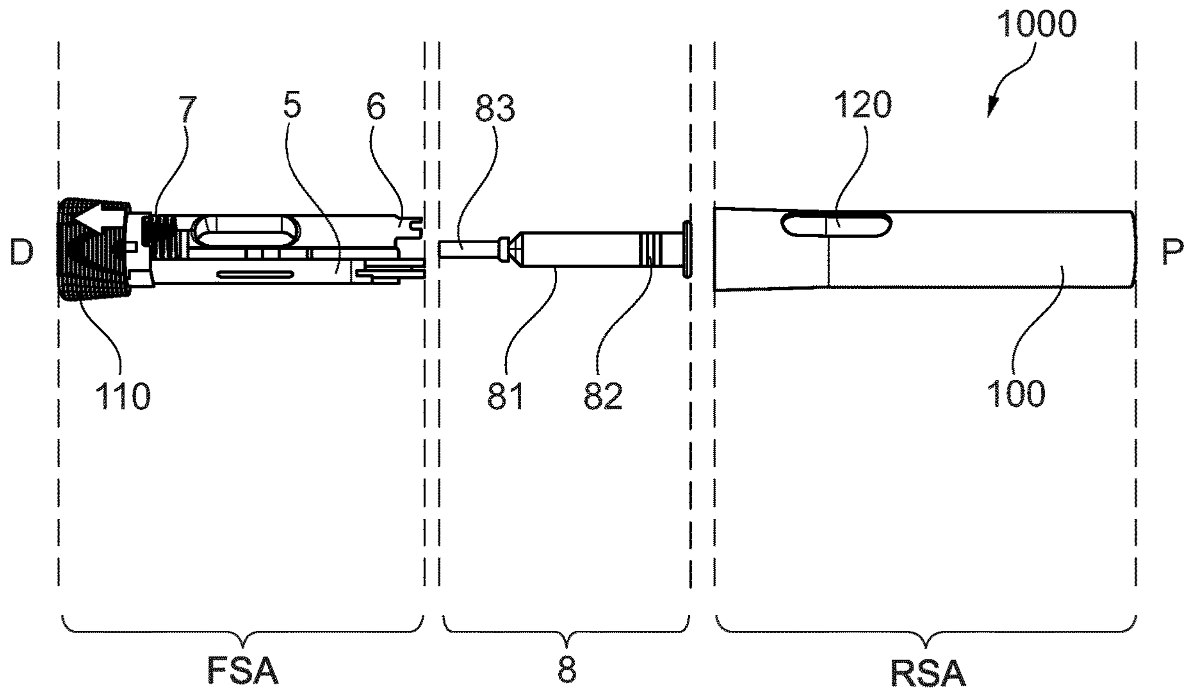
FIG. 13 shows the drug delivery device according to the first exemplary embodiment in an exploded view.

FIG. 13 shows the auto-injector 1000 of the previous figures in an exploded view. The auto-injector 1000 comprises a release subassembly FSA or front subassembly FSA, respectively, a drive subassembly RSA or rear subassembly RSA, respectively, and the syringe 8. For assembling the auto-injector 1000, the syringe 8 is inserted into the front subassembly FSA or the rear subassembly RSA and afterwards the front subassembly FSA is inserted into the rear subassembly RSA. Assembling of the auto-injector 1000 will be explained in more detail further below.

Figure 14:
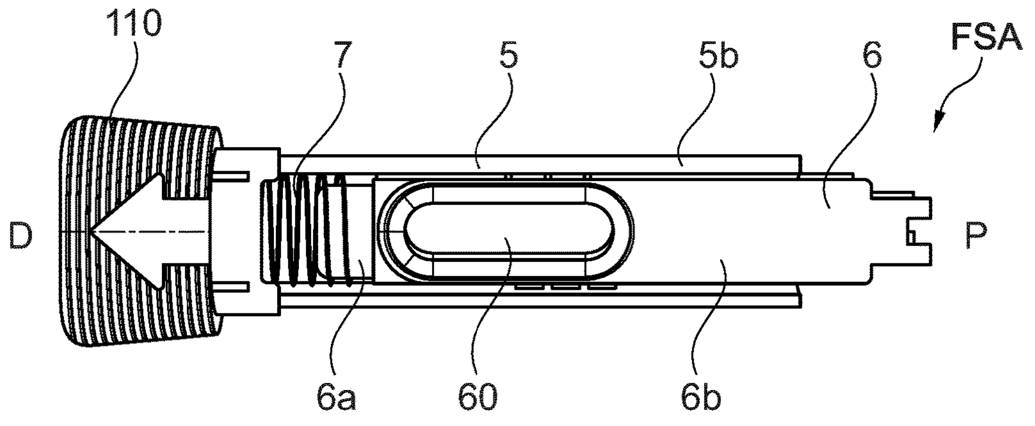
FIGS. 14 to 16 show subassemblies of the drug delivery device according to the first exemplary embodiment in more detail.

FIG. 14 shows the front subassembly FSA in a more detailed side view. The syringe holder 6 comprises two elongated arms **6*b* which extend axially and which are spaced from one another along the angular direction. The needle shroud 5 also comprises two elongated arms 5*b* which extend axially and which are spaced from one another along the angular direction. The needle shroud 5 and the syringe holder 6 are inserted into each other such that the arms 5*b* of the needle shroud 5 are located between the arms 6*b* of the syringe holder 6 along the angular direction. Furthermore, it can be seen that the arms 6*b* of the syringe holder 6 project beyond the arms 5*b* of the needle shroud 5** in proximal direction P.

The distal end of the syringe holder 6 is formed by a distal portion **6*a* in the form of a cylindrically-shaped portion 6*a*. This portion 6*a* is configured to hold the shroud spring 7. The cylindrically-shaped portion 6*a* is inserted into the shroud spring 7 so that an edge of the syringe holder 6 abuts against the proximal end of the shroud spring 7. The shroud spring 7 circumferentially surrounds the cylindrically-shaped portion 6*a* of the syringe holder 6. The shroud spring 7 may be fixed to the cylindrically-shaped portion 6*a*, e.g. by a glue or a mechanical radial interference with the proximal coil of the shroud spring 7**.

Figure 15:
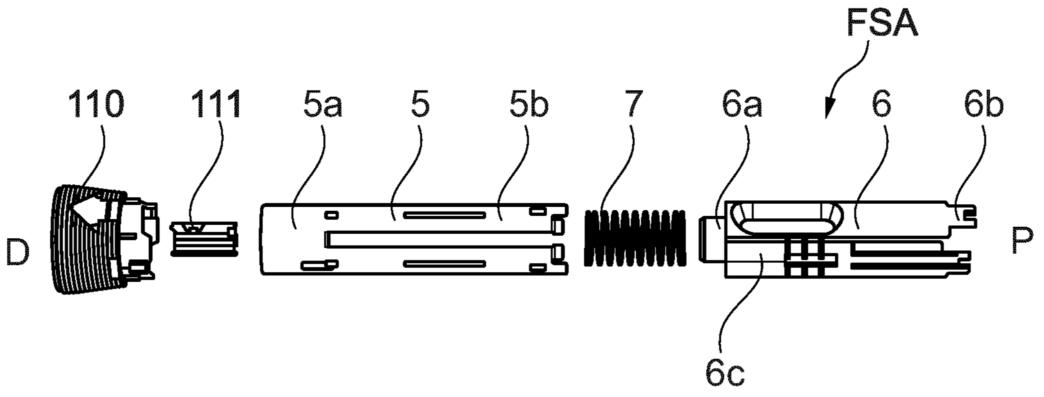

FIG. 15 shows the front subassembly FSA in an exploded view. It comprises the cap 110, the grabber 111, the needle shroud 5, the shroud spring 7 and the syringe holder 6. The needle shroud 5 also comprises a distal portion **5*a* in the form of a cylindrically-shaped portion 5*a* forming the distal end of the needle shroud 5. The cylindrically-shaped portion 5*a* is configured to hold the shroud spring 7. This cylindrically-shaped portion 5*a* is shaped as a hollow cylinder so that the shroud spring 7 can be inserted into this portion 5*a* and so that the distal end of the shroud spring 7 abuts against a bottom area of the cylindrically-shaped portion 5*a*. The shroud spring 7 may be fixed to the cylindrically-shaped portion 5*a*, e.g. by a glue or a mechanical radial interference with the distal coil of the shroud spring 7. In this way, the needle shroud 5, the shroud spring 7 and the syringe holder 6 are coupled such that a movement of the needle shroud 5 in proximal direction P with respect to the syringe holder 6 results in a compression of the shroud spring 7. The shroud spring 7 could also be held in place by a coupling/snap between the needle shroud 5 and the syringe holder 6 at the most extended positions, e.g. by the features 54 and 61** explained further below.

As can further be seen in FIG. 15, the syringe holder 6 comprises a support portion **6*c*, which is located proximally with respect to the cylindrically shaped portion 6*a* and which is located between the arms 6*b* and the cylindrically shaped portion 6*a*. After inserting the syringe holder 6 into the needle shroud 5, the arms 5*b* of the needle shroud 5 cover the support portion 6*c*, i.e. are located radially outwardly with respect to the support portion 6*c***.

Figure 16:
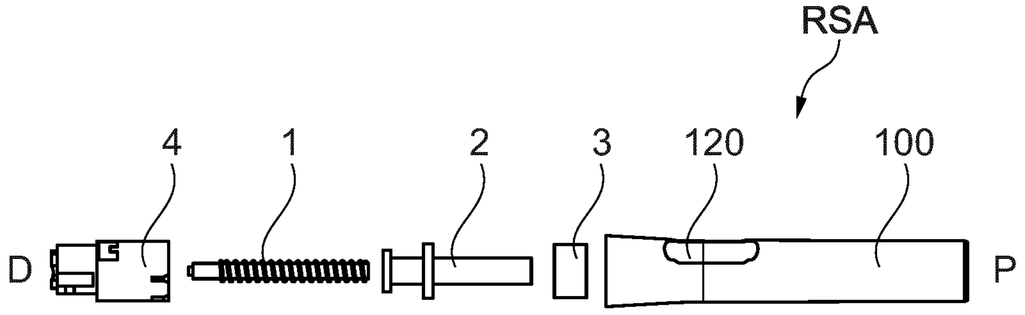

FIG. 16 shows the rear subassembly RSA in an exploded view. The rear subassembly RSA comprises the housing 100, the torsion drive spring 3, the rotating collar 2, the plunger rod 1 and the drive spring holder 4. The drive spring holder 4, the rotating collar 2 and the housing 100 each have the form of a sleeve. When assembling the rear subassembly RSA, the plunger rod 1 is inserted into the rotating collar 2, the rotating collar 2 is inserted into the torsion drive spring 3 and is fixed to the torsion drive spring 3 at one connection point. The torsion drive spring 3 is inserted into the drive spring holder 4 and is connected to the drive spring holder 4 at a further connection point. The drive spring holder 4 is inserted into the housing 100.

2. Second Exemplary Embodiment of a Drug Delivery Device

Figure 17:
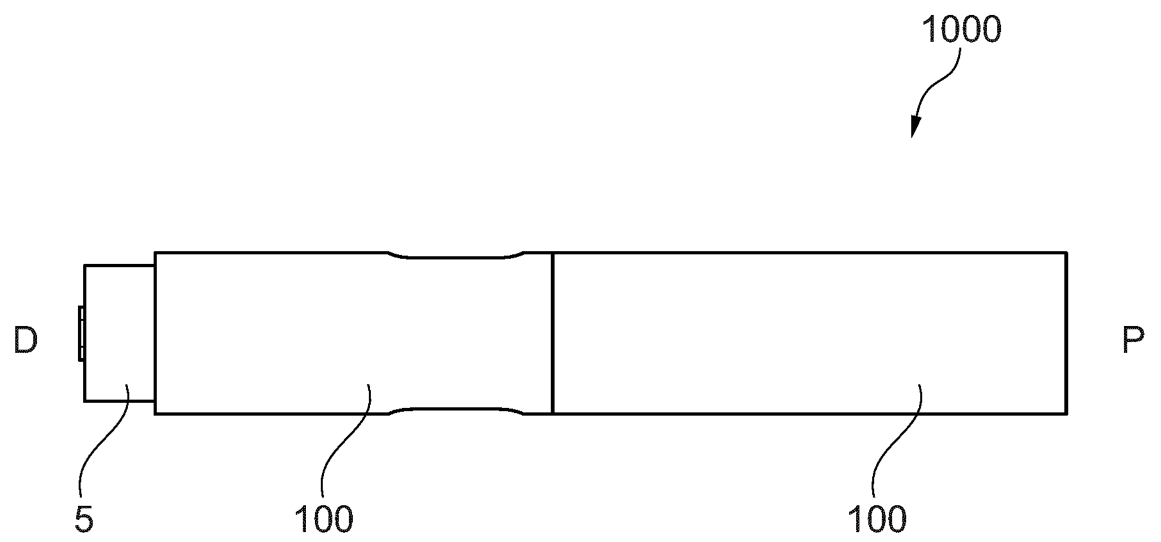
FIGS. 17 to 22 show a second exemplary embodiment of the drug delivery device in different views.
Figure 18:
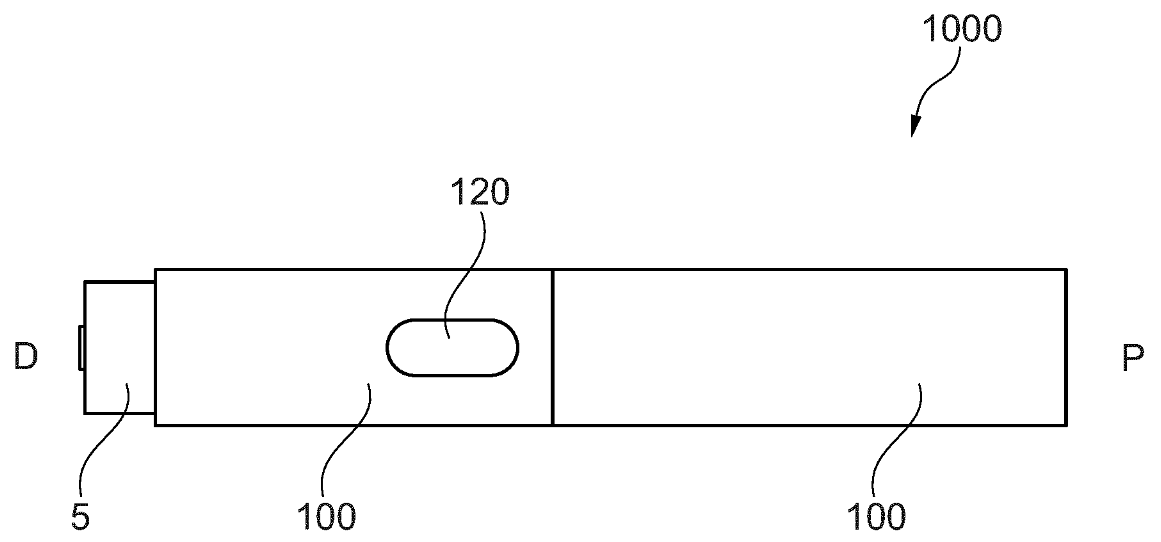

FIGS. 17 and 18 show a second exemplary embodiment of a drug delivery device 1000 which is again an auto-injector 1000. Like FIGS. 1 and 2, FIGS. 17 and 18 show the auto-injector 1000 in two different views rotated with respect to each other by 90° around the longitudinal axis A.

Figure 19:
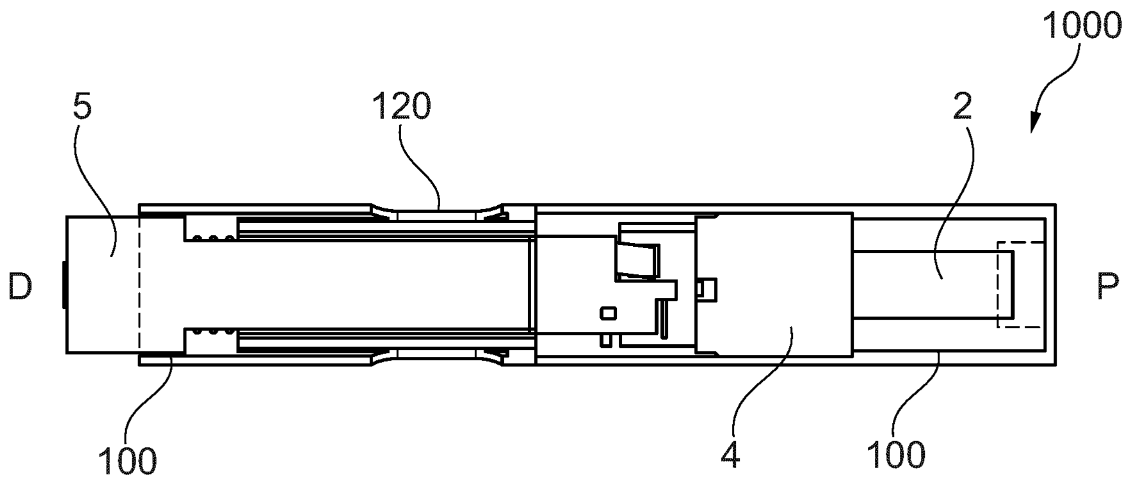
Figure 20:
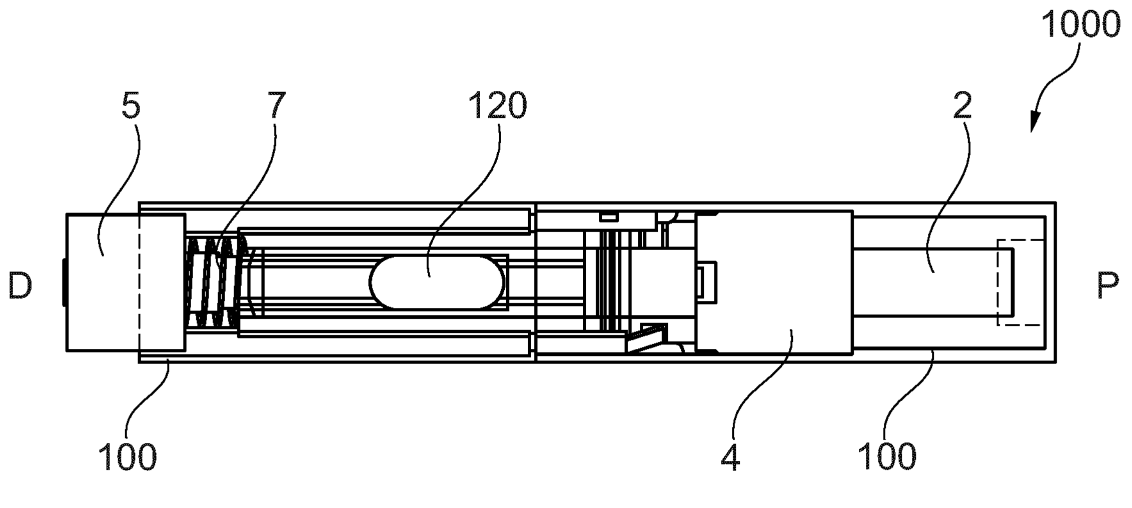

FIGS. 19 and 20 show the auto-injector 1000 of FIGS. 17 and 18 in the same rotated views but with a semi-transparent housing 100.

Figure 21:
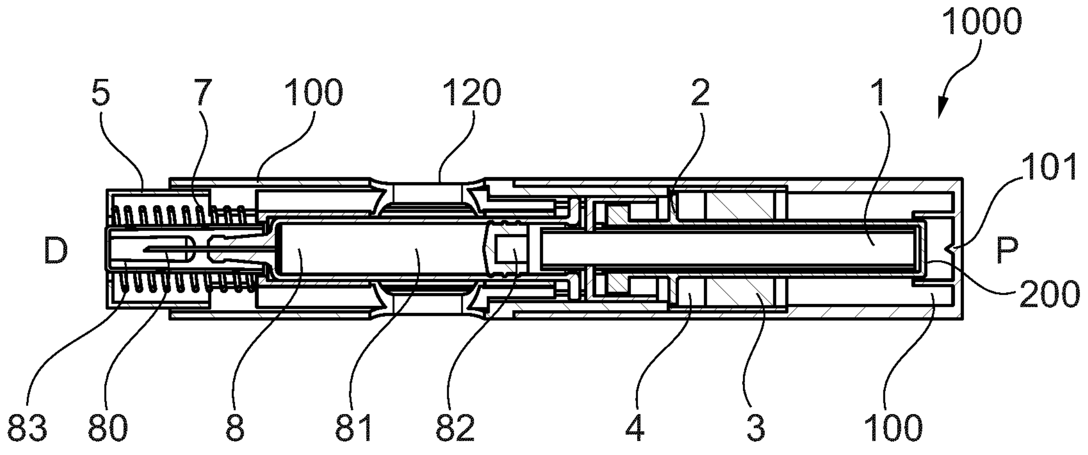
Figure 22:
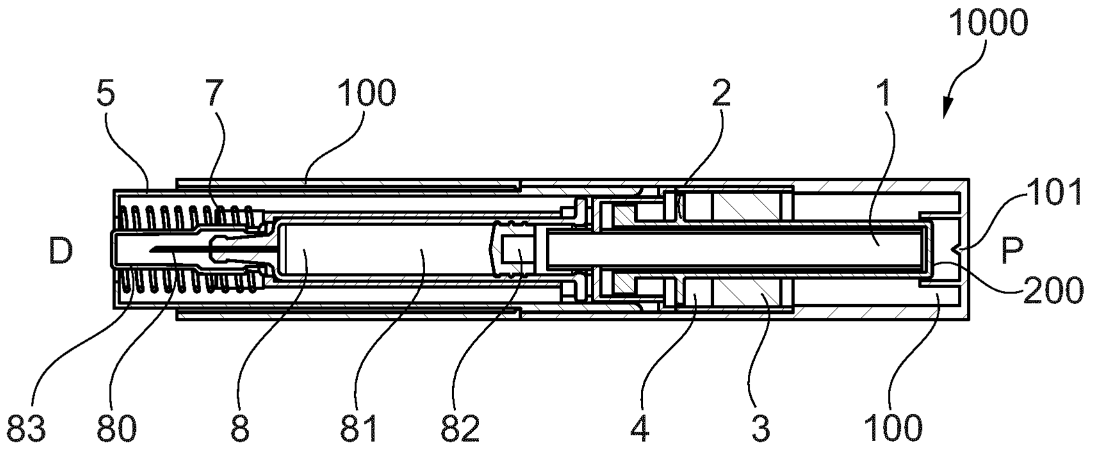

FIGS. 21 and 22 show the auto-injector 1000 of FIGS. 17 and 18 in the same rotated views but now in cross-sectional view with the crossing plane comprising the longitudinal axis.

One difference between the auto-injector 1000 according to the second exemplary embodiment and the auto-injector according to the first exemplary embodiment is that, in the second exemplary embodiment, the housing 100 now comprises two parts instead of one part. A first part forming the distal part of the housing 100 and a second part forming the proximal part of the housing 100. The two parts of the housing 100 are connected to each other, e.g. with help of clips (not shown). For example, the two parts of the housing 100 are fixed to each other such that they are neither axially nor rotationally nor radially movable with respect to each other.

Figure 23:
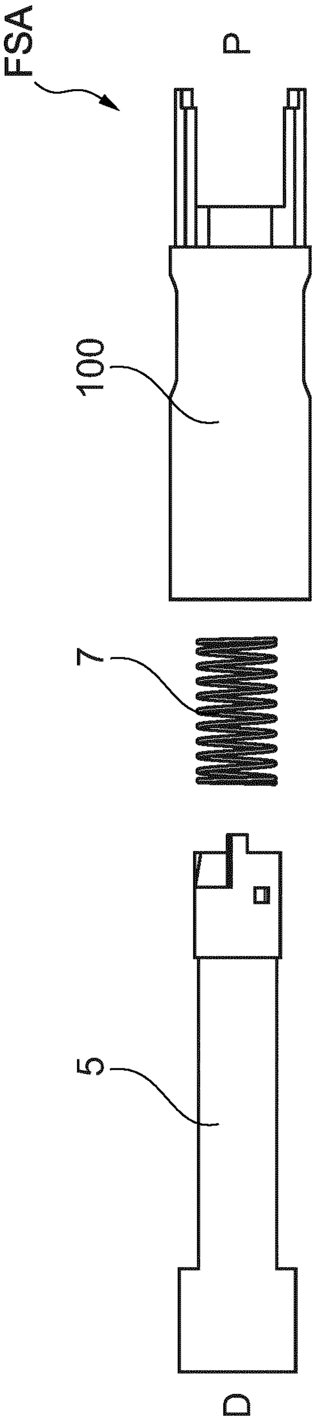
FIGS. 23 and 24 show subassemblies of the drug delivery device according to the second exemplary embodiment in exploded views.

FIG. 23 shows a front subassembly FSA of the auto-injector 1000 according to the second exemplary embodiment in an exploded view. The first part of the housing 100 is assigned to the front subassembly FSA. The needle shroud 5 may be inserted into this first part of the housing 100. The shroud spring 7 is connected to the needle shroud 5 and the first part of the housing 100 so that a movement of the needle shroud 5 in proximal direction with respect to the first part of the housing 100 results in a compression of the shroud spring 7. In difference to the first exemplary embodiment, the auto-injector according to the second exemplary embodiment does not comprise a syringe holder with two arms spaced in angular direction. Instead of such a syringe holder, the first part of the housing 100 is configured to hold a medicament container, e.g. in an axially and/or rotationally fixed manner. The first part of the housing 100 circumferentially completely surrounds the needle shroud 5.

Figure 24:
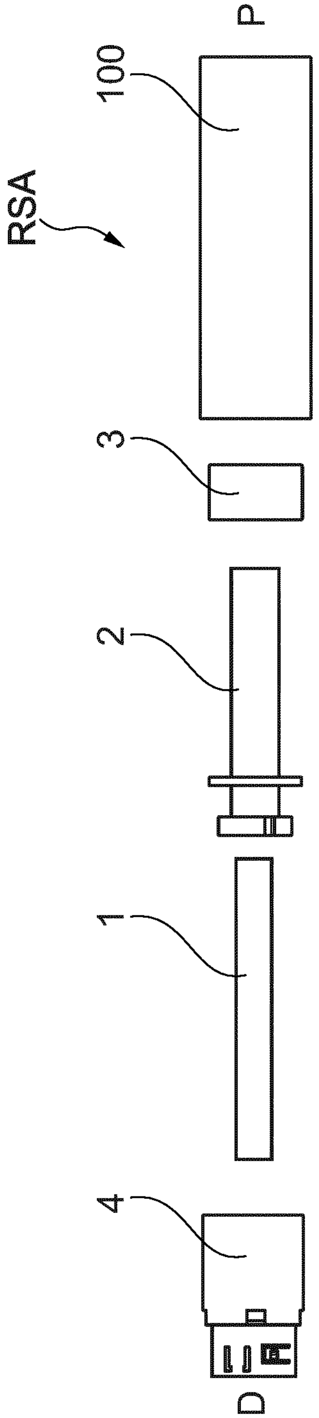

An exploded view of the rear subassembly RSA of the auto-injector 1000 according to the second exemplary embodiment is shown in FIG. 24. This rear subassembly is substantially identical to the rear subassembly RSA of the first exemplary embodiment. The second part of the housing 100 assigned to the rear subassembly RSA may be shorter than the housing 100 of the first exemplary embodiment.

3. Drive Mechanism

The conversion of the rotational movement of the rotating collar 2, induced by the torsion drive spring 3, into an axial movement of the plunger rod 1 (drive mechanism) is explained in more detail in the following in connection with FIGS. 25 to 27.

Figure 25:
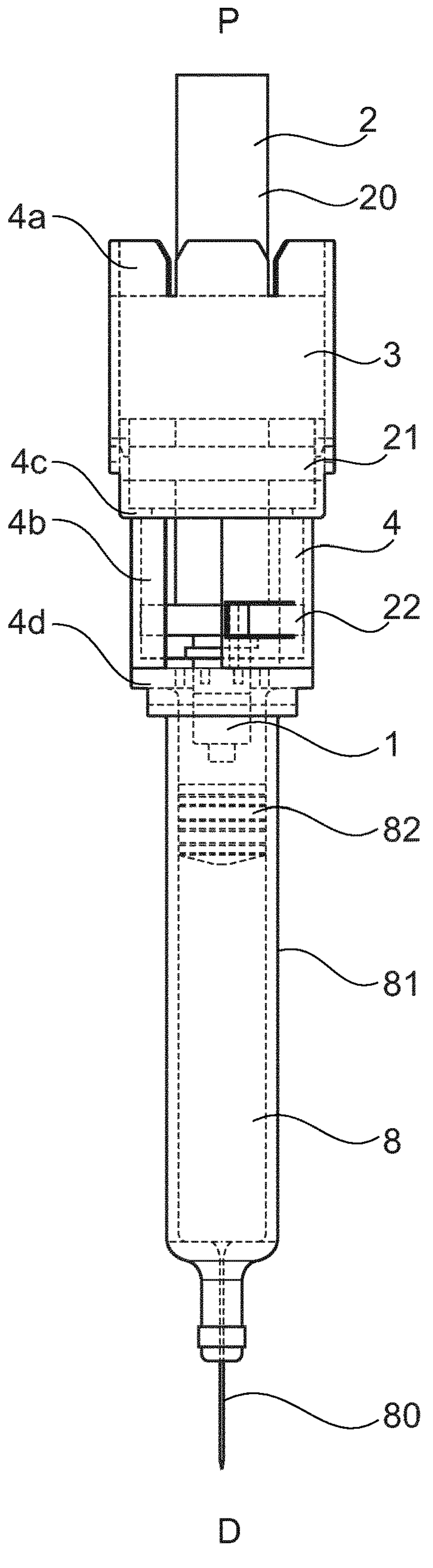
FIGS. 25 to 27 show a part or arrangement of the drug delivery device according to the first and second exemplary embodiment in different positions during usage for illustrating an exemplary embodiment of a drive mechanism.
Figure 26:
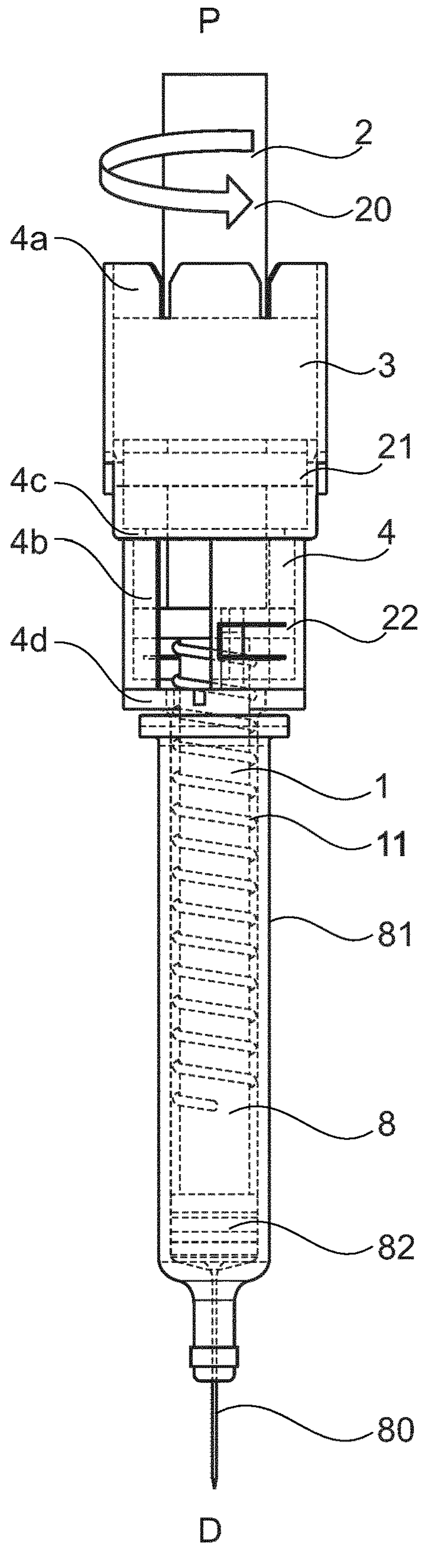
Figure 27:
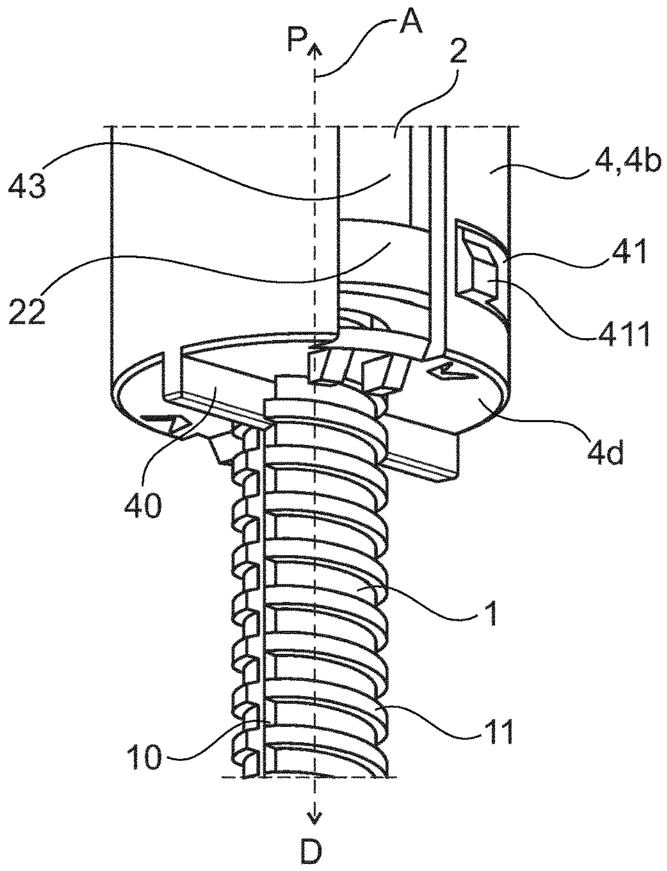

FIGS. 25 and 26 show a part or arrangement of the auto-injector 1000 of the first and second exemplary embodiment in different positions during usage. The shown part comprises the rear subassembly (the housing is not shown) and a syringe 8. In FIG. 25, the auto-injector 1000 is in the first locked state and in FIG. 26 the auto-injector is in the released state.

As can be seen in FIGS. 25 and 26, the drive spring holder 4 comprises two hollow sections 4*a*, 4*b*, which may both be hollow cylindrically-shaped. The two sections 4*a*, 4*b* are arranged behind each other along the longitudinal axis. The first section 4*a* is located more proximally and has a greater inner diameter and a greater outer diameter than the second section 4*b*.

The rotating collar 2 is received in the drive spring holder 4. A proximal end of the rotating collar 2 projects out of the drive spring holder 4 in proximal direction P. The rotating collar 2 comprises a shaft 20, and two portions 21, 22 with larger diameters than the shaft 20. The two portions 21, 22 are axially spaced from one another and are connected via the shaft 20. In this exemplary embodiment, the two portions 21, 22 are disc-shaped but other shapes might also be possible. The first portion 21 has a greater diameter than the second portion 22. The first portion 21 is located in the first section 4*a* of the drive spring holder 4 and the second portion 22 is located in the second section 4*b* of the drive spring holder 4. The diameters of the portions 21, 22 are substantially the same as the inner diameters of the assigned sections 4*a*, 4*b* but sufficiently smaller to allow a rotation of the rotating collar 2 with respect to the drive spring holder 4. Moreover, the diameter of the first portion 21 is greater than the inner diameter of the second section 4*b* which limits the axial movement of the rotating collar 2 in distal direction D.

As can be further seen in FIG. 25, in the first locked state, the second portion 22 is offset in proximal direction P from a second bottom ring 4*d* of the drive spring holder 4. Likewise, the first portion 21 is offset in proximal direction P from a first bottom ring 4*c* of the drive spring holder 4.

The torsion drive spring 3 is received in the first section 4*a* and is fixed to the first section 4*a* at a connection point. The rotating collar 2 is received in the torsion drive spring 3 so that the torsion drive spring 3 circumferentially surrounds the shaft 20 of the rotating collar 2 at a proximal side of the first section 21. The shaft 20 of the rotating collar 2 is connected to the torsion drive spring 3 at a further connection point. The first portion 21 is offset with respect to the torsion drive spring 3 in distal direction D. In the first locked state, shown in FIG. 25, the torsion drive spring 3 is biased and induces a torque onto the rotating collar 2. The rotating collar 2 is prevented from a rotation with help of the first locking mechanism explained further below.

The plunger rod 1 is received in the rotating collar 2. In the first locked state, a portion of the plunger rod 1 projects from the rotating collar 2 in distal direction D. The stopper 82 of the syringe 8 is offset from the distal end of the plunger rod 1 in distal direction D.

FIG. 26 shows the part or arrangement of the auto-injector in the released state. The first locking mechanism has been released so that the rotating collar 2 was no longer prevented from rotating. Due to the torque induced by the drive spring 3, the rotating collar 2 rotates in a first rotational direction (clockwise or anti-clockwise) inside the drive spring holder 4. The rotating collar 2 and the plunger rod 1 are operatively coupled via a threaded interface. In the present case, the plunger rod 1 comprises an external thread 11 and the rotating collar 2 comprises an internal thread (not visible) engaging with the external thread 11 of the plunger rod 1. The coupling via the threaded interface is such that the rotation of the rotating collar 2 in the first rotational direction is converted into a movement of the plunger rod 1 in distal direction D.

During the axial movement of the plunger rod 1 induced by the rotation of the rotating collar 2, the plunger rod 1 itself does not rotate. This is realized by a coupling between the plunger rod 1 and the drive spring holder 4 via a splined interface. This is further illustrated in FIG. 27 showing a three-dimensional view of the part/arrangement of the auto-injector. The splined interface is realized by protrusions 40 of the drive spring holder 4 projecting in distal direction D from the second bottom ring 4*d* and engaging with or projecting into grooves 10 of the plunger rod 1, respectively. The grooves 10 extend along the longitudinal axis A, i.e. run essentially parallel to the longitudinal axis A. The grooves 10 are arranged opposite each other on the plunger rod 1. Instead of two grooves, as shown in FIG. 27, one groove and one corresponding protrusion 40 may be sufficient. However, more than two grooves 10 and associated protrusions 40 may also be used.

In the exemplary embodiments, the splined interface is in close proximity to the threaded interface, e.g. with a distance of at most 1 cm or at most 0.5 cm. This is beneficial since the torque on the plunger rod 1 is resolved over a short distance reducing the stresses within the plunger rod 1. The plunger rod 1 is often a small member likely to deform.

As can be further seen in FIG. 26, the rotating collar 2 does not only rotate but also moves axially in the proximal direction P, as already mentioned before. The movement in proximal direction P preferably starts immediately when the rotation is started. In this way the needle shroud 5 may reextend upon premature removal from the skin. The break loose force of the stopper 82 is typically 5 N or more. The ability of the torsion drive spring 3 to resolve axial loads may be smaller than this.

In the released state, the plunger rod 1 pushes the stopper 82 in distal direction D until the stopper 82 hits against a bottom region of the cartridge 81. A further distal movement of the stopper 82 and the plunger rod 1 is then prevented. After movement of the plunger rod 1 and the rotating collar 2 is finished, a portion of the plunger rod 1 is still received in the rotating collar 2.

An example of the dimensions of the plunger rod 1 is as follows: The plunger rod 1 has a diameter of 8.0 mm and the pitch of the outer thread is 3.17 mm. The coefficient of friction is 0.3. The mean contact radius, i.e. the position of the threaded face from the central axis of the plunger rod 1, is 3.75 mm.

An example of the torsion drive spring is 3 as follows: The material is polished and blued SAE 1095 steel. The height of the torsion drive spring is 12.0 mm, the thickness of the material is 0.168 mm, the length is 840.749 mm, the outer diameter is 20.0 mm, the arbor diameter is 10.0 mm. The bending stress limit is 2000 N·mm$^2$, the Youngs Modulus is 20000 N·mm$^2$, the number of revolutions before being biased is 3.

In general, the following conditions for the torsion drive spring turned out to be advantageous: The arbor diameter is between 12 to 25 times the thicknesses of the material. The length is between 5000 to 15000 times the thickness. The area of the torsion drive spring 3 is half the area of the drive spring holder 4 (e.g. in the first section 4*a*)+−10%. The bending stress for tempered polished and blued SAE 1095 steel should not exceed 2000 MPa.

An example of the used syringe 8 might be as follows: The drug inside the cartridge 81 has a volume of 2 ml. The viscosity of the material is 50 cP at room temperature. The inner needle diameter is 0.29 mm. The inner cartridge diameter is 8.65 mm. The friction of the stopper 82 is 10 N. The stopper gap, i.e. the initial clearance between the proximal end of the stopper 82 and the distal end of the plunger rod 1, is 2 mm.

4. First Locking Mechanism and Release of the First Locking Mechanism

The previously mentioned first locking mechanism or first rotation-locking mechanism, respectively, and how it is released is described in further detail in the following in connection with the FIGS. 28 to 33.

Figure 28:
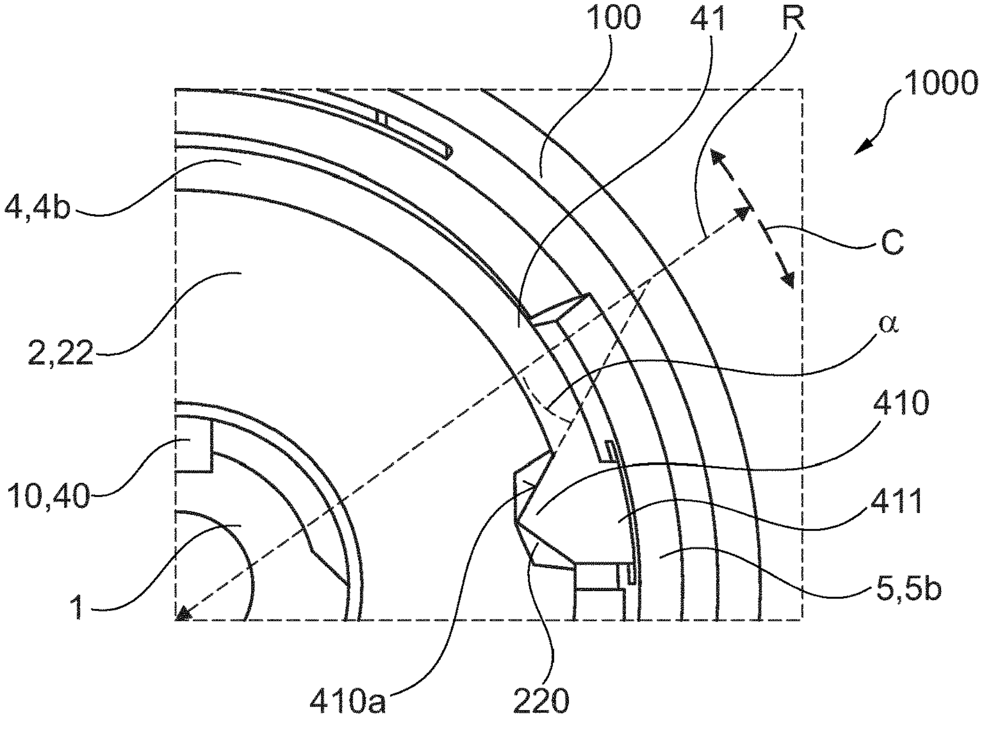
FIGS. 28 to 33 show sections of the drug delivery device according to the first and second exemplary embodiment in different positions during usage for illustrating an exemplary embodiment of a first locking mechanism and the release of the first locking mechanism.

FIG. 28 illustrates a cross-sectional view of the auto-injector 1000 of the first and second exemplary embodiment with the cutting plane being perpendicular to the longitudinal axis A and running through the second portion 22 of the rotating collar 2. As can be seen, the drive spring holder 4 comprises a displaceable element 41 in the form of a resilient arm (see also FIGS. 27 and 49). The resilient arm 41 is integrally formed with the drive spring holder 4 and is arranged in the second section 4*b* of the drive spring holder 4. The resilient arm 41 is oriented circumferentially, i.e. a main extension direction of the resilient arm 41 is along the angular direction C. One end of the resilient arm 41 is connected to the drive spring holder 4, the other end is free and movable in radial direction R.

The resilient arm 41 comprises a protrusion 410 projecting radially inwardly, i.e. in a radial direction pointing towards the longitudinal axis A. The protrusion 410 tapers radially inwardly. The protrusion 410 comprises a beveled surface 410*a*, which essentially runs parallel to the longitudinal axis A and which is tilted with respect to the radial direction R and with respect to the angular direction C. For example, the angle $\alpha$ between the beveled surface 410*a* and the radial direction R is at least 10° and at most 80°, preferably between 30° and 55°.

In the first locked state, shown in FIG. 28, the resilient arm 41 is in a first radial position in which the protrusion 410 engages or projects into a recess 220 of the second portion 22 of the rotating collar 2, respectively. In this way a rotation-lock interface is formed, coupling the resilient arm 41 and the rotating collar 2 and preventing the rotating collar 2 from a rotation.

The first radial position may be the relaxed position of the resilient arm 41 which it would occupy if no further forces pointing radially inwardly and radially outwardly were acting on the resilient arm 41. Alternatively, the resilient arm 41 may be biased in the first radial position, such that the first radial position is a stressed position of the resilient arm 41.

As long as the resilient arm 41 is in the first radial position in which the protrusion 410 projects into the recess 220, a rotation of the rotating collar 2 in the first rotational direction induced by the torsion drive spring 3 is prevented. However, the torque acting on the rotating collar 2 presses a surface of the second portion 22 delimiting the recess 220 against the beveled surface 410*a* of the protrusion 410 of the resilient arm 41. This results in a force trying to move the resilient arm 41 radially outwardly from the first radial position into a second radial position. In other words, the torque induced by the torsion drive spring 3 biases the resilient arm 41 radially outwardly. If a movement in radial outward direction would be allowed, the first locking mechanism would be released automatically and the auto-injector 1000 would transfer into the released state.

In the first locked state, an arm 5*b* of the needle shroud 5 is located at the height of, i.e. axially overlapping or aligned with, the resilient arm 41 and prevents the resilient arm 41 from moving radially outwardly out of and away from the first radial position. Indeed, the resilient arm 41 abuts against the needle shroud 5 in outward radial direction such that an outward radial movement is blocked. The resilient arm 41 comprises a further protrusion 411 which projects radially outwardly and which abuts against the needle shroud 5. An outward radial movement of the needle shroud 5 is prevented, e.g. by the housing 100 circumferentially surrounding the needle shroud 5.

Figure 29:
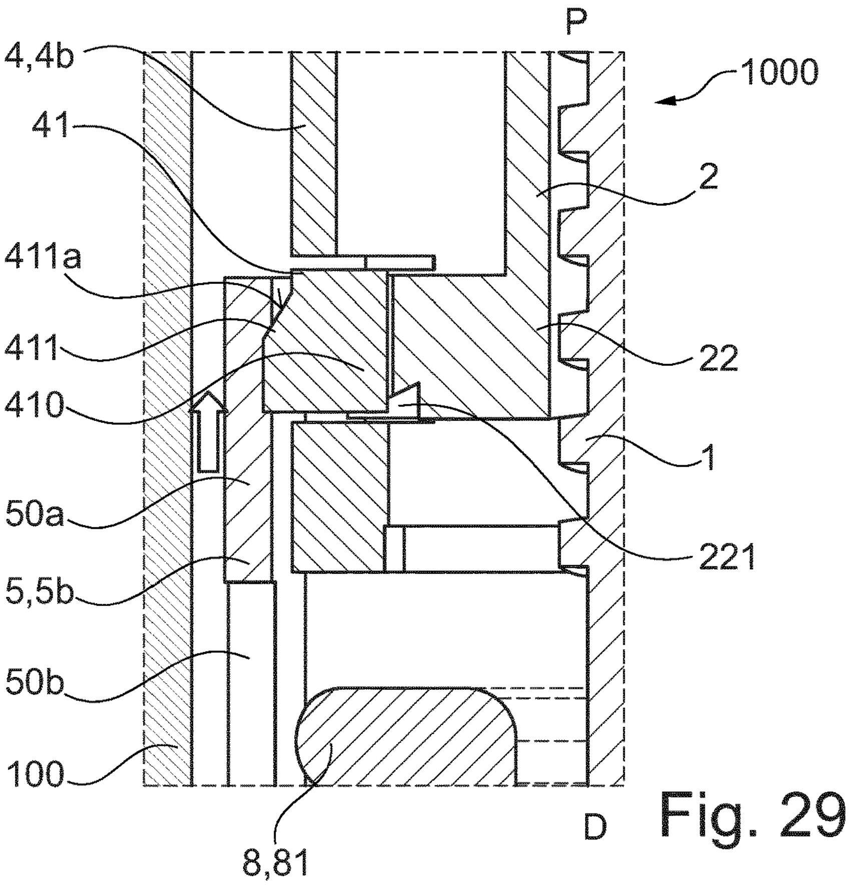

FIG. 29 shows a section of the auto-injector 1000 in the same state as in FIG. 28 but now in a cross-sectional view with the longitudinal axis lying in the cutting plane. There it can be seen that the arm 5*b* of the needle shroud 5 comprises a first section 50*a*, namely a wall portion, and a second section 50*b*, namely a recess, e.g. a cut-out. The recess 50*b* is offset in distal direction D with respect to the wall portion 50*a*. In the first locked state, the needle shroud 5 is in its extended position, in which the wall portion 50*a* blocks the outward radial movement of the resilient arm 41.

FIG. 29 further indicates that the needle shroud 5 can be moved from its extended position into a retracted position which would result in an overlap or alignment between the recess 50*b* and the resilient arm 41 in axial direction and rotational direction. Movement of the needle shroud 5 in proximal direction P requires a force, also called activation force, which includes the force needed to compress the shroud spring 7 and the friction force resulting from the resilient arm 41 being pressed against the needle shroud 5.

As an numerical example: Assuming a torque induced by the torsion drive spring 3 onto the rotating collar 2 of 102 Nmm, a radius at which the rotating collar 2 abuts against the protrusion 410 of 7.5 mm and an angle α of 39° would result in a force on the resilient arm 41 in radial direction of about 10.57 N. Assuming a friction coefficient of 0.3, the friction force would be about 3.17 N. Assuming further that the force for compressing the shroud spring 7 is about 6 N, the activation force would be about 9 N.

Figure 30:
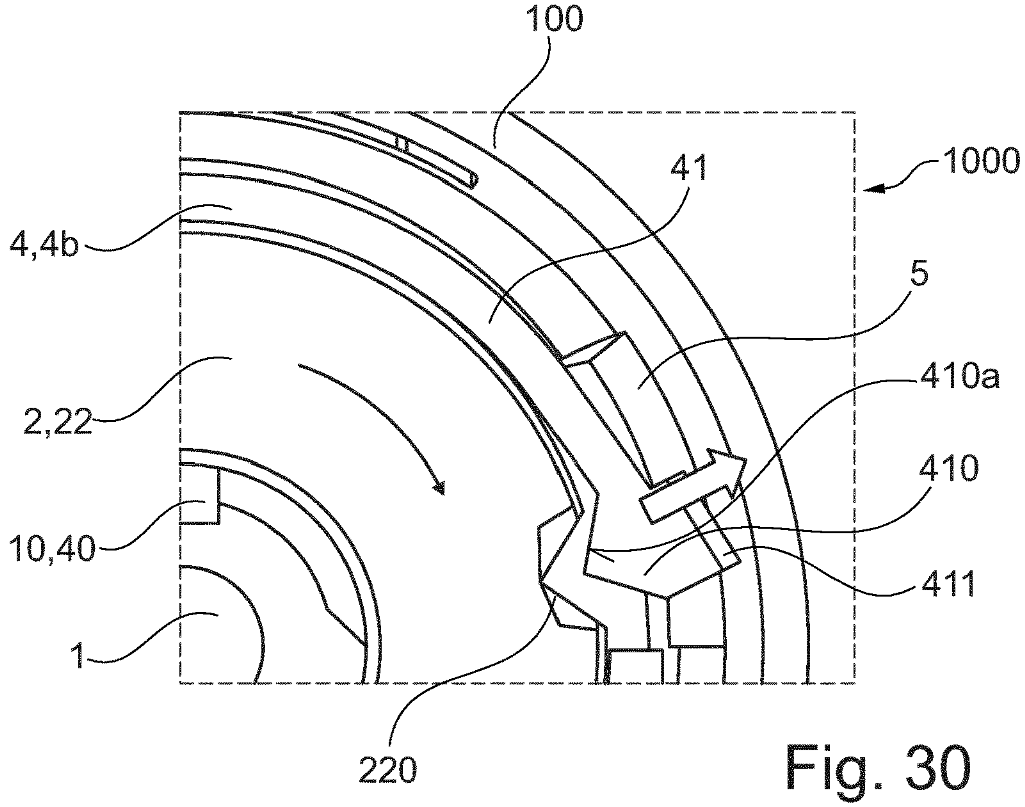
Figure 31:
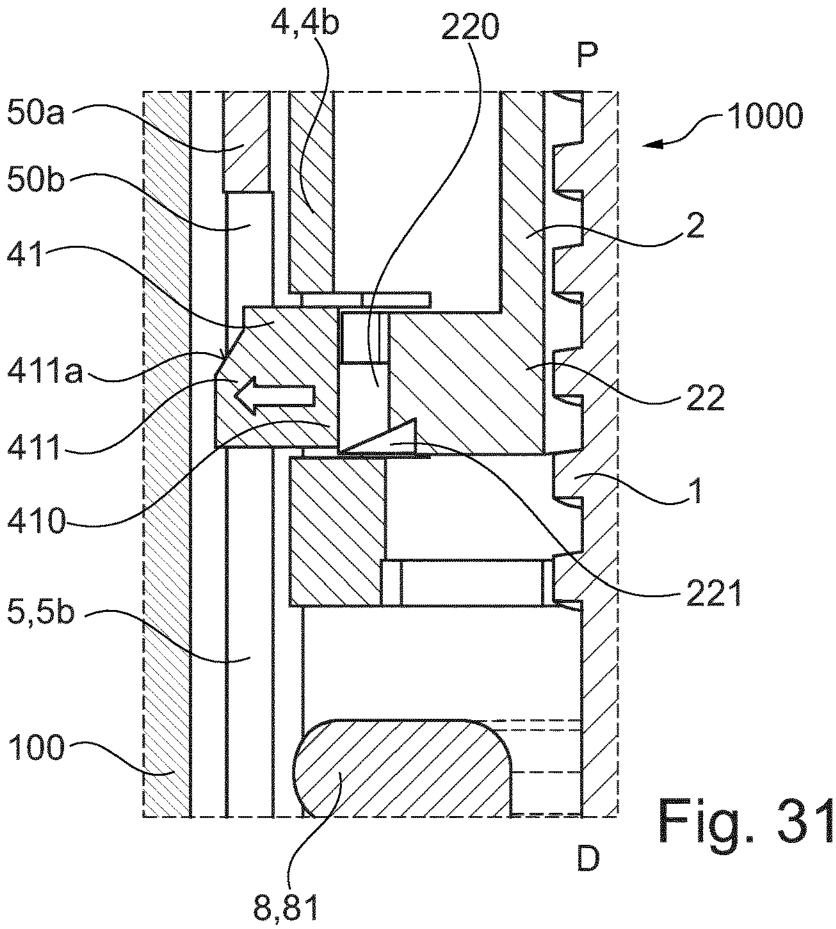

FIGS. 30 and 31 show sections of the auto-injector 1000 which corresponds to the sections shown in FIGS. 28 and 29. Now the needle shroud 5 has been moved in its retracted position (by overcoming the activation force). This movement releases the first locking mechanism so that the auto-injector 1000 is switched from the first locked state into the released state. As the recess 50*b* of the needle shroud 5 is now at the height of the resilient arm 41, the outward radial movement of the resilient arm 41 is no longer blocked. The resilient arm 41 automatically—induced by the torque on the rotating collar 2—leaves its first radial position and deflects into a second radial position in which the protrusion 410 no longer projects into the recess 220, thus the rotation-lock interface is resolved and the first locking mechanism is released. As a result of this, the rotation of the rotating collar 2 is no longer prevented. The rotating collar 2 starts to rotate (see FIG. 30) due to the force induced by the drive spring 3, thereby forcing the plunger rod 1 into an axial movement.

Figure 32:
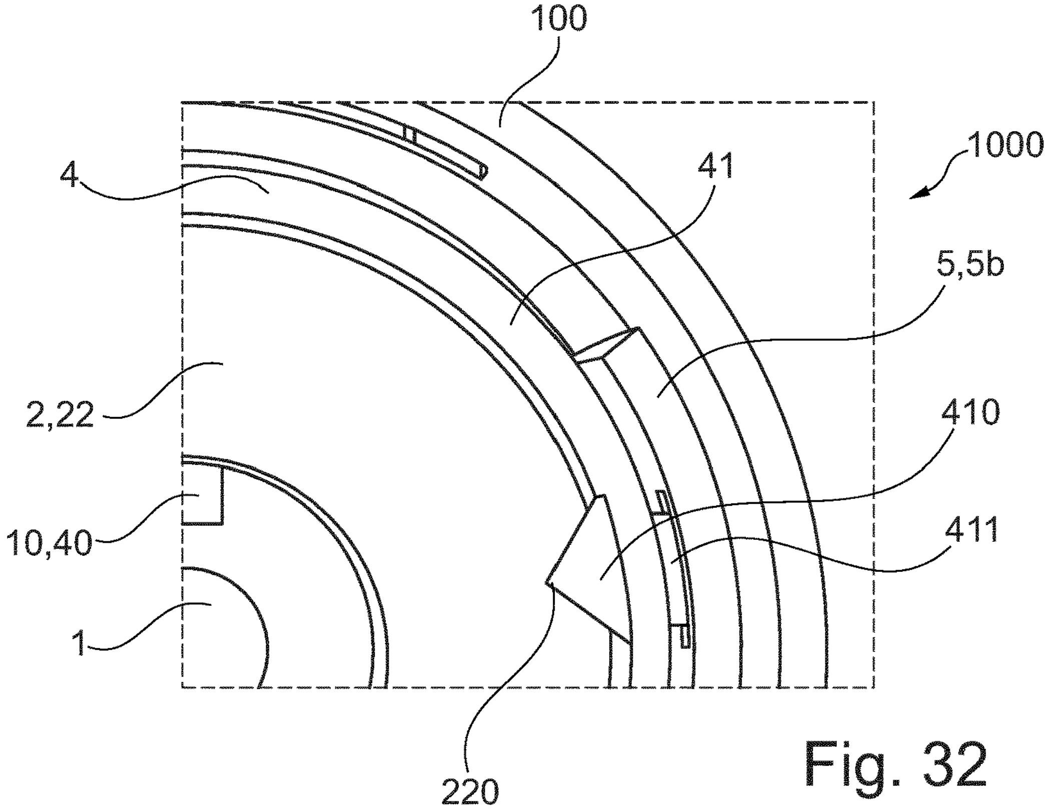
Figure 33:
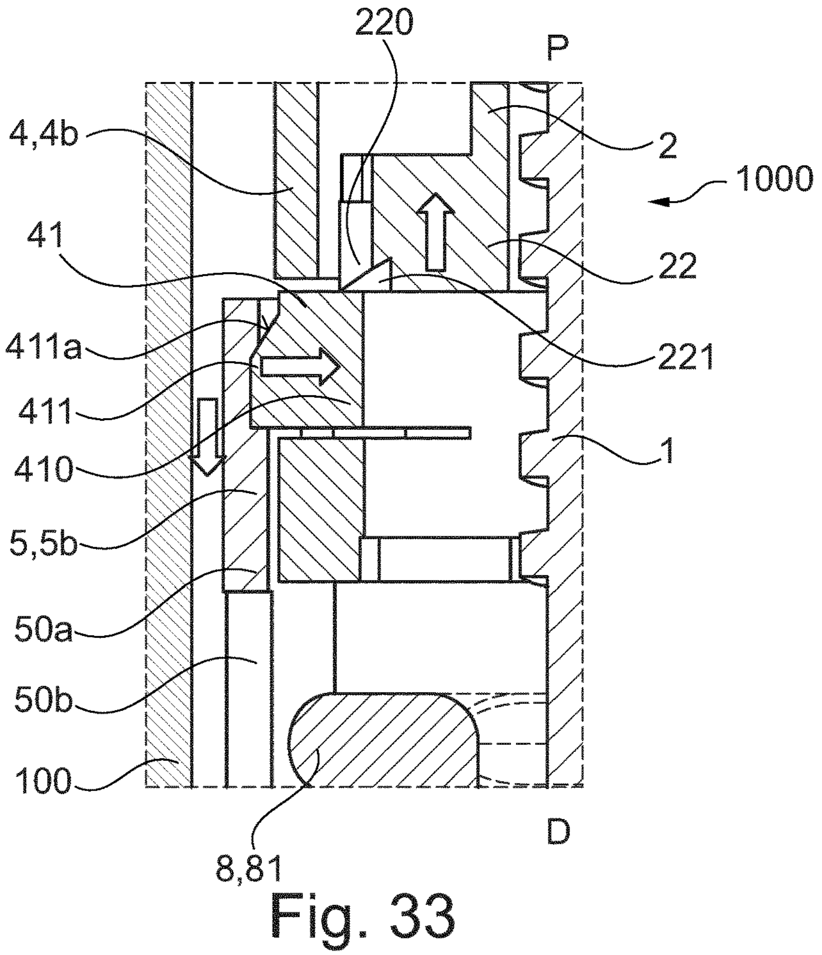

FIGS. 32 and 33 show sections of the auto-injector 1000 which corresponds to the sections shown in FIGS. 28 and 29. Now, the auto-injector 1000 is switched into a third locked state or post-released state. For example, the distal end of the auto-injector 1000 has been removed from the body so that the needle shroud 5 automatically moves from the retracted position back into the extended position induced by the shroud spring 7.

The protrusion 411 of the resilient arm 41 comprises a slide feature 411*a* in the form of a beveled surface 411*a*. The beveled surface 411*a* and the longitudinal axis may include, e.g., an angle between 10° and 80° inclusive. An edge of the needle shroud 5 delimiting the recess 50*b* in proximal direction P may contact this beveled surface 411*a* when the needle shroud 5 moves in distal direction D. Due to the beveled surface 411*a*, the resilient arm 41 is pushed radially inwardly when the edge hits the protrusion 411. In this way, the movement of the needle shroud 5 back into the retracted position is possible without the needle shroud 5 jamming up with the resilient arm 41. The slide feature may additionally or alternatively be formed in the needle shroud 5 (see FIGS. 39 and 40).

In the case the resilient arm 41 indeed abuts against the edge of needle shroud 5 when the needle shroud 5 is moved in distal direction D, the movement of the resilient arm 41 in inward radial direction is possible, since the rotating collar 2, particularly the second portion 22 of the rotating collar 2, has moved in proximal direction P. Thus, the second portion 22 is now offset in proximal direction P with respect to the resilient arm 41. For this reason, it is particularly beneficial if the rotating collar 2 moves in the proximal direction immediately when the plunger rod 1 starts to move in distal direction, i.e. before the plunger rod 1 hits the stopper 82. If the user lifts the auto-injector 1000 early from the skin, e.g. before the drug is started to be administered, the needle shroud 5 can then still move back in distal direction and the third locking mechanism explained below can be activated.

5. Third Locking Mechanism/Post-Released Locking Mechanism

A third locking mechanism or post-released locking mechanism, respectively, is described in further detail in the following in connection with the FIGS. 34 to 40.

FIGS. 34 to 38 illustrate a first exemplary embodiment of the third locking mechanism. This mechanism is configured to prevent the needle shroud 5 from being moved from the extended position into the retracted position after the drug has been delivered or after the autoinjector has once been activated. Thus, the risk of injuries due to an exposed needle may be reduced. This third locking mechanism may be used in all exemplary embodiments of the auto-injector 1000 described herein.

FIG. 34 shows again a cross-sectional view of a section of the auto-injector 1000 with the cutting plane comprising the longitudinal axis A. However, the cutting plane is rotated compared to what is shown in, e.g. FIG. 33 (see FIG. 38 for a perspective view). It can be seen in FIG. 34 that the arm 5*b* of the needle shroud 5 comprises a first stop feature 51 in the form of a displaceable element 51 which is located at the proximal end of the arm 5*b*. The displaceable element 51 is a resilient arm 51 which is integrally formed with the rest of the needle shroud 5 and, therefore, is axially and rotationally fixed to the rest of the needle shroud 5. Thus, the resilient arm 51 moves in axial direction when the needle shroud 5 is moved in axial direction.

Figure 38:
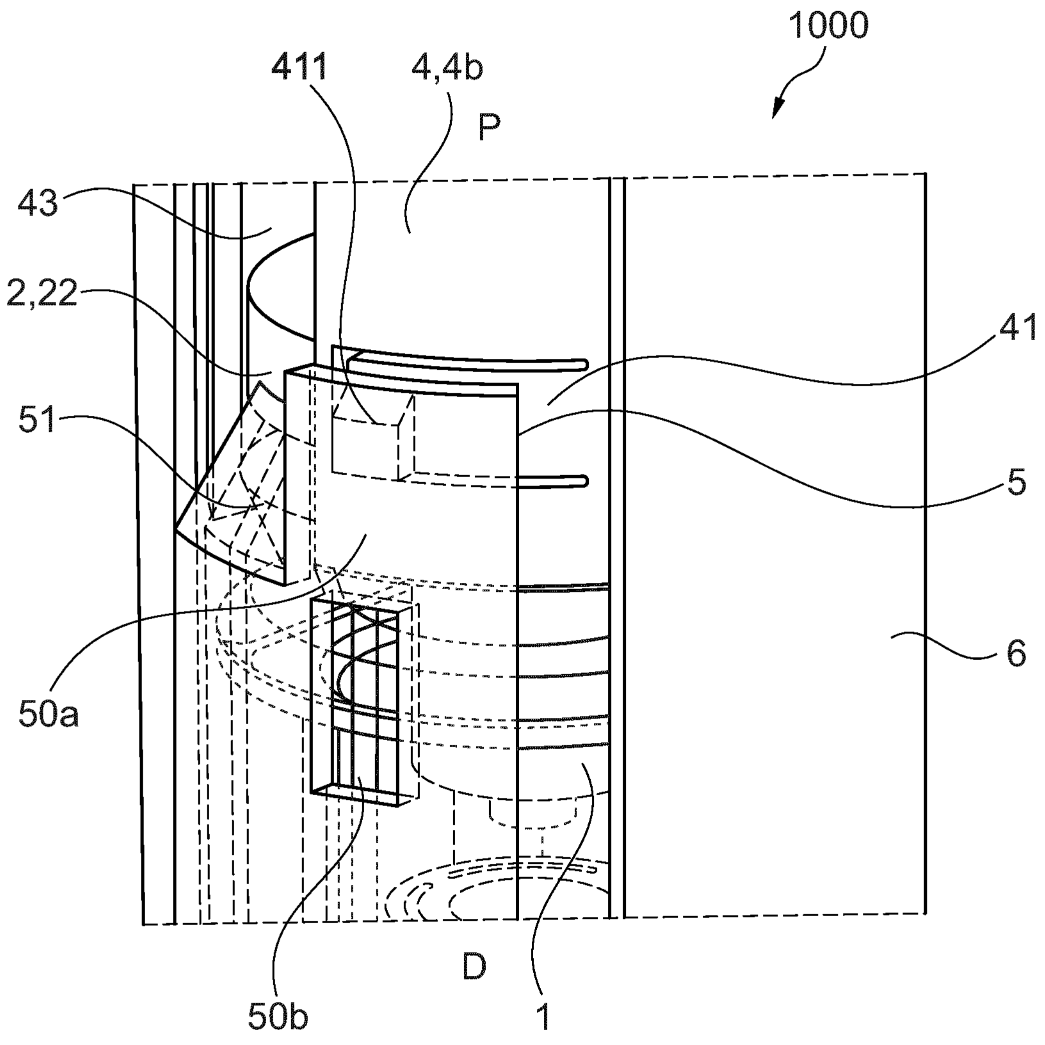

As can be seen in FIG. 38, the resilient arm 51 is located on the same height as the wall portion 50*a* when seen along to the longitudinal axis A and is arranged offset from the wall portion 50*a* in the angular direction C.

Simultaneously to extending in proximal direction P, the resilient arm 51 also extends radially inwardly, i.e. a main extension direction of the resilient arm 51 has a component along the proximal direction P and a component along the inward radial direction. Thus, a proximal end of the resilient arm 51 is located further radially inwardly than a distal end of the resilient arm 51. The proximal end of the resilient arm 51 is free and displaceable in the radial direction. The distal end of the resilient arm 51 is connected to the rest of the needle shroud 5. A kink is formed between the distal end of the resilient arm 51 and the rest of the needle shroud 5.

Figure 34:
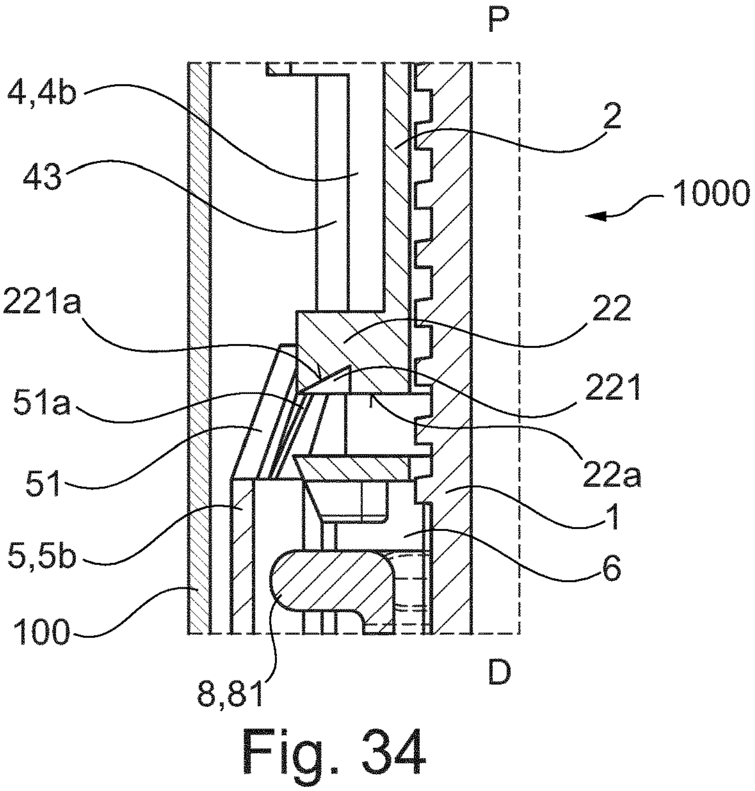
FIGS. 34 to 38 show sections of the drug delivery device according the first and second exemplary embodiment in different positions during usage for illustrating a first exemplary embodiment of a third locking mechanism.

In FIG. 34, the auto-injector 1000 is in the first locked state (also referred to as initial state or pre-released state), in which a rotation of the rotating collar 2 is blocked by the first locking mechanism as described before. The resilient arm 51 is in a first radial position, which may be a biased position of the resilient 51. The resilient arm 51 is held in the first radial position and is prevented from moving radially inwardly by the second portion 22 of the rotating collar 2. In the present case, the drive spring holder 4 comprises a recess 43, namely a cut-out 43, into which the resilient arm 51 projects. The resilient arm 51 abuts against the second portion 22 in inward radial direction.

Figure 35:
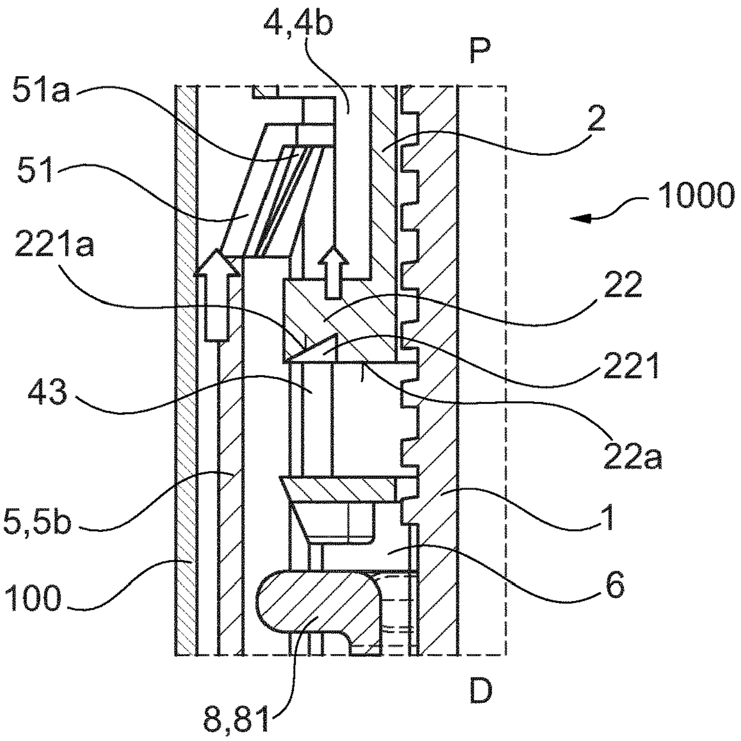

FIG. 35 shows a section of the auto-injector 1000 in a position during usage, when the needle shroud 5 is moved from its extended position into the retracted position so that the auto-injector 1000 switches into the released state. Together with the needle shroud 5, the resilient arm 51 has moved in proximal direction P such far that the second portion 22 of the rotating collar 2 does no longer hold the resilient arm 51 in the first radial position. This allowed the resilient arm 51 to move radially inwardly into a second radial position. In the released state of the auto-injector 1000 and the needle shroud 5 being in the retracted position, the resilient arm 51 is offset with respect to the second portion 22 in proximal direction P.

In the released state of the auto-injector 1000, the rotating collar 2 moves in proximal direction P from a nonlocking position into a locking position, as it is indicated in FIG. 35.

Figure 36:
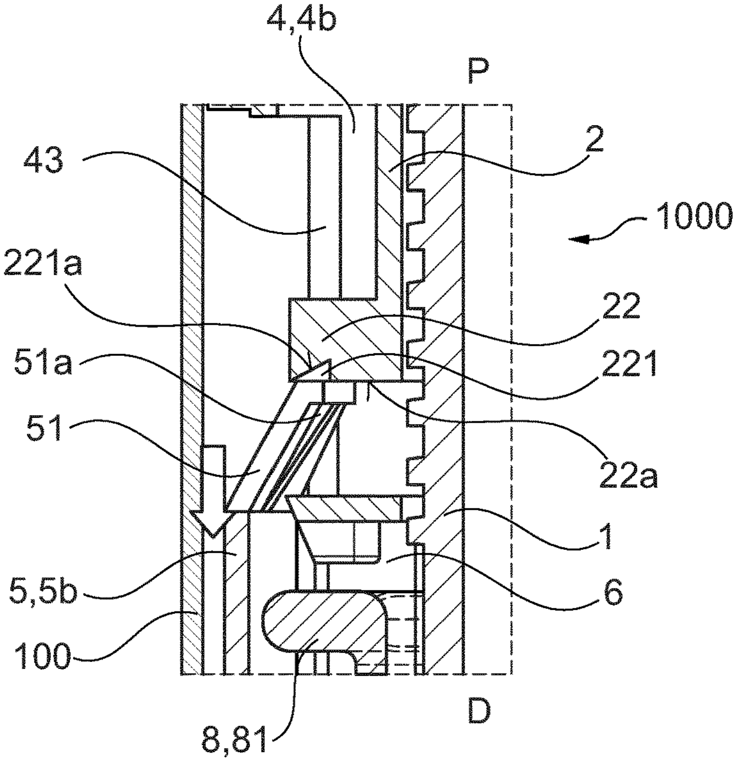

FIG. 36 shows a section of the auto-injector 1000 in a third locked state, also referred to as post-released state, which is a state after usage, i.e. after the drug has been dispensed. The third locked state is a state after the released state. In this third locked state, the needed shroud 5 is again in its extended position. As can be seen in FIG. 36, the second portion 22 has moved in proximal direction P such far that the resilient arm 51 is now offset in distal direction D with respect to the second portion 22 so that the second portion 22 can no longer hold the resilient arm 51 in the first radial position. Therefore, in the third locked state, the resilient arm 51 is in the second radial position. When trying to move the needle shroud 5 from the extended position towards the retracted position, the resilient arm 51 in the second radial position hits against a second stop feature 22*a*, namely a surface of the second portion 22 which runs essentially perpendicularly to the longitudinal axis and faces in distal direction D. This prevents a further movement of the needle shroud 5 in proximal direction P. For example, the auto-injector 1000 is configured such that, in the third locked state, the resilient arm 51 hits against the surface 22*a* of the second portion 22 when moving the needle shroud 5 in proximal direction P before the needle is exposed.

When the resilient arm 51 hits against the surface 22*a* of the second portion 22, a lock interface is formed between the resilient arm 51 and the surface 22*a*. For this purpose, a recess 221 or notch 221 is formed in the surface 22*a* which engages with the proximal end of the resilient arm 51 when the resilient arm 51 hits against the surface 22*a*. The recess 221 is delimited by a beveled surface 221*a* which is tilted with respect to the longitudinal axis A and the radial direction. For example, an angle between the beveled surface 221*a* and the longitudinal axis and/or the radial direction is between 10° and 80° inclusive. When the proximal end of the resilient arm 51 engages into the recess 221, the resilient arm 51 hits against the beveled surface 221*a* and slides along the beveled surface 221*a* thereby being forced to move radially inwardly. The recess 221 with the beveled surface 221*a* thus prevents the resilient arm 51 from sliding along the surface 22*a* in outward radial direction.

The surface 22*a* of the second portion 22 may circumferentially extend around the longitudinal axis and/or the rotational axis of the rotating collar 2 by at least 270° and may have a constant geometrical form along its extension along the angular direction. In this way, the functionality of the third locking mechanism is almost independent on how far the rotating collar 2 has rotated in the released state.

As can be further seen in FIGS. 34 to 36, the resilient arm 51 comprises a slide feature 51*a* in the form of a ramp 51*a*. During movement of the needle shroud 5 from the retracted position into the extended position, the ramp 51 hits against a proximal edge of the second portion 22. The ramp 51*a* is designed such that it forces the resilient arm 51 to slide along the edge of the second portion 22 so that the resilient arm 51 is pushed radially outwardly. This allows the resilient arm 51 to pass the second portion 22 without being jammed up with the second portion 22. After having passed the second portion 22 during movement towards the extended position, the resilient arm 51 springs back into the second radial position.

Figure 37:
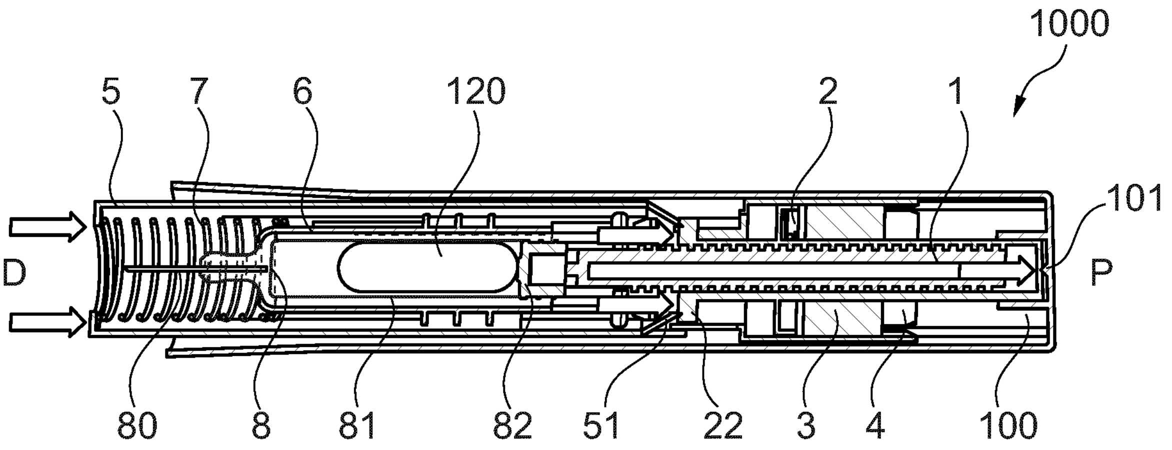

FIG. 37 shows the auto-injector 1000 in a cross-sectional view in the third locked state. As can be seen, the needle shroud 5 cannot be moved so far in proximal direction P that the needle 80 is exposed because the resilient arm 51 hits against the surface 22*a* of the second portion 22 before.

Figure 39:
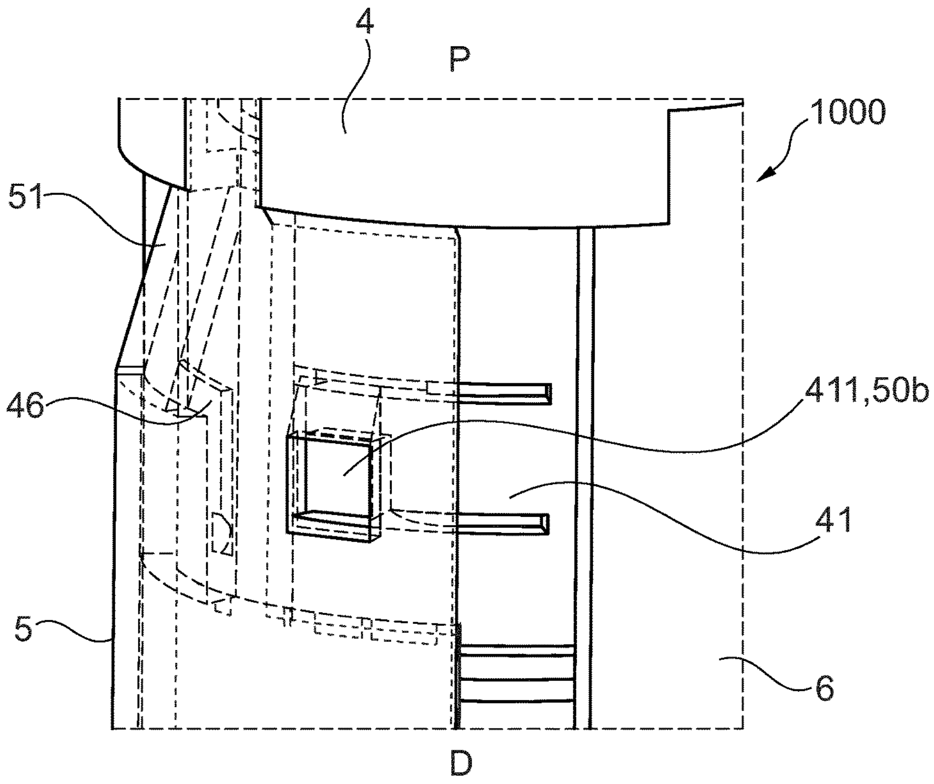
FIGS. 39 and 40 show sections of the drug delivery device in different positions during usage for illustrating a second exemplary embodiment of the third locking mechanism.
Figure 40:
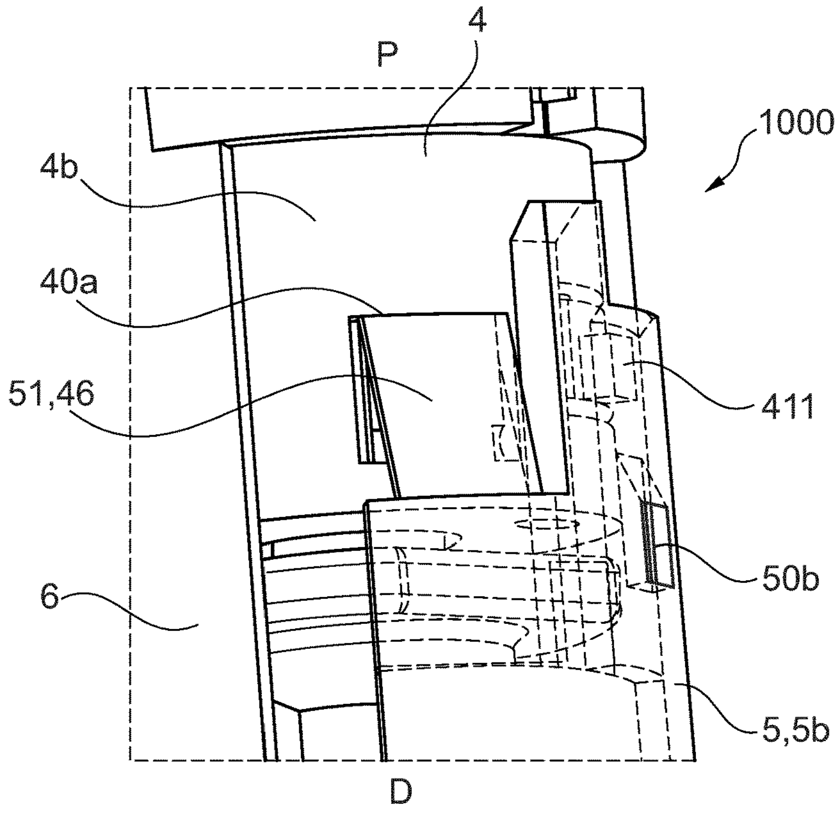

FIGS. 39 and 40 illustrate a second exemplary embodiment of the third locking mechanism. Also this exemplary embodiment of the third locking mechanism may be used in all exemplary embodiments of the auto-injector described herein.

The main difference to the first exemplary embodiment is that, in the third locked state of the auto-injector 1000, when moving the needle shroud 5 towards the retracted position, the resilient arm 51 does not hit against a stop feature axially fixed to the rotating collar 2 but against a stop feature 40*a* axially fixed to the drive spring holder 4. The stop feature 40*a* is formed by an edge of the drive spring holder 4. The edge 40*a* delimits a recess/cut-out in the drive spring holder 4 in proximal direction P.

A flap 46, which is axially fixed to the drive spring holder 4, e.g. integrally formed with the drive spring holder 4, partially fills this recess. A distal end of the flap 46 is connected to the drive spring holder 4 and a proximal end of the flap 46 is free and displaceable in radial direction. The proximal end of the flap 46 is spaced from the edge 40*a* by a small gap.

In the first locked state, when the needle shroud 5 is still in the extended position, the rotating collar 2, particularly the second portion 22 of the rotating collar 2, abuts against the flap 46 of the drive spring holder 4 in outward radial direction and holds the flap 46 in a first radial position, in which the flap 46 substantially terminates flush with the edge 40*a* in outward radial direction. The second portion 22 prevents the flap 46 from being displaced in the inward radial direction. On the other hand, the flap 46 abuts against the resilient arm 51 of the needle shroud 5. In the first radial position of the flap 46, the flap 46 holds the resilient arm 51 in its first radial position.

When now moving the needle shroud 5 in proximal direction P, the resilient arm 51 can pass the edge 40*a* without jamming up with the edge 40*a*, since the flap 46 terminates flush with the edge 40*a* and since the flap 46 is held in its first radial position by the second portion 22. Moving the needle shroud 5 further into its retracted position releases the first locking mechanism, the auto-injector 1000 switches from the first locked state into the released state and the rotating collar 2 together with the second portion 22 moves in proximal direction P into a locking position. The needle shroud 5 being in its retracted position is shown in FIG. 39.

When moving the needle shroud 5 back from its retracted position into the extended position, the resilient arm 51 passes the edge 40*a* and stops at the height of the flap 46. This position is shown in FIG. 40. The auto-injector 1000 is now in the third locked state. The resilient arm 51 and optionally also the flap 46 may be biased in inward radial direction. Thus, the resilient arm 51 and the flap 46 move radially inwardly and each reach a second radial position.

This is possible because the elements are no longer held by the second portion 22 of the rotating collar 2 in their respective first radial position.

The flap 46 being in the second radial position does no longer terminate flush with the edge 40*a* of the drive spring holder 4. Thus, when moving the needle shroud 5 from the extended position towards the retracted position, the resilient arm 51 will hit against the edge 40*a* which prevents a further movement of the needle shroud 5 in proximal direction P.

6. Drop Protection Mechanism

An exemplary embodiment of a drop protection mechanism is described in further detail in the following in connection with the FIGS. 41 and 42. The drop protection mechanism shall prevent the release of the first locking mechanism when the auto-injector 1000 is unintentionally dropped. In fact, when the auto-injector 1000 of the exemplary embodiments described herein is in the first locked state, a movement of the rotating collar 2 in proximal direction P would result in a release of the first locking mechanism.

Figure 41:
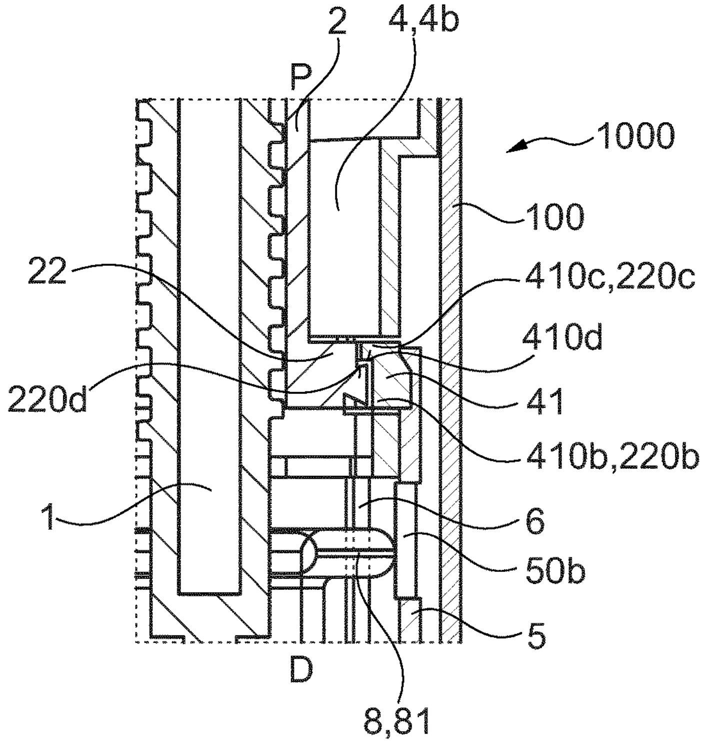
FIGS. 41 and 42 show sections of the drug delivery device according to the first and second exemplary embodiment in different positions during usage for illustrating an exemplary embodiment of a drop protection mechanism.

FIG. 41 shows a section of the auto-injector 1000 of the first and second exemplary embodiments in cross-sectional view illustrating a first part of the drop protection mechanism. In the first locked state of the auto-injector 1000 and when the needle shroud 5 is still in the extended position (initial position), the second portion 22 and the resilient arm 41 engage with each other (protrusion 410 projects into recess 220) and this engagement is retained by the needle shroud 5 holding the resilient arm 41 in its radial position as explained in connection with the first locking mechanism. The engagement, however, also establishes an axial-lock interface preventing the rotating collar 2 from an axial movement at least in proximal direction P.

Figure 49:
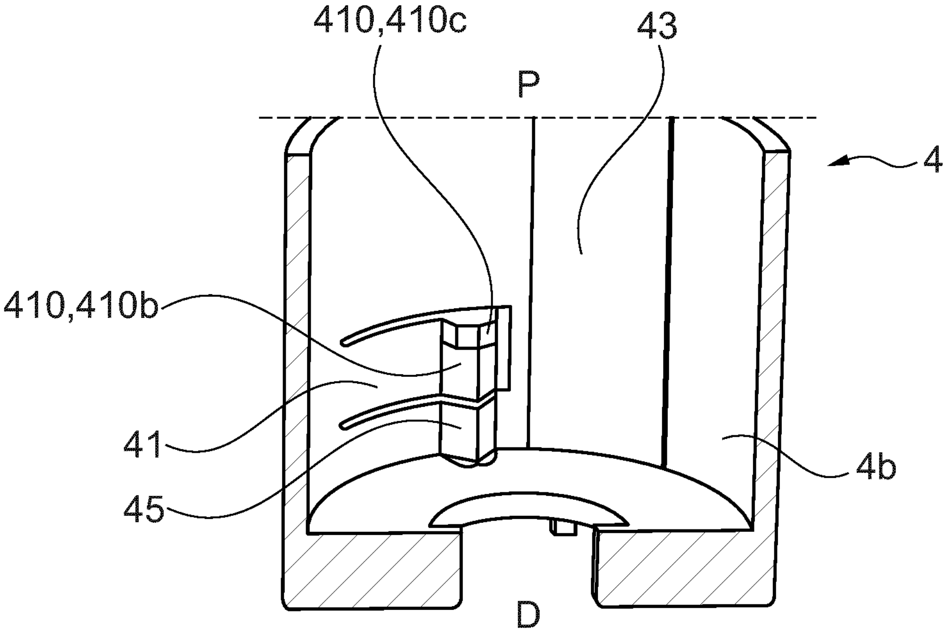
FIG. 49 shows an isolated drive spring holder of the drug delivery according to the first and second exemplary embodiments.

For this purpose, the protrusion 410 of the resilient arm 410 is a stepped protrusion having two sections 410*b*, 410*c* (see also FIG. 49). The recess 220 in the second portion 22 of the rotating collar 2 is a stepped recess also having two sections 220*b*, 220*c*. The sections 410*b*, 410*c* are connected by a surface 410*d* running essentially perpendicularly to the longitudinal axis. The sections 220*b*, 220*c* are also connected by a surface 220*d* running essentially perpendicularly to the longitudinal axis. The surface 220*d* is located more distally than the surface 410*d*. These surfaces 220*d*, 410*d* abut or hit against each other when the rotating collar 2 is moved in proximal direction P and, in this way, the rotating collar 2 is prevented from moving in proximal direction P as long as the protrusion 410 projects into the recess 220.

The first part of the drop protection mechanism described in connection with FIG. 41 could, however, be released when the needle shroud 5 would unintentionally be moved in proximal direction P. Therefore, in one exemplary embodiment, the drop protection mechanism comprises a second part illustrated in connection with FIG. 42.

Figure 42:
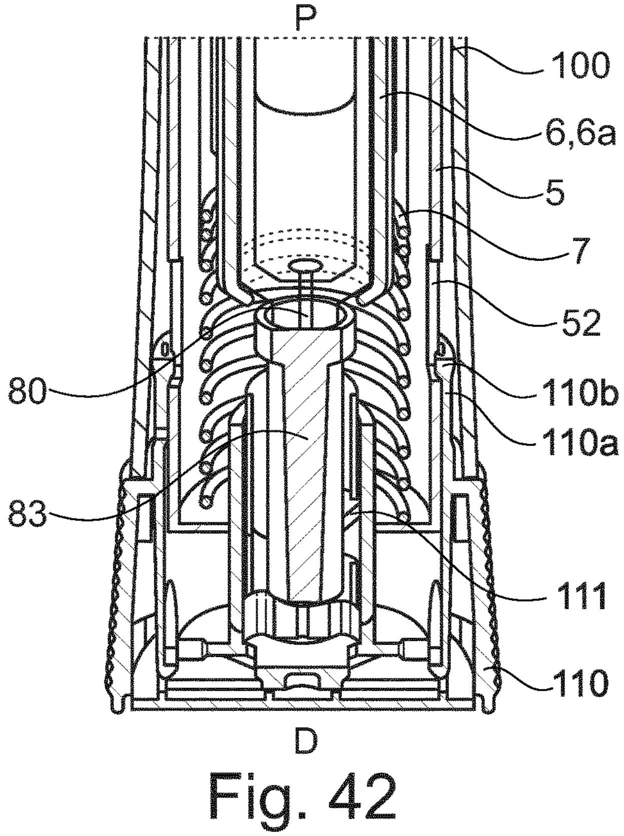

FIG. 42 shows a section of the auto-injector in a cross-sectional view with the cutting plane running parallel to the longitudinal axis A. Shown is the distal end of the auto-injector with the cap 110 still being coupled to the housing 100. The cap 110 is in its most proximal position and cannot be moved further in proximal direction P with respect to the housing 100 since it hits against the housing 100 when moved in this direction. The cap 110 comprises a radially displaceable cap-lock element 110*a*, namely a resilient arm 110*a*, with a protrusion 110*b* protruding radially inwardly and engaging into a cap-lock element 52, namely a recess 52, particularly a cut-out 52, in the needle shroud 5.

In FIG. 42, the auto-injector 1000 is shown when it is dropped which results in a proximal movement of the needle shroud 5. The needle shroud 5, particularly an edge of the needle shroud 5 delimiting the recess 52 in distal direction D, hits against the protrusion 110*b* due to its proximal movement. This prevents a further movement of the needle shroud 5 in proximal direction P as long as the cap 110 is coupled to the housing 100. Thus, the needle shroud 5 cannot reach the retracted position in which it would no longer hold the resilient arm 41 in its radial position.

In the position shown in FIG. 42, the resilient arm 110*a* cannot or only slightly be moved in outward radial direction as the housing 100 circumferentially surrounds the resilient arm 110*a* and abuts or almost abuts against the resilient arm 110*a* thereby preventing an outward radial movement of the resilient arm 110*a*.

The protrusion 110*b* is located at a proximal end of the resilient arm 110*a* of the cap 110. Normally, when the drug delivery device is not dropped, the edge of the needle shroud 5 delimiting the recess 52 in distal direction D is located further distal as to what is shown in FIG. 42. When removing the cap 110, the cap 110 is moved in distal direction D until the protrusion 110*b* hits against said edge of the recess 52. The resilient arm 110*a* can then move in radial outward direction, because in this position of the cap 110, the housing 100 does not prevent the resilient arm 110*a* from being moved radially outwardly. The resilient arm 110*a* can disengage from the recesses 52 and the cap 110 can be completely removed. The protrusion 110*b* has a beveled surface (slide feature) which hits against the edge of the recess 52 and thereby forces the resilient arm 110*a* to deflect radially outwardly when the cap 110 is moved in distal direction D.

7. Subassemblies, Assembling and Second Locking Mechanism

Figure 43:
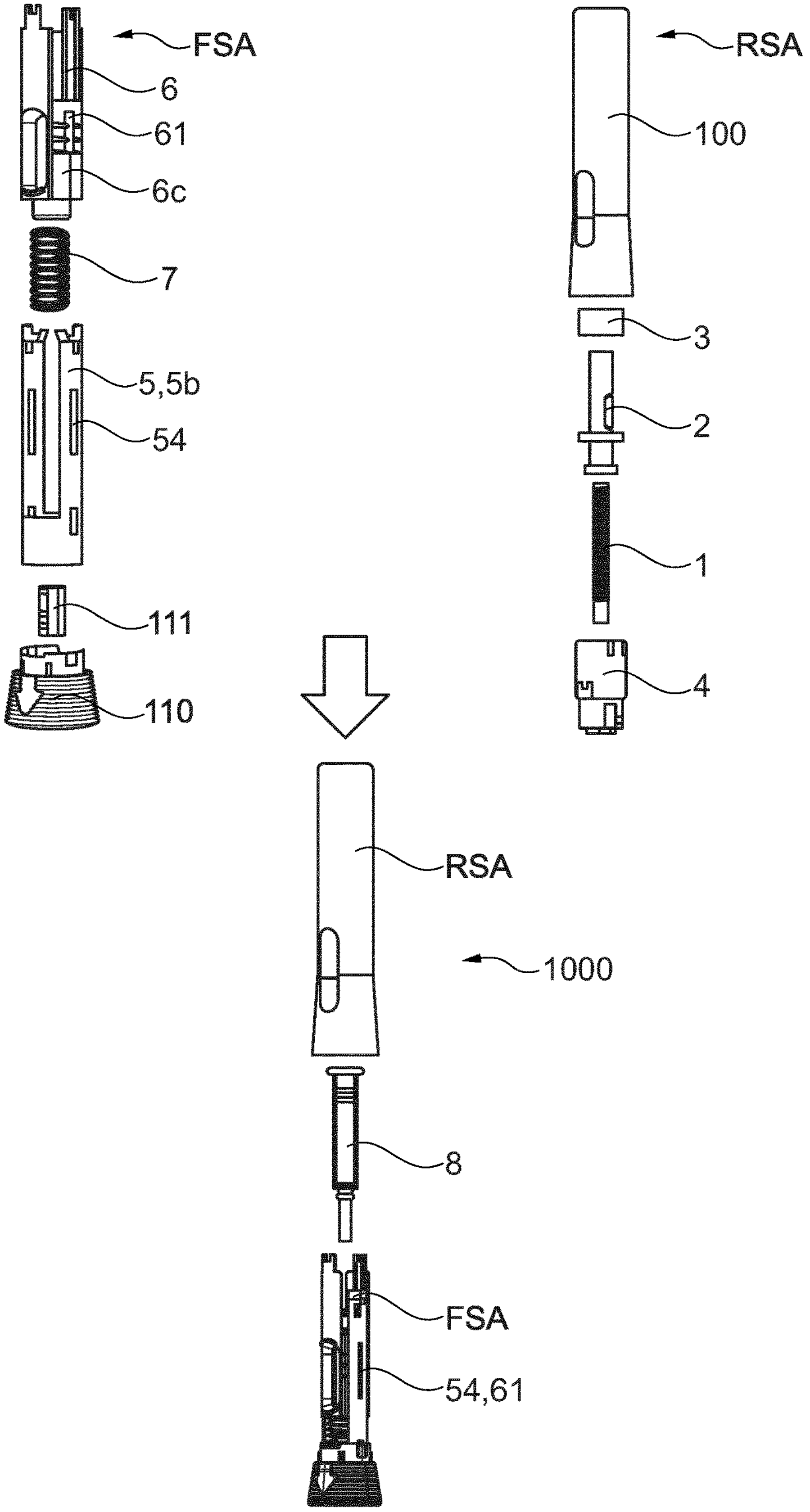
FIG. 43 shows the different subassemblies of the drug delivery device according to the first exemplary embodiment and a step during assembling a drug delivery device.

FIG. 43 shows the front subassembly FSA (also referred to as release subassembly FSA or container-holder subassembly FSA) and the rear subassembly RSA (also referred to as drive subassembly RSA) of the auto-injector according to the first exemplary embodiment in an exploded view as well as a position during assembling the front subassembly FSA and the rear subassembly RSA to an auto-injector 1000. These figures correspond to the FIGS. 13, 15 and 16. It is therefore mainly referred to the description in connection with these figures.

What can be seen in FIG. 43 is that the support portion 6*c* of the syringe holder 6 comprises a first rotation-lock features 61 in the form of protrusions 61 or ribs 61 which protrude in outward radial direction and which have a main extension direction along the longitudinal axis. These ribs 61 are configured to engage with second rotation-lock features 54 in the form of recesses 54, particularly slots 54, in the arms 5*b* of the needle shroud 5. The recesses 54 are also elongated with a main extension direction along the longitudinal axis and are longer than the ribs 61 so that, when engaged, a relative axial movement between the needle shroud 5 and the syringe holder 6 is possible.

Figure 44:
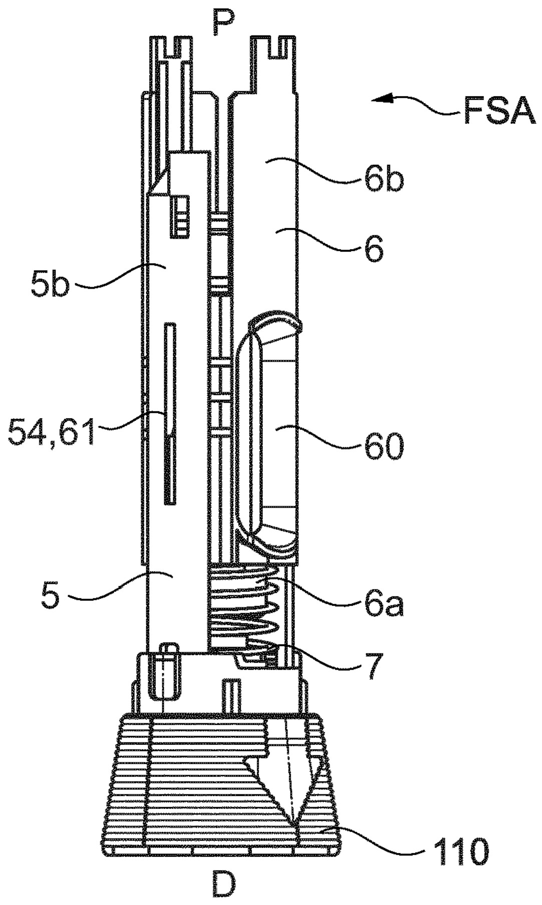
FIGS. 44 to 46 show sections of the front subassembly of the drug delivery device according to the first exemplary embodiment.

FIG. 44 shows the front subassembly FSA in perspective view. As previously described, the needle shroud 5 comprises two arms 5*b* which are positioned, along the angular direction, between two arms 6*b* of the syringe holder 6. The arms 6*b* of the syringe holder 6 project beyond the arms 5*b* of the needle shroud 5 in proximal direction P. The needle shroud 5 and the syringe holder 6 are coupled by the shroud spring 7 and the rotation-lock features 61, 54 so that the needle shroud 5 can be moved axially but not rotationally with respect to the syringe holder 6.

Figure 45:
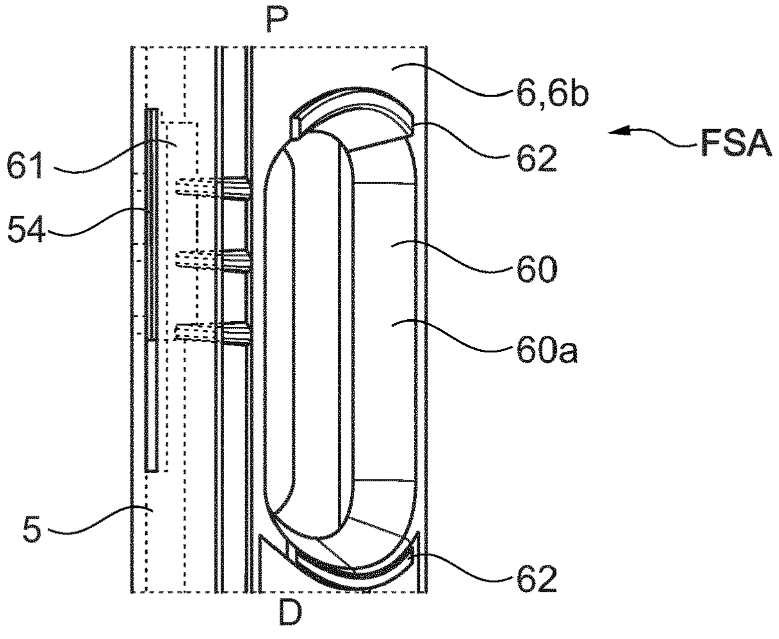

In FIG. 45, a section of the front subassembly FSA of FIG. 44 is shown. Windows 60 are formed in the arms 6*b* of the syringe holder 6, through which a syringe or medicament container located inside the syringe holder 6 can be investigated. The windows 60 are delimited by a wall portion 60*a* of the syringe holder 6. The diameter of the windows 60 decreases in inward radial direction.

The syringe holder 6 further comprises snap features 62, namely ribs, protruding in outward radial direction. A respective snap feature 62 is located at the distal end and at the proximal end of the window 60. The snap features 62 are configured to engage with the housing 100 to fix the syringe holder 6 to the housing 100 such that an axial and a rotational movement of the syringe holder 6 with respect to the housing 100 is prevented.

In FIG. 45, the ribs 61 project into the recesses 54 allowing an axial movement of the needle shroud 5 with respect to the syringe holder 6 but preventing a rotational movement of the needle shroud 5 with respect to the syringe holder 6. For that purpose, the width of the recesses 54 might be substantially as great as the width of the ribs 61.

Figure 46:
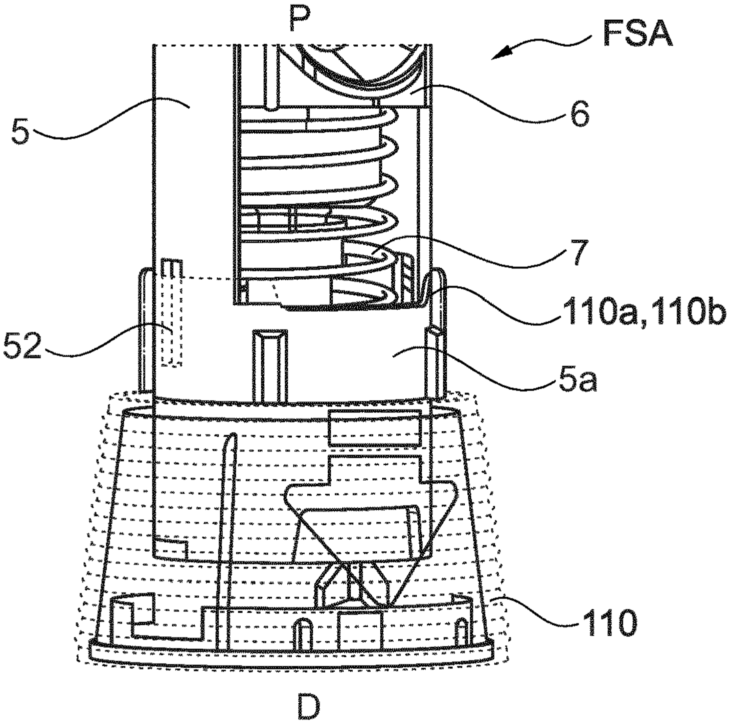

FIG. 46 shows a detailed view of the distal end of the front subassembly FSA with the cap 110 attached to the needle shroud 5. The protrusions 110*b* of the resilient arms 110*a* project into the recesses 52 of the needle shroud 5 so that the cap 110 is loosely held in position with respect to the needle shroud 5.

Figure 47:
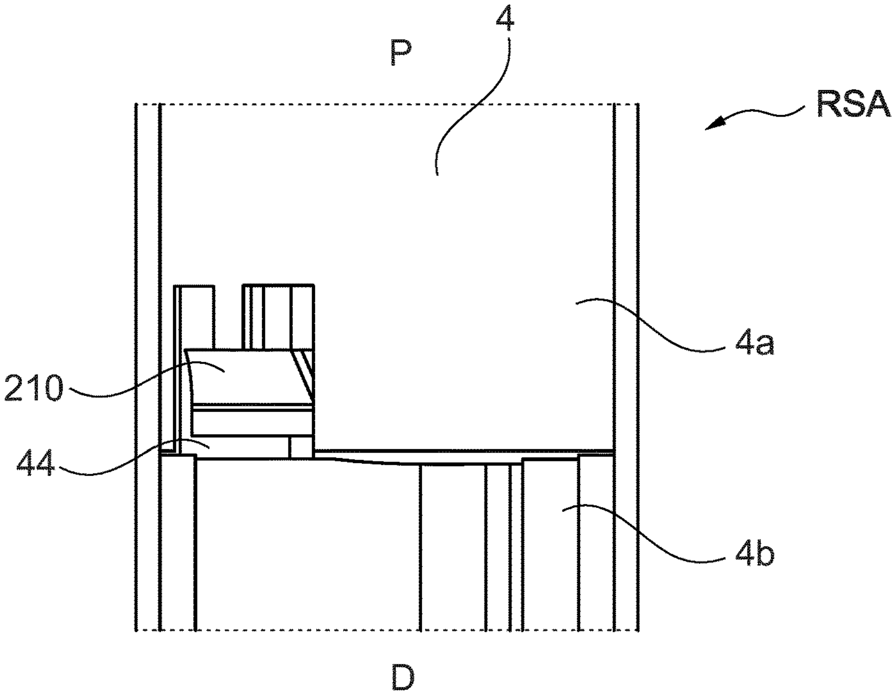
FIGS. 47, 48 and 50 to 53 show different positions in an exemplary embodiment of a method for assembling the drug delivery device according to the first exemplary embodiment.
Figure 48:
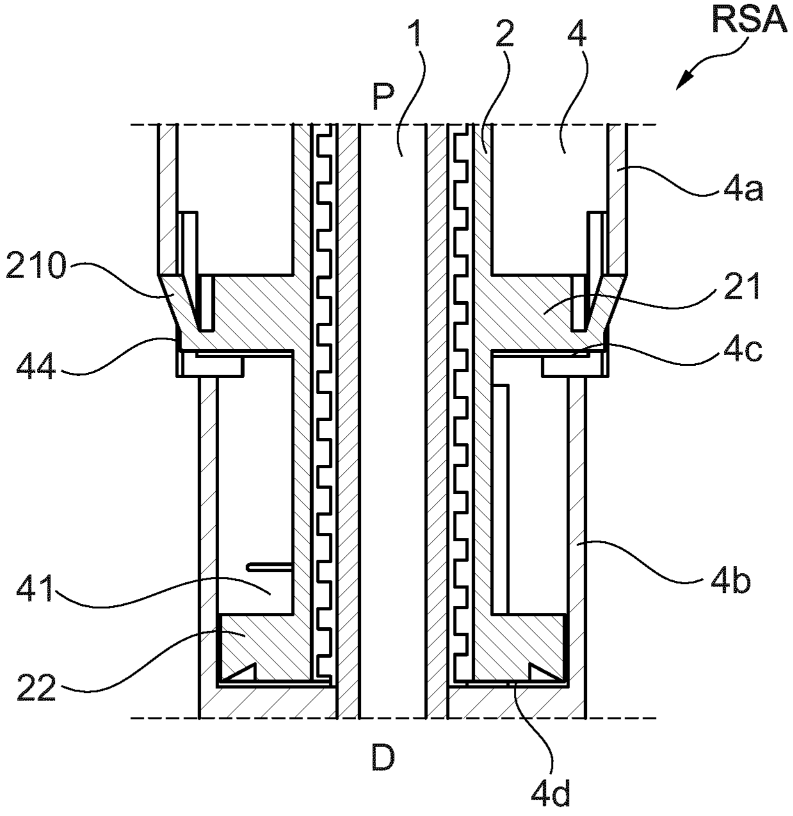
Figure 50:
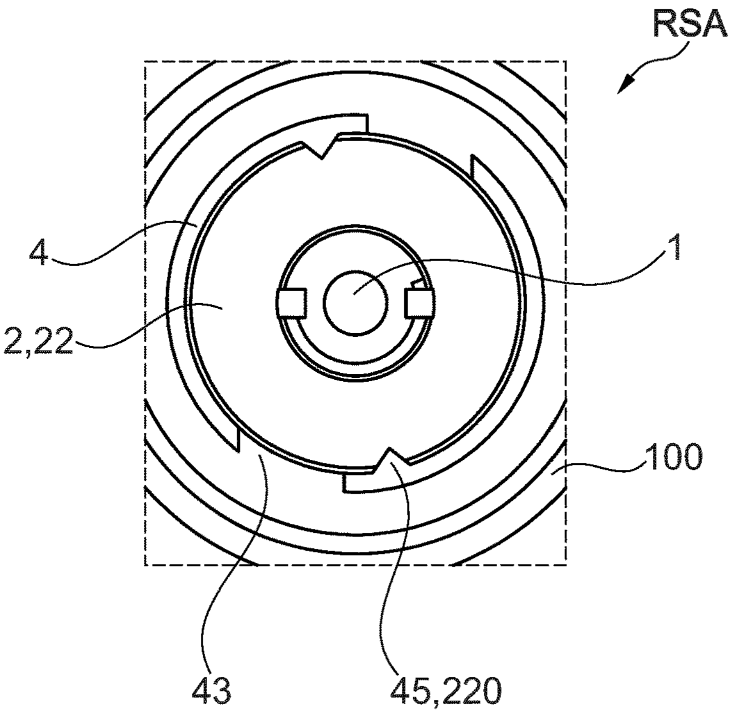

FIG. 47 shows a section of the rear subassembly RSA in perspective view. FIG. 48 shows the rear subassembly RSA in cross-sectional view with the longitudinal axis A running in the cutting plane. FIG. 50 shows the rear subassembly RSA in a cross-sectional view with the cutting plane running perpendicularly to the longitudinal axis A. An exemplary embodiment of the second locking mechanism is illustrated on the basis of these figures.

As can be seen in FIG. 47, a recess 44, particularly a cut-out, is formed in the first section 4*a* of the syringe holder 4. The first portion 21 of the rotating collar 2 comprises a displaceable axial-lock element 210 in form of a resilient arm 210 or clip 210. The resilient arm 210 is displaceable in radial direction. The resilient arm 210 is configured to project into the recess 44 when it is in a first radial position. In this case, the rear subassembly RSA is in a second locked state. The engagement of the resilient arm 210 and the recess 44 establishes an axial-lock interface and prevents a proximal movement of the rotating collar 2 with respect to the drive spring holder 4, because, when moving the rotating collar 2 in proximal direction P, the resilient arm 210 hits against an edge of the drive spring holder 4 delimiting the recess 44 in proximal direction P. This is one part of the second locking mechanism, also referred to as axial-locking mechanism.

As can be seen in FIG. 48, in the second locked state, the second portion 22 of the rotating collar 2 abuts against the second bottom ring 4*d* of the drive spring holder 4. The first portion 21 of the rotating collar 2 abuts against the first bottom ring 4*c* of the drive spring holder 4.

The second locking mechanism comprises also a protrusion 45 (see also FIG. 49) which is part of the second portion 4*b* of the drive spring holder 4 protruding radially inwardly. The protrusion 45 is not movable in any direction with respect to the rest of the drive spring holder 4. The protrusion 45 may have the same form as the first section 410*b* of the protrusion 410 of the resilient arm 41. The protrusion 45 is offset in distal direction D with respect to the resilient arm 41 or the protrusion 410, respectively. Furthermore, the second locking mechanism comprises the second section 22 of the rotating collar 2 with the above described recess 220 forming also part of the previously described first locking mechanism.

In the second locked state, the protrusion 45 projects into the recess 220 (see FIG. 50) thereby establishing a rotation-lock interface. This engagement prevents a rotation of the rotating collar 2 (the biased torsion drive spring 3 may already induce a torque onto the rotating collar 2 in the second locked state). This is another part of the second locking mechanism, also referred to a second rotation-locking mechanism.

The second rotation-locking mechanism does not need the needle shroud 5 for retaining the second locked state as the protrusion 45 is not displaceable in radial direction. Thus, as long as the rotating collar 2 is not moved in proximal direction P, a rotation of the rotating collar 2 is not possible.

Figure 51:
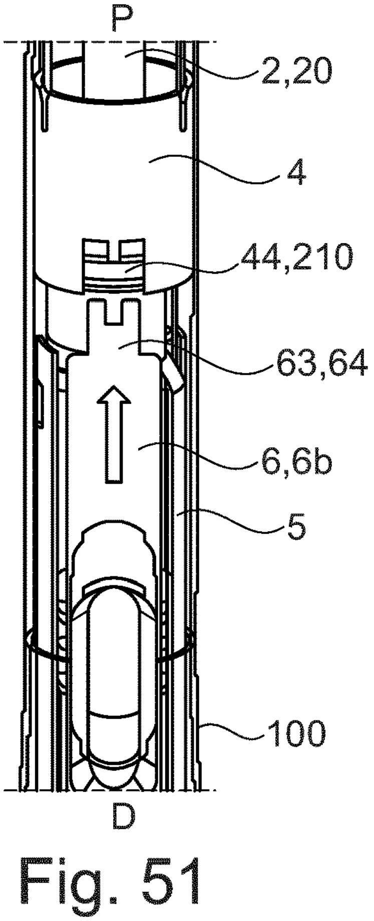
Figure 52:
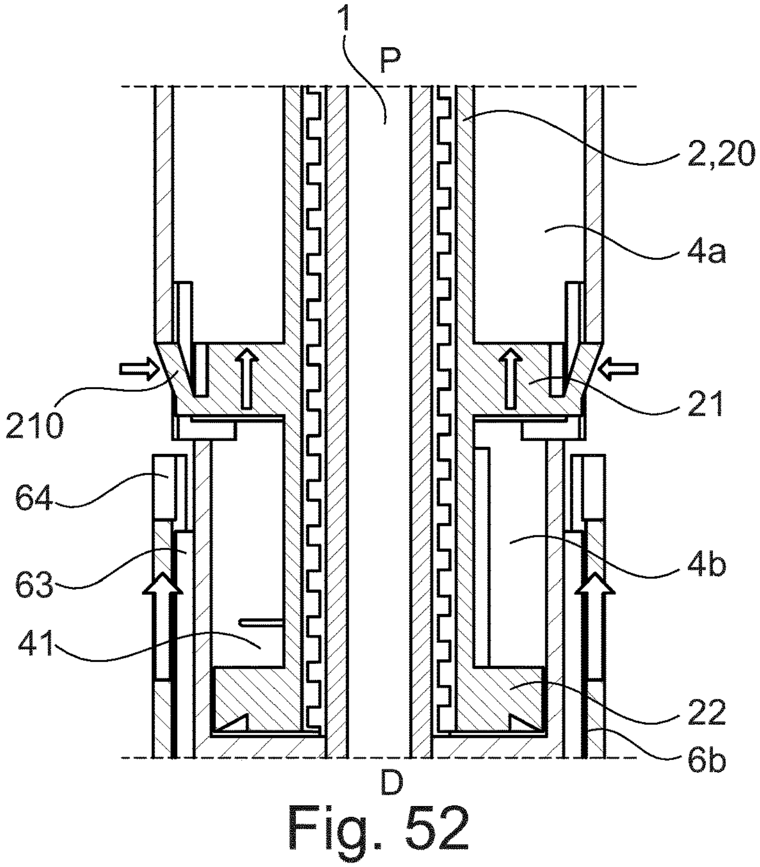

FIG. 51 shows a position in the assembly of the auto-injector, in which the rear subassembly and the front subassembly of the previous figures are telescoped into each other. FIG. 52 shows the same position in the assembling as FIG. 51 but in a cross-sectional view.

As can be seen in FIG. 52, the arms 6*b* of the syringe holder 6 each comprise or form at their proximal ends a push element 63 and a release element 64. The release element 64 protrudes beyond the push element 63 in proximal direction P. Moreover, the push element 63 is offset in inward radial direction with respect to the release element 64. When being telescoped into each other, the release element 64 first hits against the resilient arm 210 and forces the resilient arm 210 to move radially inwardly so that the axial-locking mechanism is released. This is realized by the resilient arm 210 having a beveled surface tilted with respect to the longitudinal axis so that a force acting on the beveled surface in proximal direction P pushes the resilient arm 210 in inward radial direction.

Figure 53:
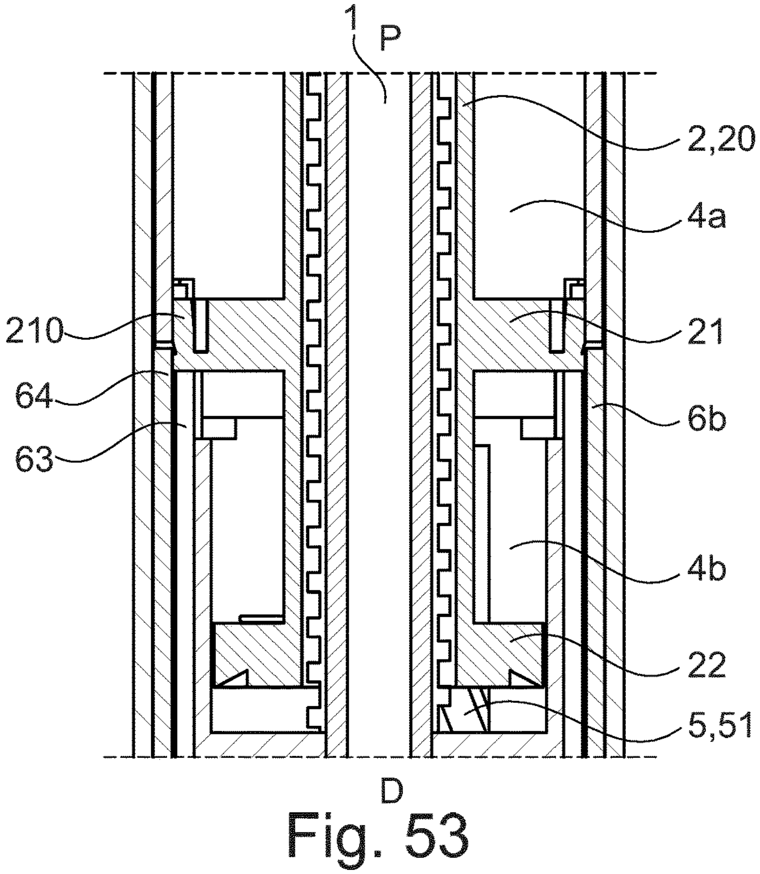

At the same time or later during telescoping the rear subassembly into the front subassembly, the push element 63 hits against the first section 21 of the rotating collar 2 and pushes the rotating collar 2 in proximal direction P (see also FIG. 53). This results in a release of the second rotation-locking mechanism and a transfer from the second locked state into the first locked state. The first locked state is occupied because the pushing of the rotating collar 2 in proximal direction P is accompanied with the needle shroud 5 being brought in the position where it holds the resilient arm 41 in its first radial position. Pushing the rotating collar 2 in proximal direction P during assembly has as a consequence that the recess 220 in the second portion 22 disengages with the protrusion 45 but before engages with the protrusion 410 of the resilient arm 41 (see also FIG. 49).

8. Feedback Mechanism

Figure 54:
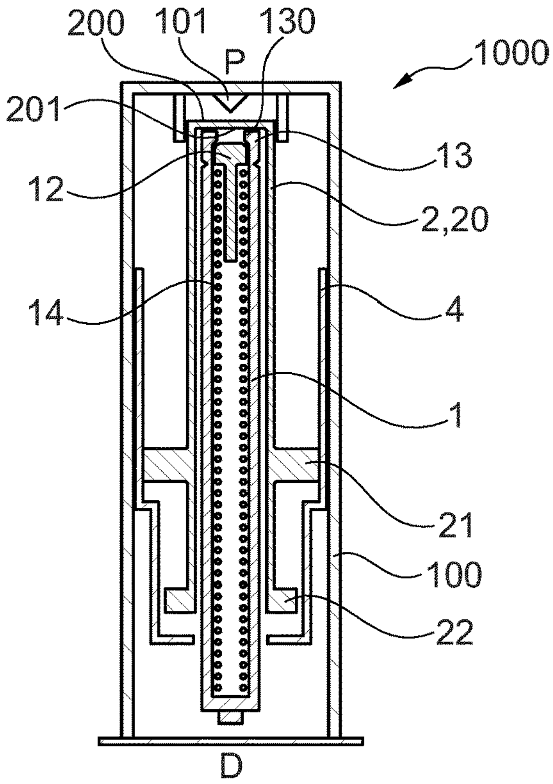
FIGS. 54 to 56 show an exemplary embodiment of a feedback mechanism in different positions.
Figure 55:
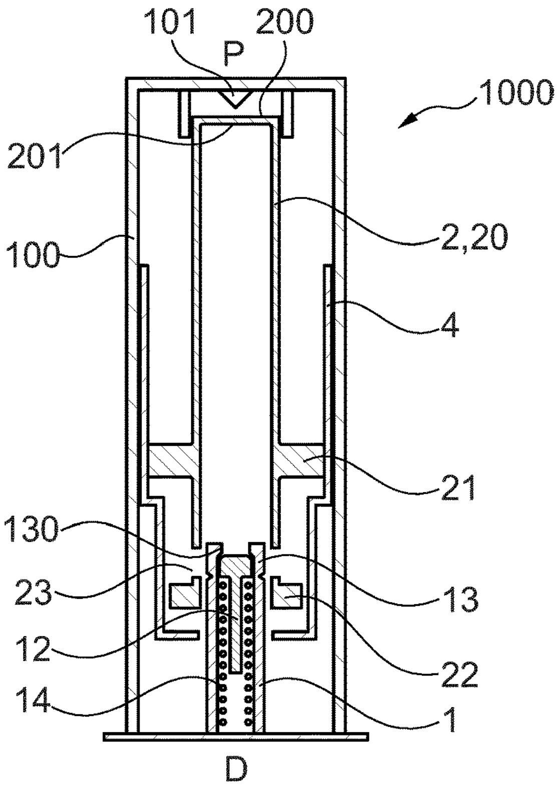
Figure 56:
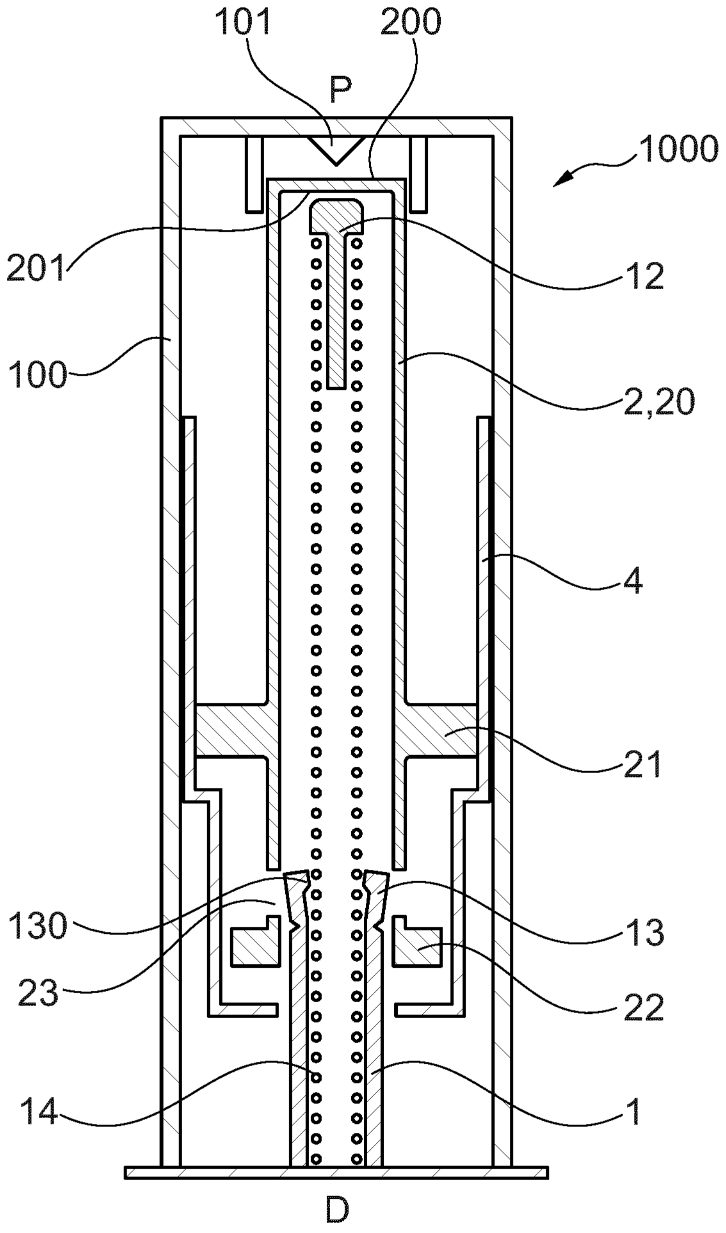

FIGS. 54 to 56 illustrate an exemplary embodiment of a feedback mechanism. Such a feedback mechanism can be used in any one of the exemplary embodiments of a drug delivery device described herein.

FIG. 54 shows a section of an exemplary embodiment of a drug delivery device/auto-injector 1000 with such a feedback mechanism. In FIG. 54, the auto-injector 1000 may be in the first locked state (initial state).

The feedback mechanism comprises a plunger rod 1 received in a rotating collar 2. The rotating collar 2 may be designed as described in connection with the previous figures. Particularly, the rotating collar 2 is a sleeve. The plunger rod 1 is hollow, e.g. hollow cylindrically-shaped. A feedback energy member 14 in the form of a spring 14, e.g. compression spring, is received in the plunger rod 1, i.e. in a cavity thereof. Furthermore, a feedback element 12 in the form of a piston 12 is received in the plunger rod 1. The spring 14 is connected to the piston 12 and to the plunger rod 1 and is compressed. The spring 14 induces a force onto the piston 12 pointing in proximal direction P, i.e. the piston 12 is biased in proximal direction P relative to the plunger rod 1.

The plunger rod 1 comprises displaceable arms 13 oriented in axial direction. The displaceable arms 13 may be resilient arms 13 and are located at the proximal end of the plunger rod 1. The displaceable arms 13 each comprise a stop feature 130 in the form of a protrusion 130 at their respective proximal end. The displaceable arms 13 together with their protrusions 130 are each displaceable in radial direction. The displaceable arms 13 are each in a first radial position.

They may be biased in the outward radial direction. However, the displaceable arms 13 are held in the first radial position by a sidewall of the rotating collar 2 circumferentially surrounding the plunger rod 1 at least at the height of the displaceable arms 13.

The protrusions 130 of the displaceable arms 13 project into the cavity of the plunger rod 1. The proximal end of the piston 12 abuts against the protrusions 130. This prevents a movement of the piston 12 in proximal direction P driven by the spring 14 beyond the protrusions 130.

As visible in FIG. 54, the piston 12 and the protrusions 130 each comprise slide features in the form of beveled surfaces tilted with respect to the longitudinal axis and the radial direction. The piston 12 and the protrusions 130 abut against each other at the beveled surfaces which biases the protrusions 130 or the displaceable arms 13, respectively, in outward radial direction.

FIG. 55 shows the auto-injector 1000 in the released state. The torsion drive spring induces a torque onto the rotating collar 2 which starts rotating in a first rotational direction and thereby the plunger rod 1 is moved in distal direction D. The biased spring 14 and the piston 12 move together with the piston rod 1 in distal direction D. During the movement, the displaceable arms 13 of the plunger rod 1 are held in the first radial position by the sidewall of the rotating collar 2 still circumferentially surrounding the resilient arms 13.

In a region of the distal end of the rotating collar 2, namely in the region between the first section 21 and the second section 22, the side wall of the rotating collar 2 is interrupted by a recess 23. When the plunger rod 1 reaches a feedback position, the displaceable arms 13 or the protrusions 130, respectively, axially and rotationally overlap with this recess 23. Thus, the displaceable arms 13 are no longer held in the first radial position. As they are biased radially outwardly, the displaceable arms 13 leave the first radial position and move in outward radial direction into a second radial position. In the second radial position, the piston 12 is no longer prevented from moving in proximal direction P relative to the plunger rod 1 driven by the spring 14 beyond the protrusions 130. This is illustrated in FIG. 56.

In FIG. 56, it can be seen that the piston 12, due to the force induced by the spring 14, moves in proximal direction P, thereby leaves the plunger rod 1 and finally hits against a proximal end 201 of the rotating collar 2 forming an impact feature 201. This hit may cause an audible and/or tactical feedback which indicates the user the end of the drug delivery process. For example, the auto-injector is designed such that the piston 12 hitting the impact feature 201 creates a noise of at least 20 dB.

9. Third Exemplary Embodiment of a Drug Delivery Device

Figure 57:
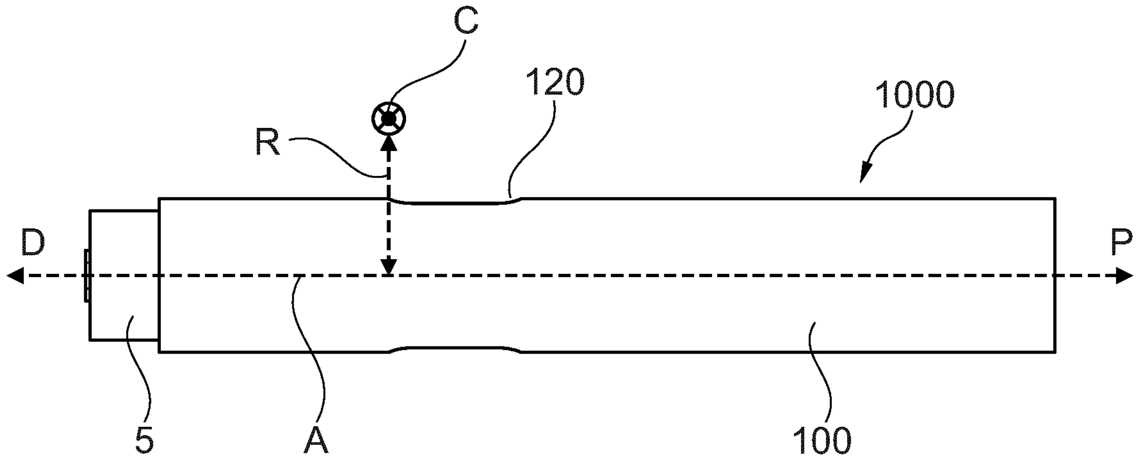
FIGS. 57 to 62 show a third exemplary embodiment of a drug delivery device in different views.
Figure 58:
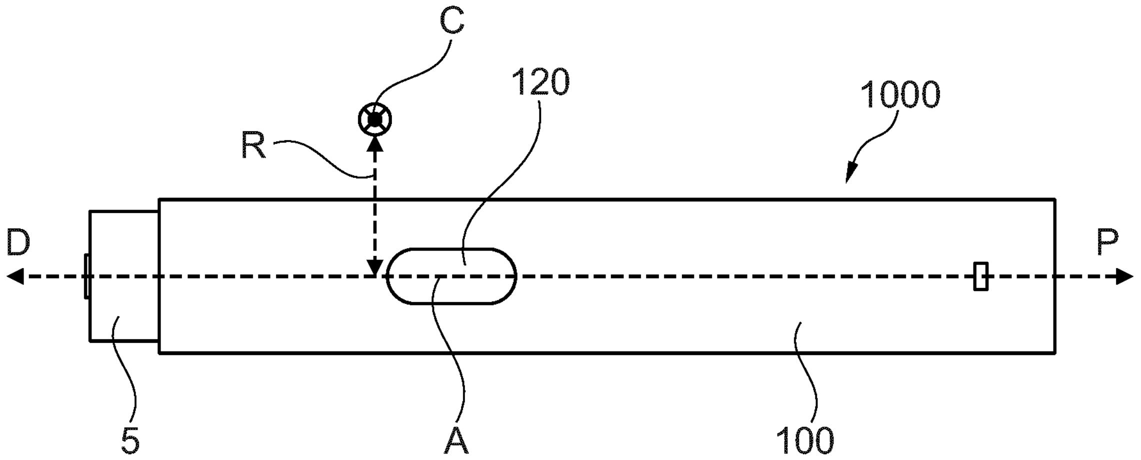

FIGS. 57 and 58 show a third exemplary embodiment of a drug delivery device 1000. FIG. 57 is a side view and FIG. 58 is a side view rotated by 90° around the longitudinal axis A with respect to FIG. 57. The drug delivery device 1000 is an auto-injector.

The auto-injector 1000 comprises a housing 100 with a window 120. The window 120 may be used for inspecting the fill level of a medicament container or a syringe or a progress of a stopper inside the housing 100 or the drug clarity or the degradation of the drug.

The auto-injector 1000 further comprises a protection member 5 in the form of a needle shroud 5 which is telescopically coupled to the housing 100 and is axially movable with respect to the housing 100.

Figure 59:
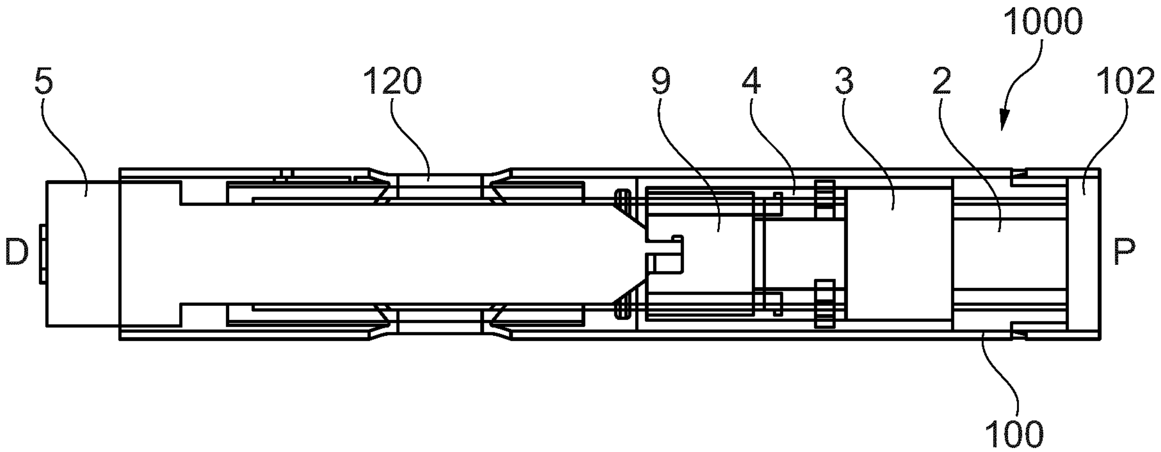
Figure 60:
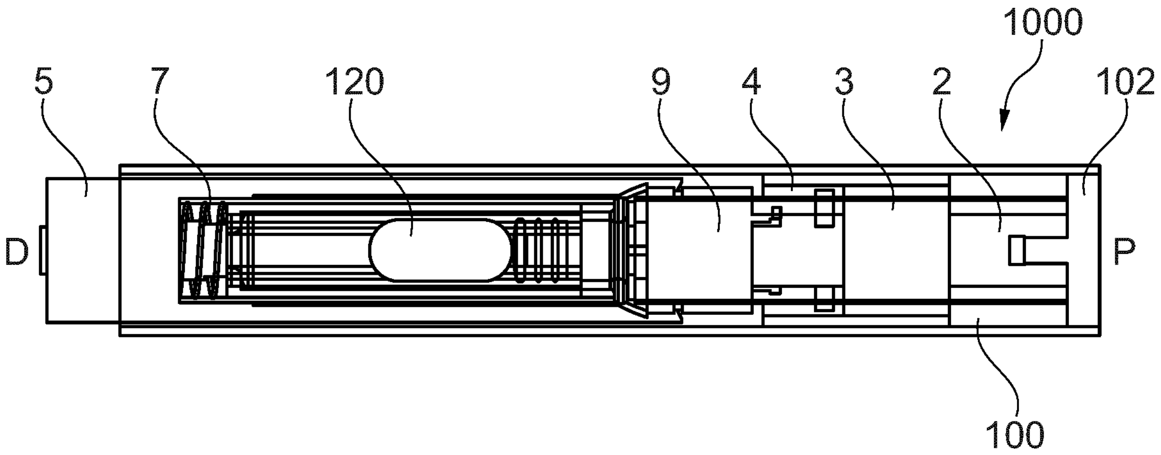

FIGS. 59 and 60 show the auto-injector 1000 of FIGS. 57 and 58 in the same views but now with the housing 100 being indicated semi-transparent which allows to see further members and elements of the auto-injector 1000. It can be seen, that the auto-injector 1000 further comprises a rear cap 102 which closes the housing 100 at the proximal end. Furthermore, the auto-injector 1000 comprises a drive spring holder 4, which is hollow, e.g. a sleeve. A torsion drive spring 3 is received in the drive spring holder 4. The torsion drive spring may be a spiral torsion spring. A rotating collar 2 is received in the torsion drive spring 3 and the drive spring holder 4. Moreover, a moveable member 9, also referred to as activation element 9, in the form of an activation collar 9 is provided. The activation collar 9 is releasably axially coupled to the needle shroud 5 so that an axial movement of the needle shroud 5 induces an axial movement of the activation collar 9. The activation collar 9 is located downstream of the torsion drive spring 3 in distal direction D and circumferentially surrounds a portion of the rotating collar 2.

Furthermore, the auto-injector 1000 comprises a shroud spring 7 which couples the needle shroud 5 to the housing 100. The coupling via the shroud spring 7 is such that a proximal movement of the needle shroud 5 with respect to the housing 100 compresses the shroud spring 7. This compression biases the needle shroud 5 in distal direction D relative to the housing 100.

Figure 61:
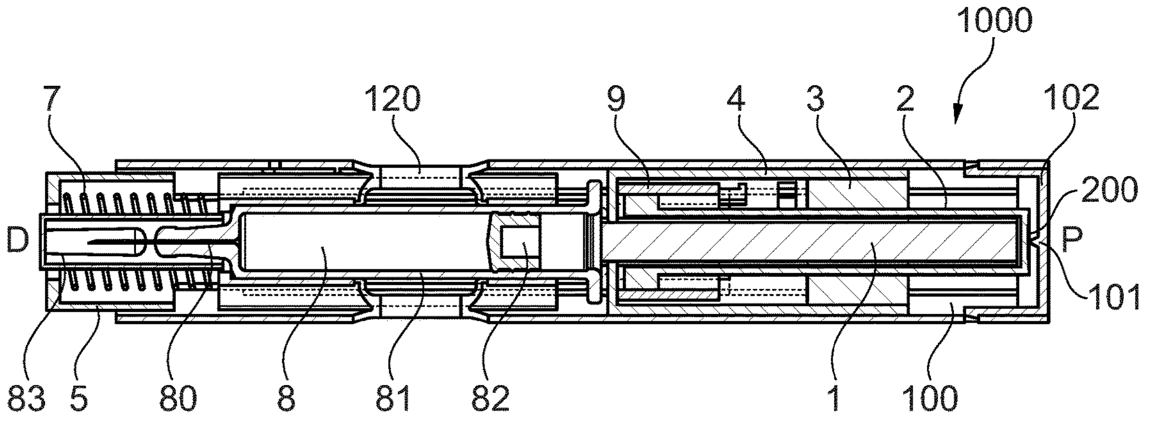
Figure 62:
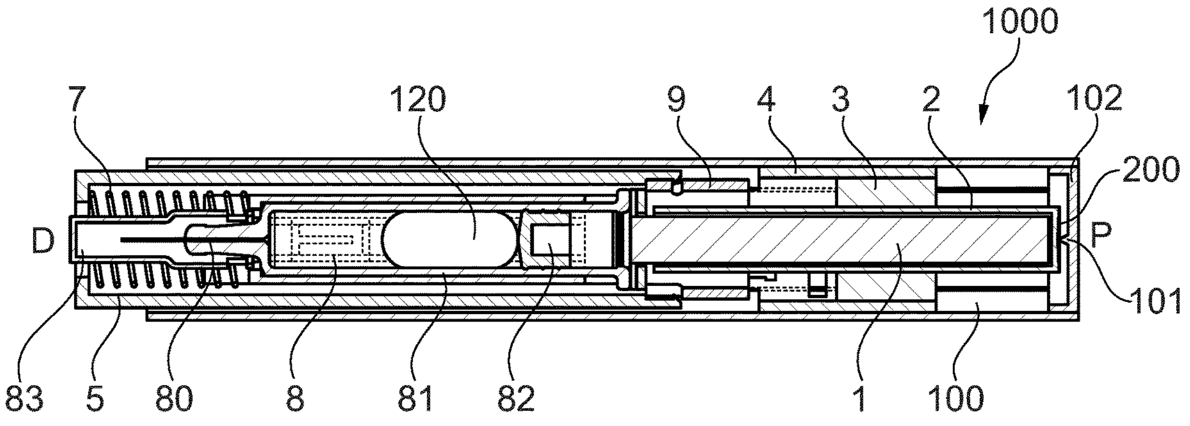

FIGS. 61 and 62 show the auto-injector 1000 of FIGS. 57 and 58 in the same views but now in a cross-sectional view with the cutting plane comprising the longitudinal axis A. In this view, it can be seen that the auto-injector 1000 further comprises a plunger rod 1. The plunger rod 1 is received in the rotating collar 2 and is circumferentially surrounded by the rotating collar 2. Only a small portion of the plunger rod 1 (less than 50% of its length) projects out of the rotating collar 2 in distal direction D. In proximal direction P, the rotating collar 2 is closed and the plunger rod 1 does not project beyond the proximal end of the rotating collar 2. The plunger rod 1 is longer, measured along the longitudinal axis, than the rotating collar 2.

The housing 100, the housing element 4, the plunger rod 1, the rotating collar 2, the needle shroud 5 and the activation element 9 may all comprise or consist of plastic. All these members may each be formed in one piece. The drive spring 3 and the shroud spring 7 may comprise or consist of a metal, e.g. steel.

It can be seen in FIGS. 61 and 62 that a medicament container 8, in the present case a syringe 8, is arranged in the housing 100. This syringe 8 may be arranged axially and/or rotationally and/or radially fixed with respect to the housing 100. The syringe 8 comprises a cartridge 81 filled with a drug, a needle 80 and a stopper 82. The needle 80 is arranged at a distal end of the syringe 8. The stopper 82 seals the cartridge 81 in proximal direction P. When moving the stopper 82 in the distal direction D, the drug stored in the cartridge 81 is pressed out of the syringe 8 through the needle 80.

In FIGS. 61 and 62 it can be further seen that the needle 80 is covered by a needle shield 83 which encapsulates the needle 80 and projects beyond the needle 80 in distal direction D. The needle shield 83 may be removed before using the auto-injector 1000.

For using the auto-injector 1000, the distal end of the auto-injector 1000 formed by the needle shroud 5 may be pressed against a body, e.g. a human body. As a consequence of that, the needle shroud 5 moves from its extended position in the proximal direction P with respect to the housing 100. This results in the needle 80 being exposed and projecting in distal direction D so that it can now pierce into the tissue of the body.

In the position shown in FIGS. 61 and 62, the auto-injector 1000 is still in an initial state, in the following referred to as locked state, in which the torsion drive spring 3 is biased and induces a torque onto the rotating collar 2. A locking mechanism, however, prevents the rotating collar 2 from a rotational movement. The locking mechanism will be explained in more detail further below.

In the locked state, a proximal end of the rotating collar 2 may be axially spaced from a proximal end-stop of the housing 100. This allows an axial movement of the rotating collar 2 in proximal direction P. Moreover, in the locked state, a distal end of the plunger rod 1 is axially spaced from the stopper 82 of the syringe 8. Thus, the plunger rod 1 can axially move in the distal direction D for a predetermined distance before hitting the stopper 82.

The needle shroud 5 may be moved in the proximal direction P into a retracted position. This releases the locking mechanism so that the rotating collar 2 is no longer prevented from rotating. The auto-injector switches from the locked state into a released state. The torque induced by the torsion drive spring 3 onto the rotating collar 2 forces the rotating collar 2 to rotate in a first rotational direction (clockwise or counterclockwise). For example, the rotating collar 2 rotates several times around its rotational axis. A drive mechanism, e.g. the drive mechanism described before, converts the rotation of the rotating collar 2 into an axial movement of the plunger rod 1 in the distal direction D. After having moved the predetermined distance in the distal direction D, the plunger rod 1 hits the stopper 82 of the syringe 8 and can now push the stopper 82 in distal direction D which results in the drug in the cartridge 81 being pressed out through the needle 80 into the tissue.

The rotating collar 2 may not only rotate but also moves in proximal direction P until the proximal end of the rotating collar 2 hits the proximal end-stop of the housing 100. The end-stop comprises is a protrusion 101 which tapers in distal direction D. The protrusion 101 may be a cone. The proximal end of the rotating collar 2 comprises an indentation 200. For example, the surface of the proximal end of the rotating collar 2 is concavely shaped. The protrusion 101 can penetrate into the indentation 200 when the proximal end of the rotating collar 2 hits the end-stop of the housing 100. The protrusion 101 and the indentation 200 may each be designed rotationally symmetric or circular symmetric with respect to the rotational axis of the rotating collar 2. In this way, a low friction interface is formed between the housing 100 and the rotating collar 2 so that a low friction rotation of the rotating collar 2 is enabled also when the proximal end of the rotating collar 2 abuts against the housing 100. Particularly, the radius at which the friction between the rotating collar 2 and the end-stop acts is approaching zero or is zero, therefore the resulting torque from the friction also tends to zero significantly reducing losses allowing a reduced spring force and/or enhance injection performance.

Figure 63:
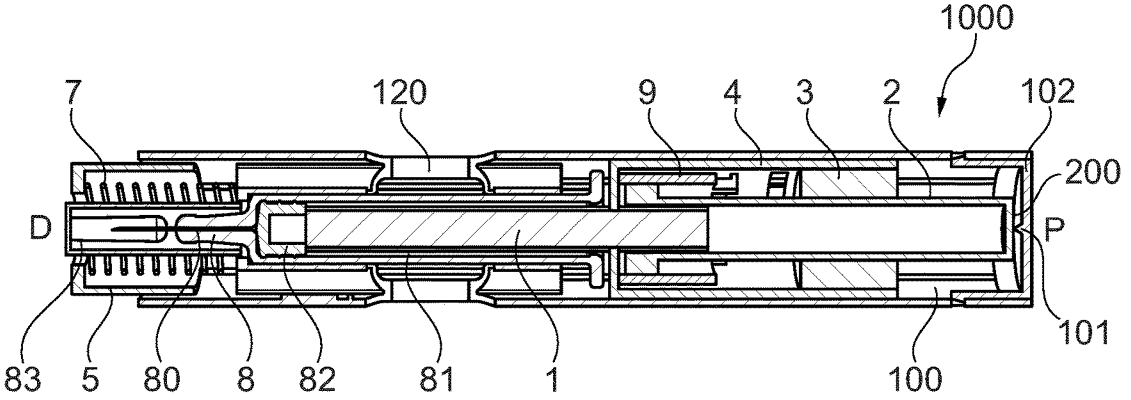
FIG. 63 shows the drug delivery device according to the third exemplary embodiment after usage.

FIG. 63 shows the auto-injector 1000 according to the third exemplary embodiment in a cross-sectional view and after usage. The plunger rod 1 has hit the stopper 82 and has pushed the stopper 82 into distal direction D. As a consequence, the drug in the cartridge 82 was pushed through the needle 80 out of the syringe 8. For example, the drug was thereby injected into the tissue of the body.

Figure 64:
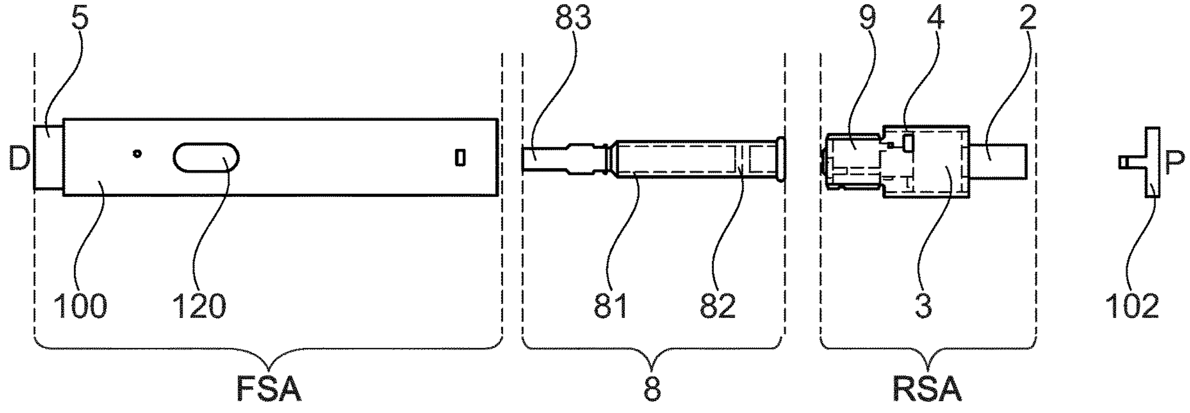
FIG. 64 shows different subassemblies of the drug delivery device according to the third exemplary embodiment.

FIG. 64 shows different subassemblies of the auto-injector 1000 according to the third exemplary embodiment. The auto-injector 1000 comprises a front subassembly FSA. The front subassembly FSA comprises the housing 100, the needle shroud 5 and the shroud spring 7 coupling the housing 100 and the needle shroud 5.

The auto-injector 1000 further comprises a rear subassembly RSA, with the plunger rod 1, the rotating collar 2, the torsion drive spring 3, the drive spring holder 4 and the activation collar 9.

When assembling the front subassembly FSA and the rear subassembly RSA, a syringe 8 is first telescoped into the housing 100 of the front subassembly FSA and then the rear subassembly RSA is telescoped into the housing 100. Finally the rear cap 102 is attached to the proximal end of the housing 100 and may be fixed to the housing 100 via a clip.

Figure 65:
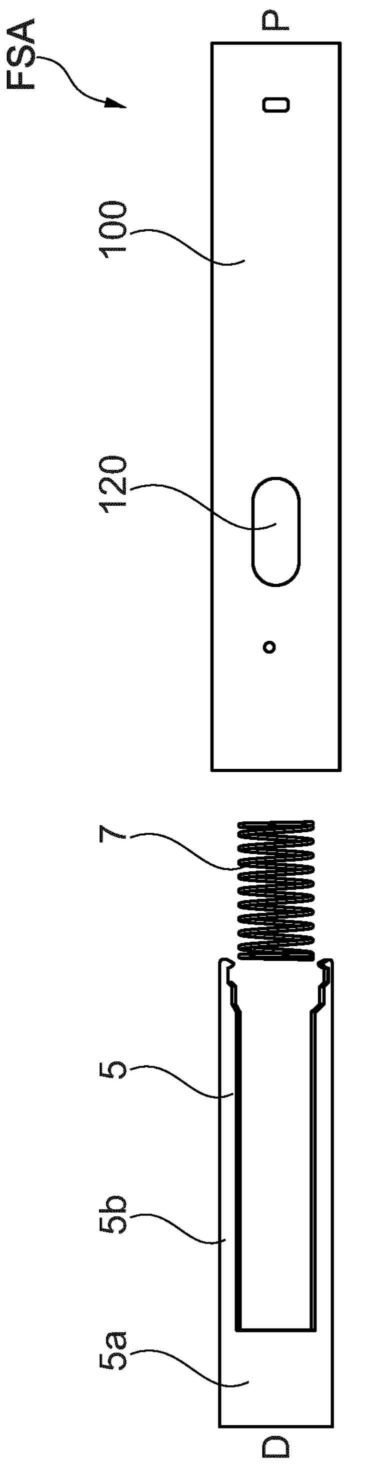
FIGS. 65 and 66 show the subassemblies of the drug delivery device according to the third exemplary embodiment in exploded views.

FIG. 65 shows the front subassembly FSA in an exploded view. The needle shroud 5 comprises a distal portion **5*a* which is shaped hollow cylindrically and into which the shroud spring 7 can be telescoped. Furthermore, the needle shroud 5 comprises two arms 5*b* extending from the cylindrically shaped portion 5*a*** in proximal direction P.

Figure 66:
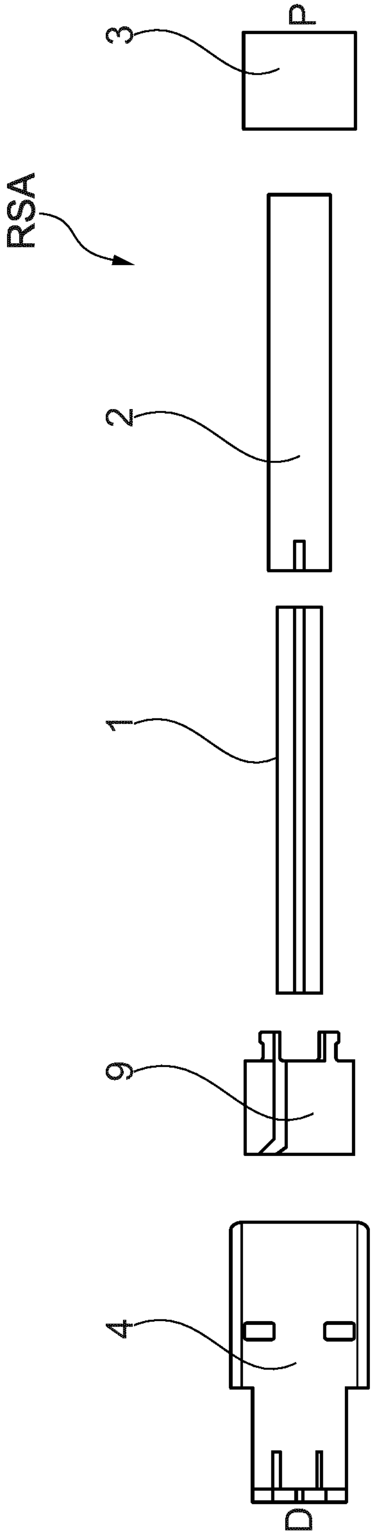

FIG. 66 shows the rear subassembly RSA in an exploded view.

9.1 Drive Mechanism of the Drug Delivery Device According to the Third Exemplary Embodiment The drive mechanism of the auto-injector according to the third exemplary embodiment may be designed as the previously described drive mechanism.

Figure 67:
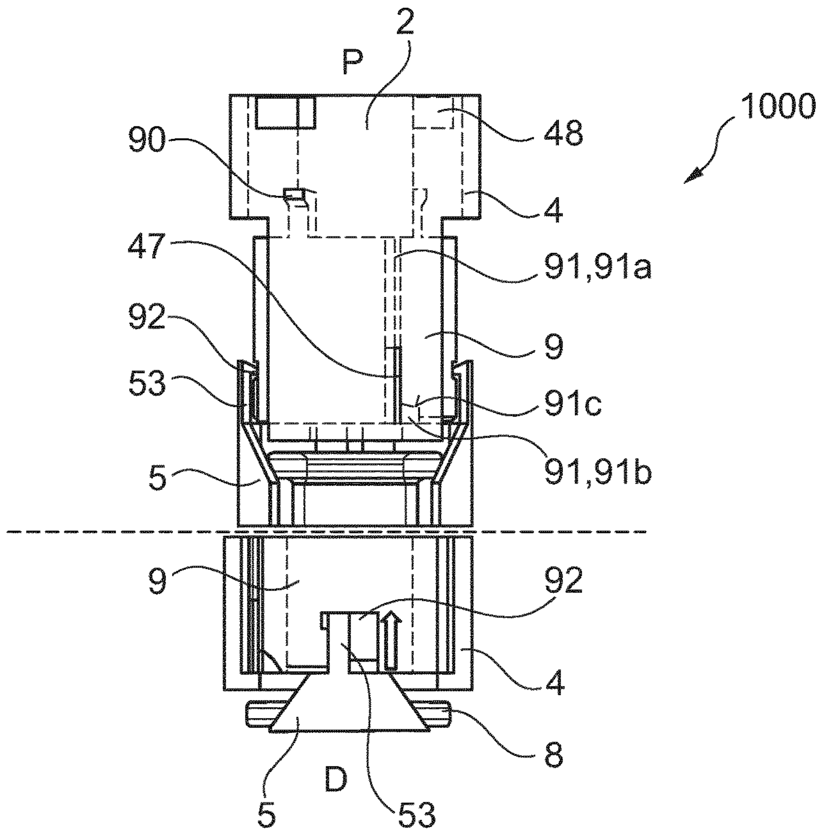
FIGS. 67 to 70 show sections of the drug delivery device according to the third exemplary embodiment in different positions during usage for illustrating a locking mechanism.

9.2 Locking Mechanism of the Drug Delivery Device According to the Third Exemplary Embodiment FIG. 67 shows sections of the auto-injector 1000 according to the third exemplary embodiment in the locked state.

The upper part of FIG. 67, above the horizontal dashed line, shows a section of the auto-injector 1000 in a side view. The lower part of FIG. 67, below the dashed line, shows a section of the auto-injector in a side view rotated by 90° around the longitudinal axis A with respect to the upper part.

Figure 70:
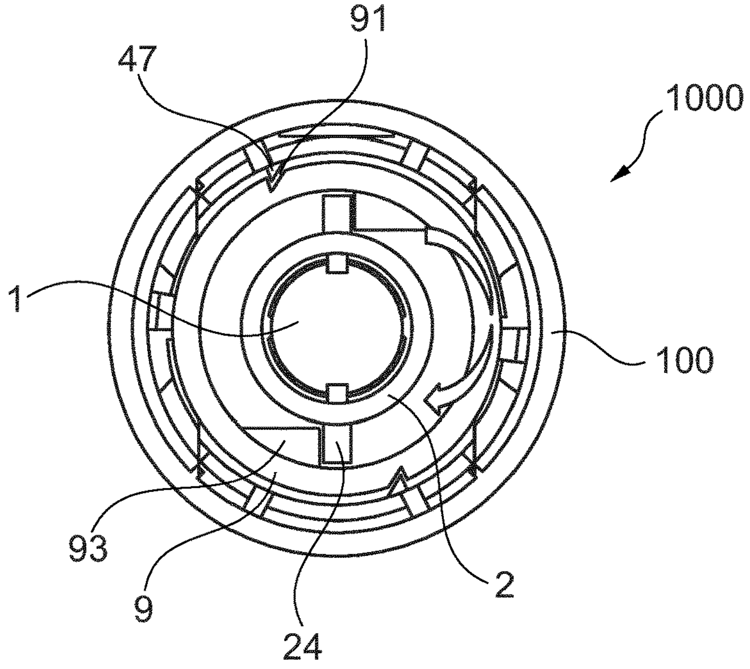

FIG. 70 shows the auto-injector 1000, e.g. also in the locked state, in a cross-sectional view with the crossing plane being perpendicular to the longitudinal axis A.

Considering first FIG. 67, the needle shroud 5 comprises a coupling feature 53 in the form of a resilient arm 53 with a protrusion projecting radially inwardly. The activation collar 9 has a coupling feature 92 in the form of a recess 92 or opening 92. The protrusion of the resilient arm 53 projects into the recess 92. In this way, the needle shroud 5 and the activation collar 9 are axially coupled so that an axial movement of the needle shroud 5 induces an axial movement of the activation collar 9.

In the lower part of FIG. 67 it can be seen that the recess 92 is L-shaped and comprises two sections being adjacent to each other in the angular direction. In the locked state shown in FIG. 67, the resilient arm 53 engages into a first section of the recess 92. The first section of the recess 92 is bordered in proximal direction P and distal direction D by edges of the activation collar 9. Thus, an axial movement of the needle shroud 5 in proximal direction P and distal direction D results in the protrusion of the resilient arm 53 hitting either one of these edges. As a consequence, the activation collar 9 is forced to move in distal direction D when the needle shroud 5 is moved in distal direction D and the activation collar 9 is forced to move in proximal direction P when the needle shroud 5 is moved in proximal direction P. In other words, the needle shroud 5 is coupled to the activation collar 9 in proximal direction P and distal direction D.

On the other hand, the second section of the recess 92 is delimited by an edge of the activation collar 9 only in proximal direction P. In distal direction D, the second section of the recess 92 is open and not delimited by an edge of the activation collar 9. Thus, if the protrusion of the resilient arm 53 would engage into the second section of the recess 92, the protrusion would hit against an edge of the activation collar 9 when moving the needle shroud 5 in proximal direction P which would force the activation collar 9 to also move in proximal direction P. A movement of the needle shroud 5 in distal direction D, however, would result in a disengagement of the resilient arm 53 and the recess 92.

Furthermore, it can be seen in FIG. 67 that the activation collar 9 is coupled to the drive spring holder 4 via a first rotation-lock interface. The first rotation-lock interface prevents a rotation of the activation collar 9 with respect to the drive spring holder 4. On the other hand, as can be seen in FIG. 70, the rotating collar 2 and the activation collar 9 are coupled via a second rotation-lock interface. The second rotation-lock interface prevents a rotation of the rotating collar 2 with respect to the activation collar 9. Thus, in sum, a rotation of the rotating collar 2 with respect to the drive spring holder 4 is prevented by the two rotation-lock interfaces.

The first rotation-lock interface is established by a slit 91*a* in the activation collar 9 and a rib 47 of the drive spring holder 4 engaging into the slit 91. The rib 47 and the slit 91 are each elongated with a main extension direction along the longitudinal axis. As can be seen in FIG. 67, the slit 91*a* is a first section of a recess 91 in the activation collar 9. The recess 91 also comprises a second section 91*b* adjoining the slit 91*a* in distal direction D. The slit 91 has a smaller width, measured along the angular direction, than the second section 91*b*. The width of the second section 91*b* first increase in direction away from the slit 91*a* and then has a constant width. In this region of increasing width, the second section 91*b* is delimited by a beveled surface 91*c* of the activation collar 9 which is tilted with respect to the longitudinal axis and the rotational direction. This beveled surface 91*c* realizes a slide feature. In the locked state, shown in FIG. 67, the rib 47 engages into the slit 91*a* of the recess 91.

As can be seen in FIG. 70, the second rotation-lock interface is realized by a protrusion 93 of the activation collar 9 and a protrusion 24 of the rotating collar 2 abutting against each other in angular direction. The protrusion 93 of the activation collar 9 projects radially inwardly and the protrusion 24 of the rotating collar 2 projects radially outwardly. The protrusions 24, 93 abut against each other such that a rotation of the rotating collar 2 induced by the biased torsion drive spring 3 with respect to the activation collar 9 is prevented or blocked by the activation collar 9.

Figure 68:
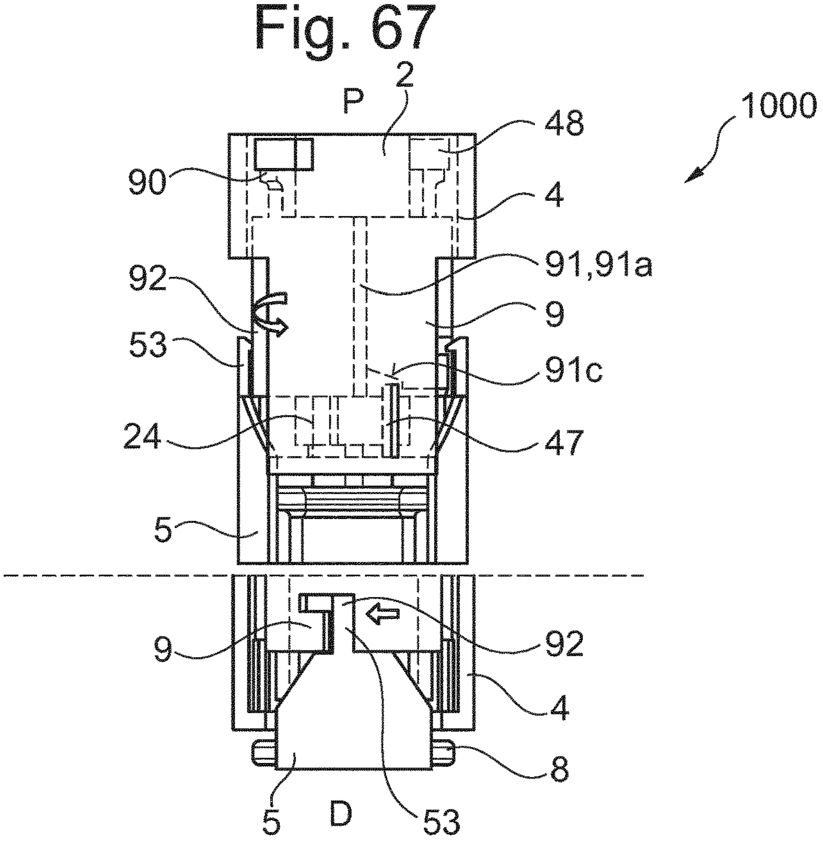

FIG. 68 shows the autoinjector 1000 in a position in which the needle shroud 5 has been moved from its extended position proximally towards the retracted position. The needle shroud 5 is now in an intermediate position between the extended position and the retracted position. In this intermediate position, the rib 47 is transferred from the slit into the second section 91*b*. Due to the force induced by the drive spring 3, the beveled surface 91*c* is pressed against the rib 47 and the rib 47 slides along the beveled surface 91*c* whereby the activation collar 9 rotates with respect to the drive spring holder 4 and with respect to the needle shroud 5 by a predetermined angle in the first rotational direction. This rotation happens automatically, as the torque induced by the torsion drive spring 3 is transferred via the rotating collar 2 to the activation collar 9 (via the second rotation-lock interface). After the rotation by the predetermined angle, an edge of the activation collar 9 running parallel to the longitudinal axis and delimiting the second section 91*b* of the recess 91 in angular direction hits against the rib 47. A further rotation of the activation collar 9 with respect to the drive spring holder 4 in the first rotational direction is then prevented.

However, the rotation of the activation collar 9 by the predetermined angle in the first rotational direction has as a consequence that the resilient arm 53 of the needle shroud 5 now engages into the second section of the recess 92 of the activation collar 9 which results in a decoupling of the activation collar 9 and the needle shroud 5 in distal direction D. In other words, the coupling of the needle shroud 5 and the activation collar 9 in distal direction D is released.

Figure 69:
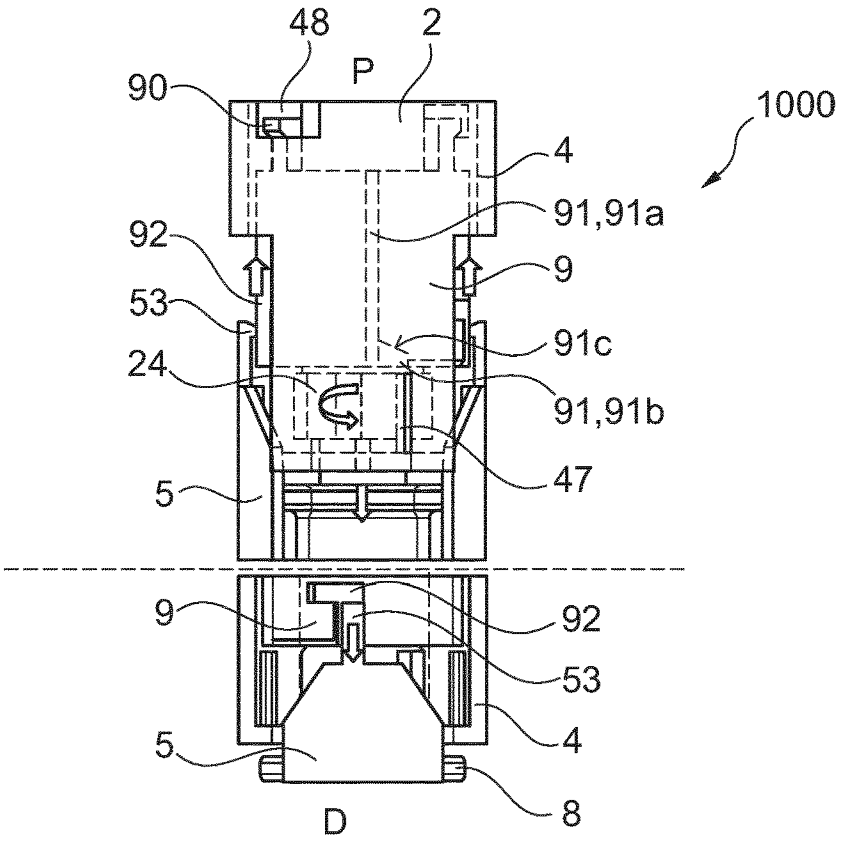

FIG. 69 shows the auto-injector 1000 in a position in which the needle shroud 5 has been further moved in proximal direction P into the retracted position which has also forced the activation collar 9 to further move in proximal direction P. In this retracted position of the needle shroud 5, the needle 80 of the auto-injector 1000 may be exposed allowing the needle 80 to pierce into a tissue of a body. In the retracted position of the needle shroud 5, the second rotation-lock interface between the activation collar 9 and the rotating collar 2 is released, i.e. the protrusion 24 and the protrusion 93 are now axially offset and do not abut against each other any longer so that the auto-injector 1000 transfers into the released state in which the rotation of the rotating collar 2 with respect to the activation collar 9 and with respect to the drive spring holder 4 is enabled. The rotating collar 2 rotates in the first rotational direction and thereby drives the plunger rod 1 in distal direction D which results in a delivery of the drug through the needle 80 (see description above).

Furthermore, the movement of the activation collar 9 further in proximal direction P had as a consequence that a second coupling feature 90 of the activation collar 9, namely a clip 90, has engaged into a coupling feature 48 of the drive spring holder 4, namely a recess 48. The engagement between the clip 90 and the recess 48 is such that a movement of the activation collar 9 in distal direction D is prevented. When moving the needle shroud 5 from the retracted position back towards or into the extended position, the activation collar 9 does not and cannot follow. A movement of the needle shroud 5 in distal direction D relative to the activation collar 9 is enabled since the resilient arm 53 engages into the second section of the recess 92 as described above.

Figure 71:
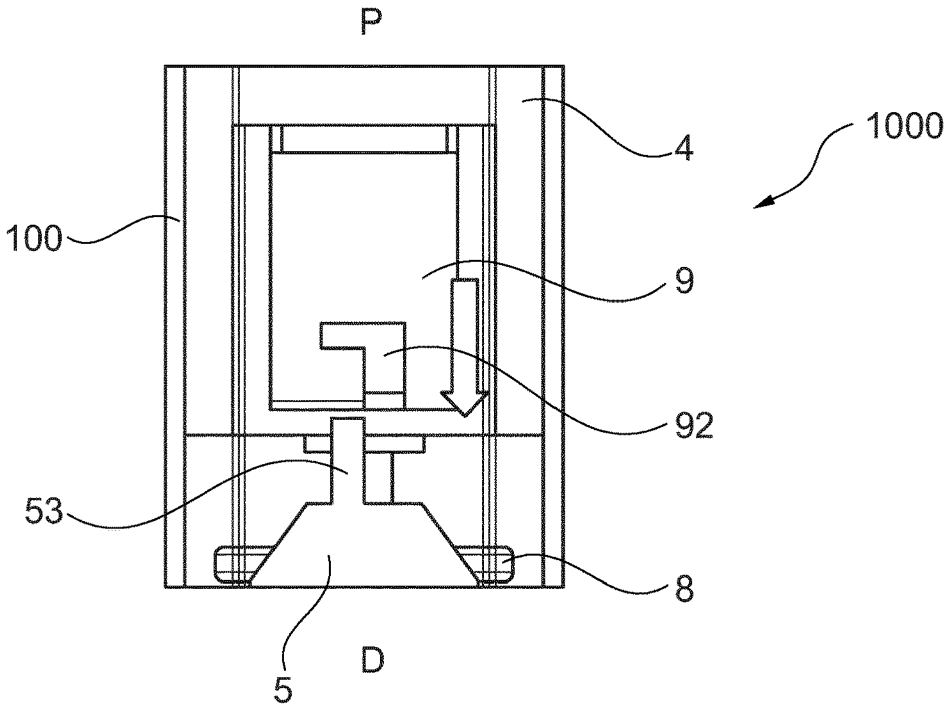
FIGS. 71 to 73 show different positions during assembling the drug delivery device according to the third exemplary embodiment.
Figure 72:
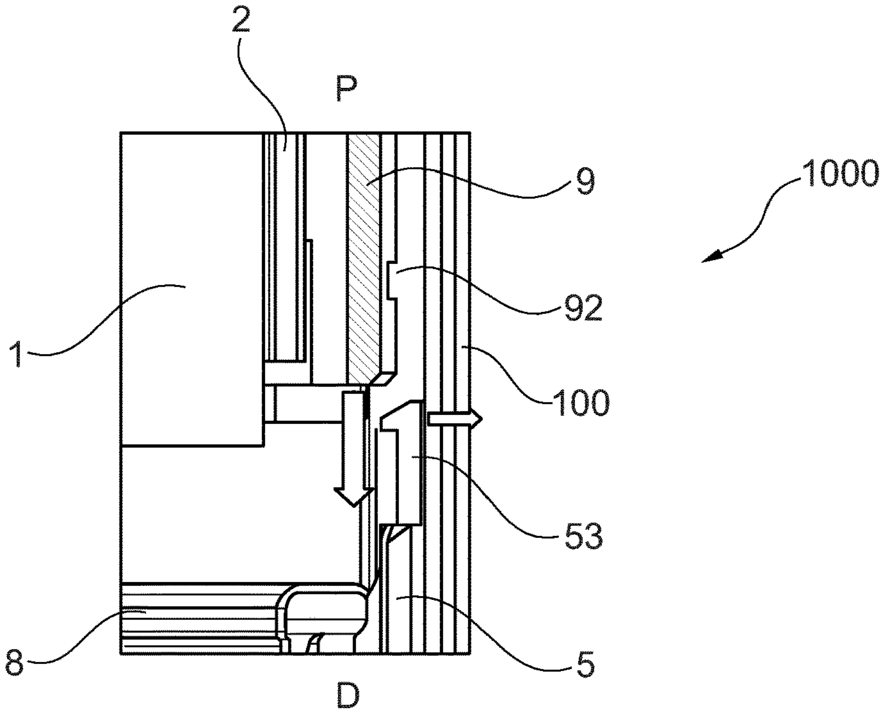
Figure 73:
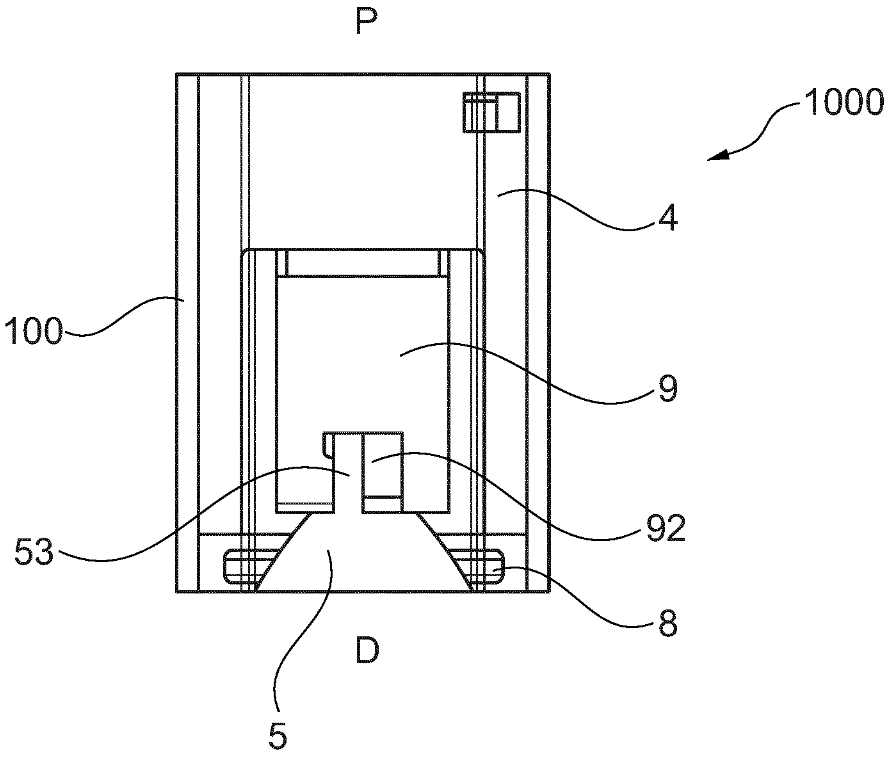

FIGS. 71 to 73 show different positions during assembling the auto-injector 1000 according to the third exemplary embodiment. The rear subassembly is telescoped into the front subassembly.

FIG. 71 shows a first position, in which the needle shroud 5 of the front subassembly and the activation collar 9 of the rear subassembly are not yet coupled to each other. FIG. 71 is a side view of the auto-injector 1000 during assembling.

FIG. 72 shows the position of FIG. 71 in a cross-sectional view. It can be seen, that the resilient arm 53 of the needle shroud 5 has a slide feature in form of a beveled surface. The beveled surface is designed such that, when the beveled surface hits the distal end of the activation collar 9, a force is created pushing the resilient arm 53 in outward radial direction. The rear subassembly and the front subassembly can then further be telescoped into each other and as soon as the protrusion of the resilient arm 53 axially and rotationally overlaps with the recess 92 of the activation collar 9, it slips into this recess 92. In this way, a coupling between the activation collar 9 and needle shroud 5 is obtained.

FIG. 73 shows the auto-injector after coupling of the needle shroud 5 and the activation collar 9.

Further Explanations and Definitions

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term, derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful with embodiments described in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof. An example drug delivery device may involve a needle-based injection system as described in Table 1 of section 5.2 of ISO 11608-1:2014(E). As described in ISO 11608-1:2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The embodiments described herein are not limited by the description in conjunction with the exemplary embodiments. Rather, any of the embodiments described herein may comprise any new feature as well as any combination of features, particularly including any combination of features in the patent claims, even if said feature or said combination per se is not explicitly stated in the patent claims or exemplary embodiments.

REFERENCE NUMERALS

1 plunger rod
2 rotating collar
3 torsion drive spring
4 drive spring holder
4*a* first section of drive spring holder 4
4*b* second section of drive spring holder 4
4*c* first bottom ring of drive spring holder 4
4*d* second bottom ring of drive spring holder 4
5 needle shroud
5*a* cylindrically-shaped portion
5*b* arm
6 medicament container holder/syringe holder
6*a* cylindrically-shaped portion
6*b* arm
6*c* support portion
7 shroud spring
8 medicament container/syringe
9 activation collar
10 groove
11 external thread
12 piston
13 displaceable arm
14 feedback energy member/spring
20 shaft
21 first portion
22 second portion
22*a* surface
23 recess
24 protrusion
40 protrusion
40*a* edge in drive spring holder 4
41 resilient arm
43 recess
44 recess
45 protrusion
46 flap
47 rib
48 recess
50*a* wall portion
50*b* recess
51 resilient arm
51*a* ramp
52 recess
53 resilient arm
54 recess
60 window
60*a* wall portion
61 rib
62 snap feature
63 push element
64 release element
80 needle
81 cartridge
82 stopper
83 needle shield
90 clip
91 recess
91*a* slit/first section of recess 91
91*b* second section of recess 91
91*c* tilted surface
92 recess
93 protrusion
100 housing
101 protrusion
102 rear cap
110 cap
110*a* resilient arm
110*b* protrusion
111 grabber
120 window
130 protrusion
200 indentation
201 impact feature
210 resilient arm/clip
220 recess
220*b* first section of recess 220
220*c* second section of recess 220
220*d* surface of recess 220
221 recess
221*a* beveled surface
410 protrusion
410*a* beveled surface
410*b* first section of protrusion 410
410*c* second section of protrusion 410
410*d* surface of protrusion 410
411 protrusion
411*a* beveled surface
1000 drug delivery device/auto-injector
FSA front sub assembly
RSA rear sub assembly
α angle
D distal direction
P proximal direction
A longitudinal axis/axial direction
R radial direction
C azimuthal/rotational/angular direction

The invention claimed is:

1. An arrangement for a drug delivery device, the arrangement comprising:
a housing element;
a plunger rod being arranged axially movable with respect to the housing element and rotationally fixed with respect to the housing element;

a transfer member being arranged rotatably with respect to the housing element; and an energy member configured to provide energy to provide a torque onto the transfer member, wherein the transfer member and the plunger rod are operatively coupled such that a rotation of the transfer member is converted into an axial movement of the plunger rod, wherein the arrangement comprises a released state in which (i) the energy member provides the torque onto the transfer member and (ii) the transfer member rotates in a first rotational direction due to the torque and forces the plunger rod to move axially in a distal direction, and wherein the arrangement is configured such that, in the released state, the transfer member is configured to move proximally with respect to the housing element until the transfer member contacts an end-stop of the arrangement.

2. The arrangement according to claim 1, wherein the plunger rod is rotationally fixed to the housing element via a splined interface.

3. The arrangement according to claim 1, wherein in the released state, the transfer member rotates by at least n-times 360°, wherein n is an integer greater than or equal to 1.

4. The arrangement according to claim 1, wherein the plunger rod and the transfer member are operatively coupled via a threaded interface.

5. The arrangement according to claim 1, wherein:

the arrangement has a first locked state, in which a releasable first locking mechanism prevents a rotational movement of the transfer member, the first locking mechanism comprises a first rotation-lock element rotationally and axially fixed with respect to the transfer member and a second rotation-lock element rotationally and axially fixed with respect to the housing element, the first and second rotation-lock elements of the first locking mechanism being configured to engage each other, and the engagement of the first and second rotation-lock elements of the first locking mechanism prevents the rotational movement of the transfer member.

6. The arrangement according to claim 5, wherein:

the second rotation-lock element is a displaceable element, the displaceable rotation-lock element is displaceable in a radial direction, and the displaceable rotation-lock element is orientated circumferentially.

7. The arrangement according to claim 1, wherein:

the arrangement has a second locked state in which a releasable second locking mechanism prevents an axial movement and a rotational movement of the transfer member, the second locking mechanism comprises a first axial-lock element axially and rotationally fixed with respect the transfer member and a second axial-lock element rotationally and axially fixed with respect to the housing element, the first and second axial-lock elements of the second locking mechanism being configured to engage each other, the engagement of the first and second axial-lock elements of the second locking mechanism prevents the axial movement of the transfer member, the second locking mechanism comprises a first rotation-lock element rotationally and axially fixed with respect to the transfer member and a second rotation-lock element rotationally and axially fixed with respect to the housing element, the first and second rotation-lock elements of the second locking mechanism being configured to engage each other, and the engagement of the first and second rotation-lock elements of the second locking mechanism prevents the rotational movement of the transfer member.

8. The arrangement according to claim 7, wherein in the second locked state, the transfer member is axially offset with respect to a first locked state.

9. The arrangement according to claim 1, wherein in the released state and after contacting the end-stop, the transfer member is configured to continue to rotate.

10. The arrangement according to claim 1, wherein the transfer member is configured to move in a proximal direction.

11. The arrangement according to claim 1, wherein:

the end-stop comprises a first friction-reduction element, a proximal end of the transfer member comprises a second friction-reduction element, a low-friction interface is formed between the first and second friction reduction elements, at least one of the first or second friction reduction elements is a tapering protrusion, and the other one of the first or second friction reduction elements is an indentation.

12. The arrangement according to claim 11, wherein the indentation and/or the tapering protrusion are rotationally symmetric with respect to a rotational axis of the transfer member.

13. The arrangement according to claim 1, wherein:

the energy member is a drive spring connected to the transfer member at a first connection point and connected to the housing element at a second connection point, and during axial movement of the transfer member, the first connection point and the second connection point are axially moved with respect to each other.

14. The arrangement according to claim 1, wherein the arrangement has a first locked state in which a releasable first locking mechanism prevents a rotational movement of the transfer member and a second locked state in which a releasable second locking mechanism prevents an axial movement and the rotational movement of the transfer member, and wherein, in the second locked state, the transfer member is axially offset with respect to the first locked state.

15. A drug delivery device comprising:

a housing comprising a housing element fixed to or integrated in the housing;

a plunger rod being arranged axially movable with respect to the housing element and rotationally fixed with respect to the housing element;

a transfer member being arranged rotatably with respect to the housing element;

an energy member configured to provide energy to provide a torque onto the transfer member;

a medicament container with a needle; and a needle shroud telescopically coupled to the housing and axially movable with respect to the housing between an extended position in which the needle is covered by the needle shroud and a retracted position in which the needle is exposed, wherein the transfer member and the plunger rod are operatively coupled such that a rotation of the transfer member is converted into an axial movement of the plunger rod, wherein the drug delivery device comprises a released state in which (i) the energy member provides the torque onto the transfer member and (ii) the transfer member rotates in a first rotational direction due to the torque and forces the plunger rod to move axially in a distal direction, and wherein the drug delivery device is configured such that, in the released state, the transfer member is configured to move proximally with respect to the housing element until the transfer member contacts an end-stop of the arrangement.

16. The drug delivery device according to claim 15, wherein the medicament container comprises a drug.

17. The drug delivery device according to claim 15, wherein the drug delivery device is an auto-injector.

18. A method of dispensing the drug with the drug delivery device according to claim 16.

* * * * *